(12) United States Patent
Gouery et al.

(10) Patent No.: US 10,016,208 B2
(45) Date of Patent: Jul. 10, 2018

(54) CUTTING TIPS FOR ULTRASONIC SURGICAL SYSTEM

(71) Applicants: DePuy Synthes Products, Inc., Raynham, MA (US); Satelec SAS, Merignac (FR)

(72) Inventors: Gwenael D. Gouery, Palm Beach Gardens, FL (US); Eric B. Reno, West Chester, PA (US); Nuria Serra Malats, Oberdorf (CH); Yann Gallard, Le Haillan (FR); Vianney Ruellan, Bordeaux (FR)

(73) Assignees: DePuy Synthes Products, Inc., Raynham, MA (US); Satelec SAS, Merignac (FR)

( * ) Notice: Subject to any disclaimer, the term of this patent is extended or adjusted under 35 U.S.C. 154(b) by 572 days.

(21) Appl. No.: 13/757,247

(22) Filed: Feb. 1, 2013

(65) Prior Publication Data
US 2013/0204285 A1    Aug. 8, 2013

Related U.S. Application Data

(60) Provisional application No. 61/594,616, filed on Feb. 3, 2012.

(51) Int. Cl.
*A61B 17/32*    (2006.01)
*A61C 3/03*    (2006.01)

(52) U.S. Cl.
CPC .......... *A61B 17/320068* (2013.01); *A61B 2017/320004* (2013.01); *A61B 2017/320078* (2017.08); *A61C 3/03* (2013.01)

(58) Field of Classification Search
CPC .......... A61B 17/320068; A61B 2017/320072; A61B 2017/320076; A61B 2017/320004; A61B 2017/320078; A61B 17/22012; A61C 3/03
USPC ........................................................ 606/169
See application file for complete search history.

(56) References Cited

U.S. PATENT DOCUMENTS

| 4,188,952 | A | * | 2/1980 | Loschilov et al. ............ 606/79 |
| 5,180,363 | A | * | 1/1993 | Idemoto ......... A61B 17/320068 310/316.01 |
| 5,188,102 | A | * | 2/1993 | Idemoto ......... A61B 17/320068 604/22 |

(Continued)

FOREIGN PATENT DOCUMENTS

EP    0 394 583 A2    10/1990

OTHER PUBLICATIONS

International Patent Application No. PCT/US2013/024354: International Search Report and Written Opinion dated May 6, 2013, 11 pages.

*Primary Examiner* — Ryan J Severson
*Assistant Examiner* — Christian Knauss
(74) *Attorney, Agent, or Firm* — Baker & Hostetler LLP

(57) ABSTRACT

A tool is configured to cut a tissue body. The tool includes a first section configured to be coupled to a transducer assembly, and a second section coupled to the first section. The first section at least partially includes a first material. The second section at least partially includes a second material that is different from the first material and denser than the first material. The second includes a cutting member that is configured to vibrate at a predetermined frequency so as to cut a tissue body an operative portion.

9 Claims, 53 Drawing Sheets

(56) References Cited

U.S. PATENT DOCUMENTS

| | | | |
|---|---|---|---|
| 5,628,743 A * | 5/1997 | Cimino | A61B 17/320068 604/22 |
| 5,836,765 A * | 11/1998 | Hickok | 433/119 |
| 5,899,693 A * | 5/1999 | Himeno et al. | 433/119 |
| 6,379,371 B1 * | 4/2002 | Novak | A61B 17/320068 30/123.3 |
| 6,765,333 B1 | 7/2004 | Mariaucue et al. | |
| 6,910,889 B1 * | 6/2005 | Hickok | 433/119 |
| 2004/0024393 A1 | 2/2004 | Nita et al. | |
| 2004/0176686 A1 | 9/2004 | Hare et al. | |
| 2004/0265776 A1 * | 12/2004 | Tipton | A61C 3/03 433/119 |
| 2006/0195107 A1 * | 8/2006 | Jones | A61B 17/1624 606/79 |
| 2006/0235305 A1 * | 10/2006 | Cotter | A61B 17/1604 600/459 |
| 2007/0015102 A1 * | 1/2007 | Vercellotti | A61C 3/03 433/2 |
| 2007/0131034 A1 | 6/2007 | Ehlert et al. | |
| 2008/0188878 A1 | 8/2008 | Young | |
| 2008/0248444 A1 * | 10/2008 | Bahcall et al. | 433/119 |
| 2009/0326440 A1 * | 12/2009 | Lee | A61C 3/03 604/22 |
| 2009/0326535 A1 * | 12/2009 | Blus | 606/80 |
| 2010/0004558 A1 * | 1/2010 | Frankhouser | A61B 10/025 600/567 |
| 2010/0022824 A1 * | 1/2010 | Cybulski | A61B 1/00071 600/104 |
| 2011/0250560 A1 * | 10/2011 | Kwon et al. | 433/119 |
| 2011/0295294 A1 * | 12/2011 | Araya | 606/169 |
| 2012/0053492 A1 * | 3/2012 | Chang et al. | 601/2 |

\* cited by examiner

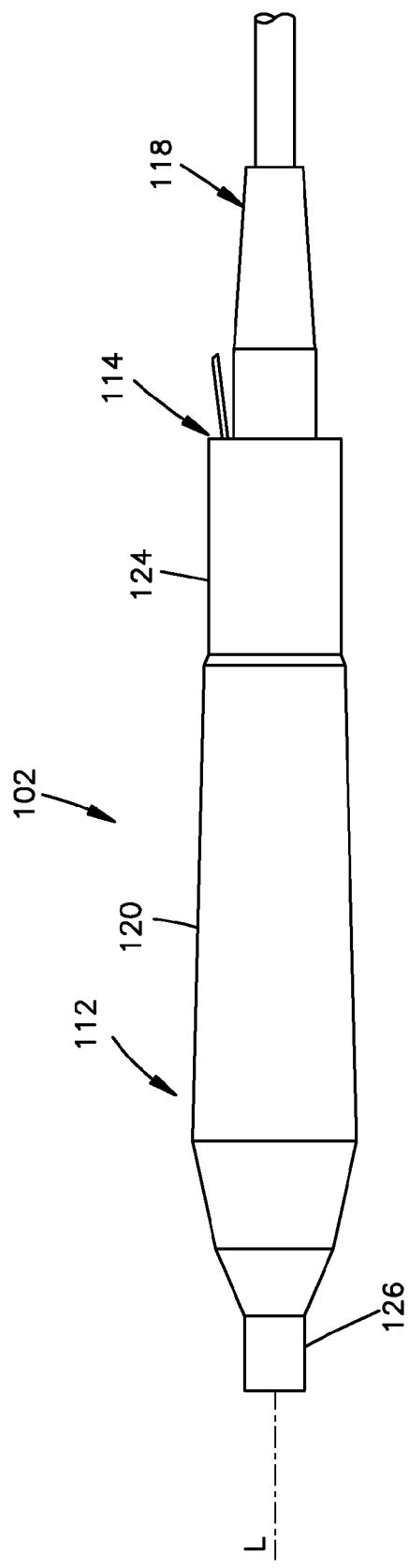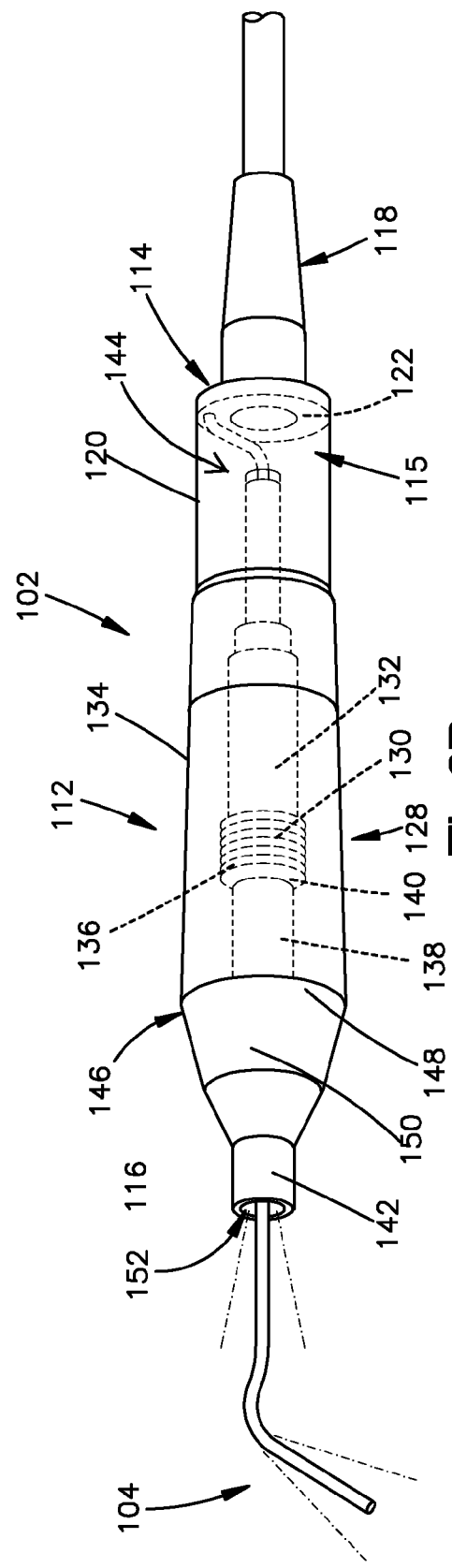

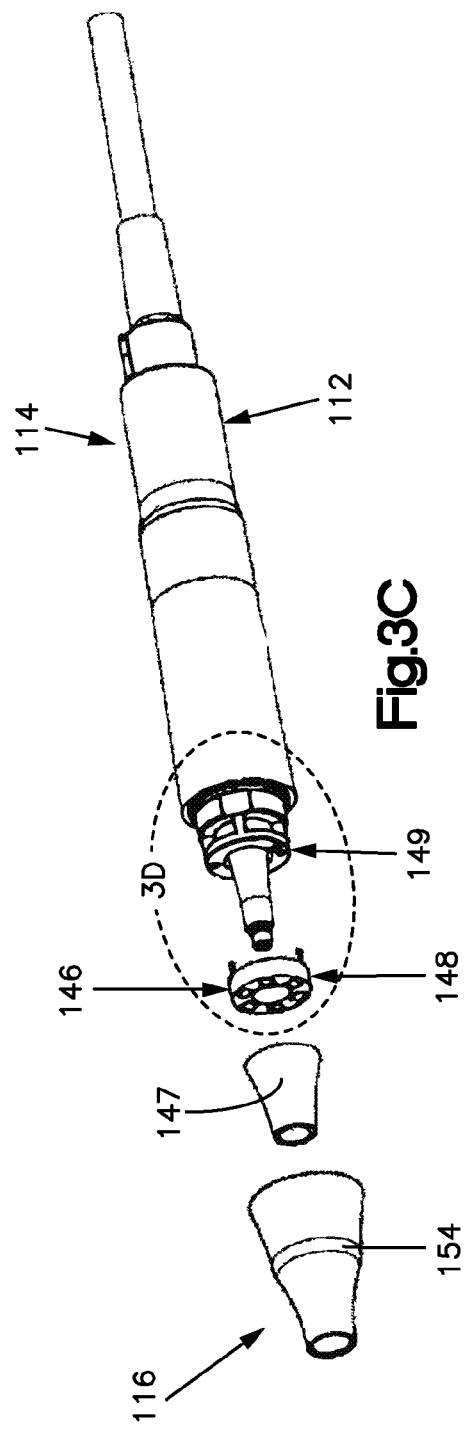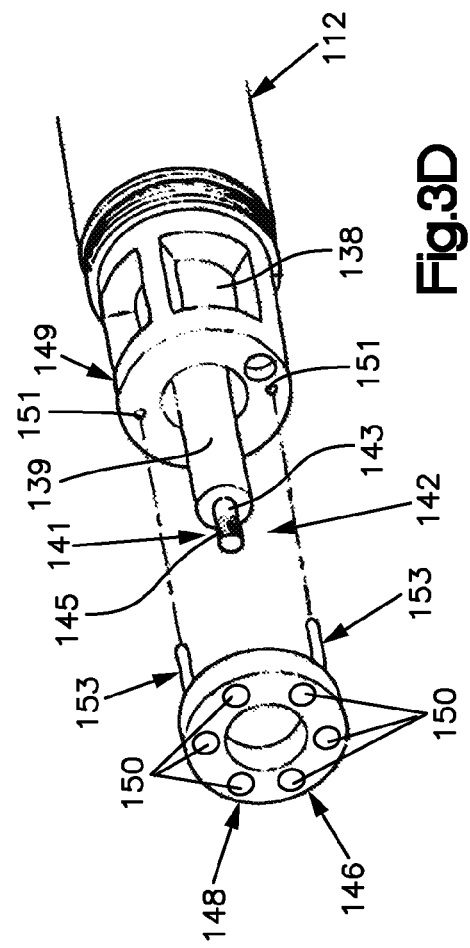

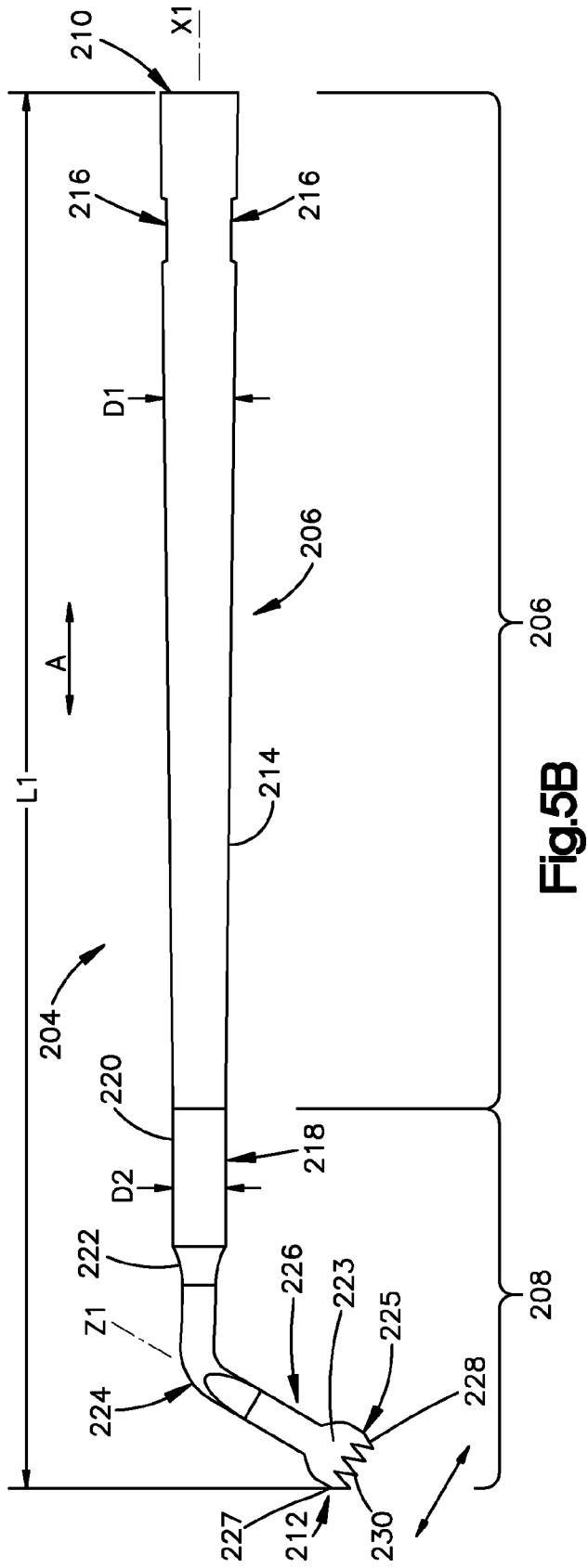
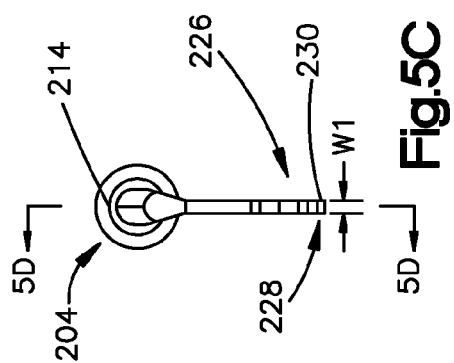
Fig.5B
Fig.5C

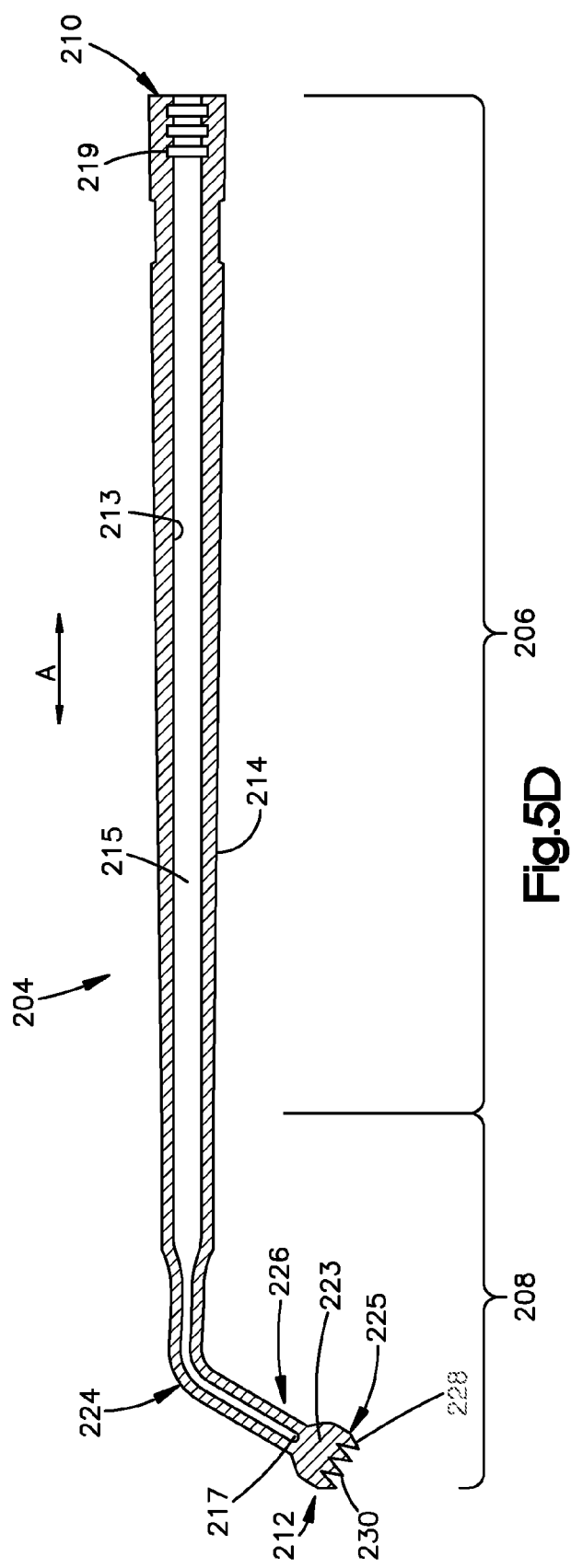

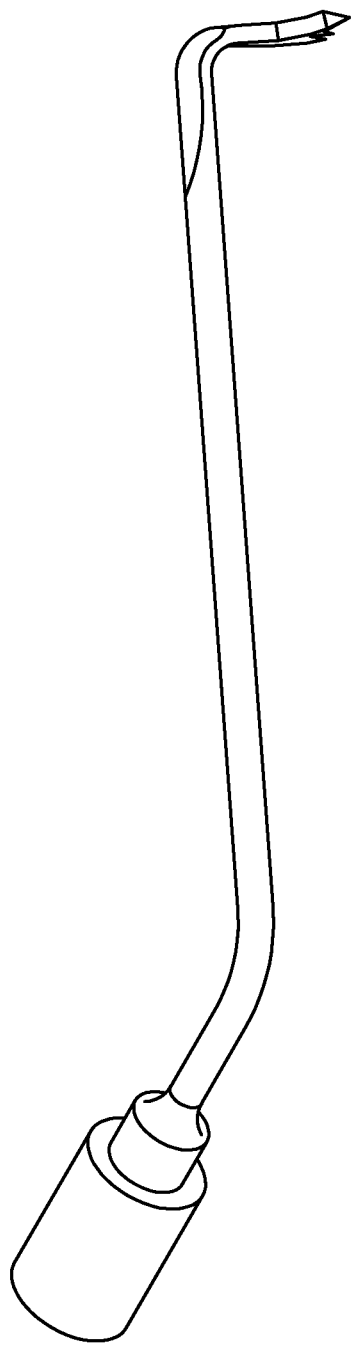

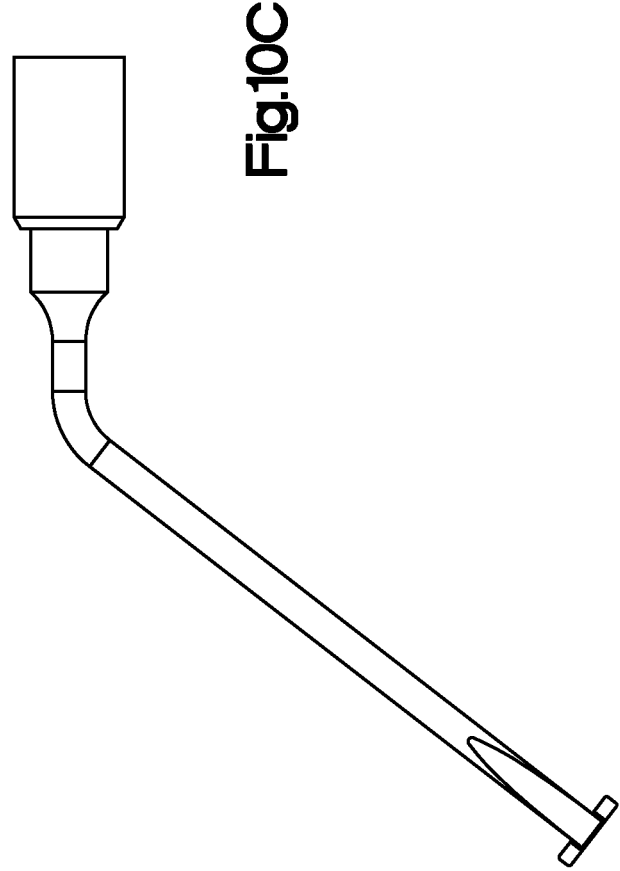

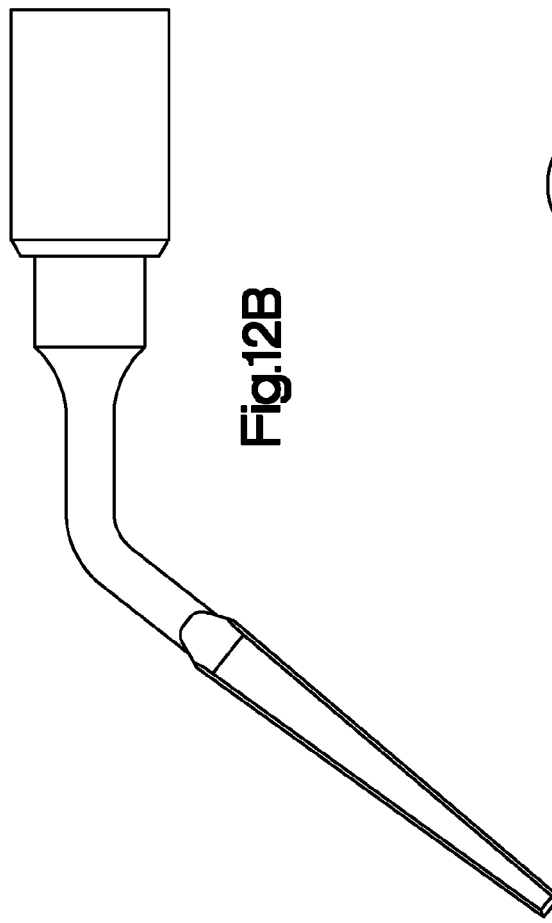
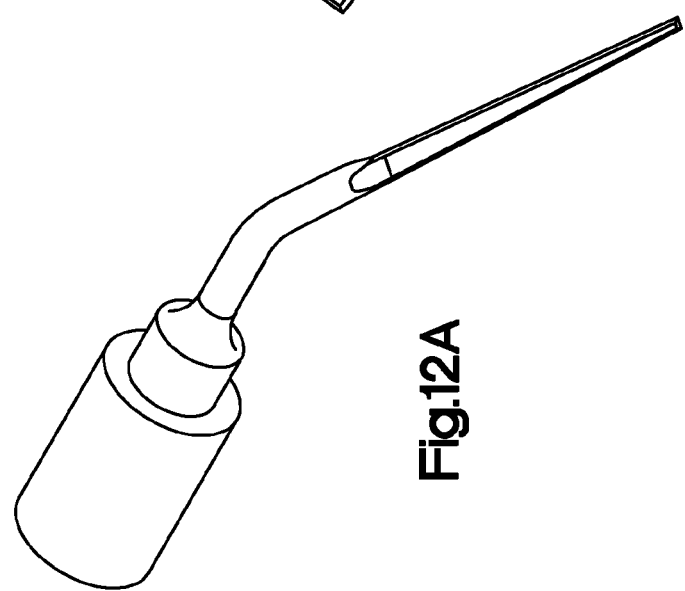

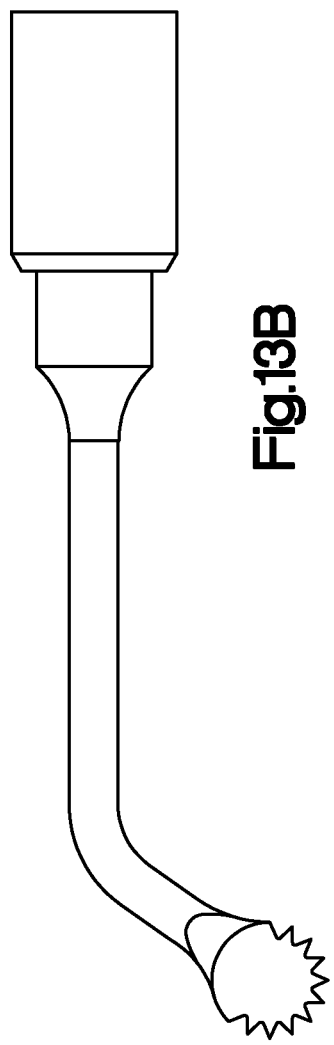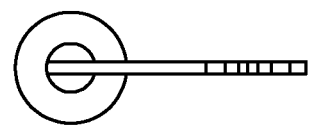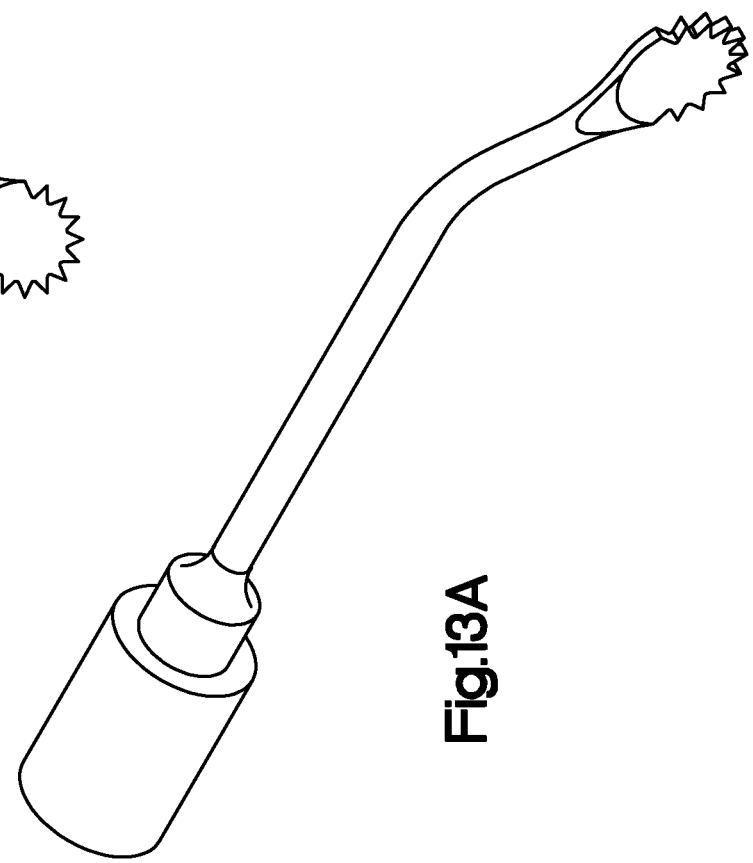

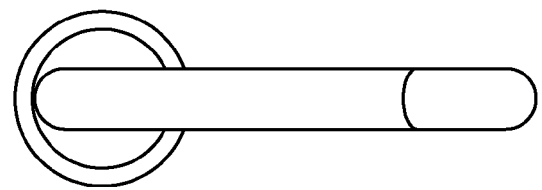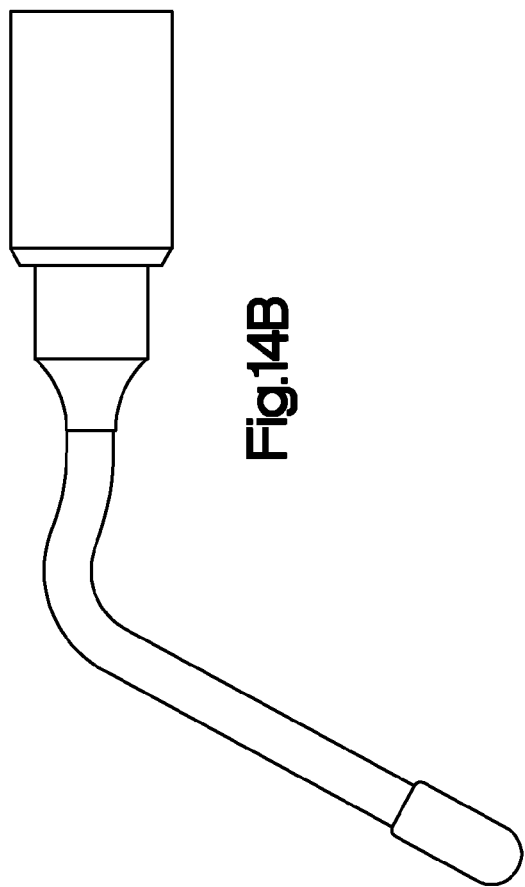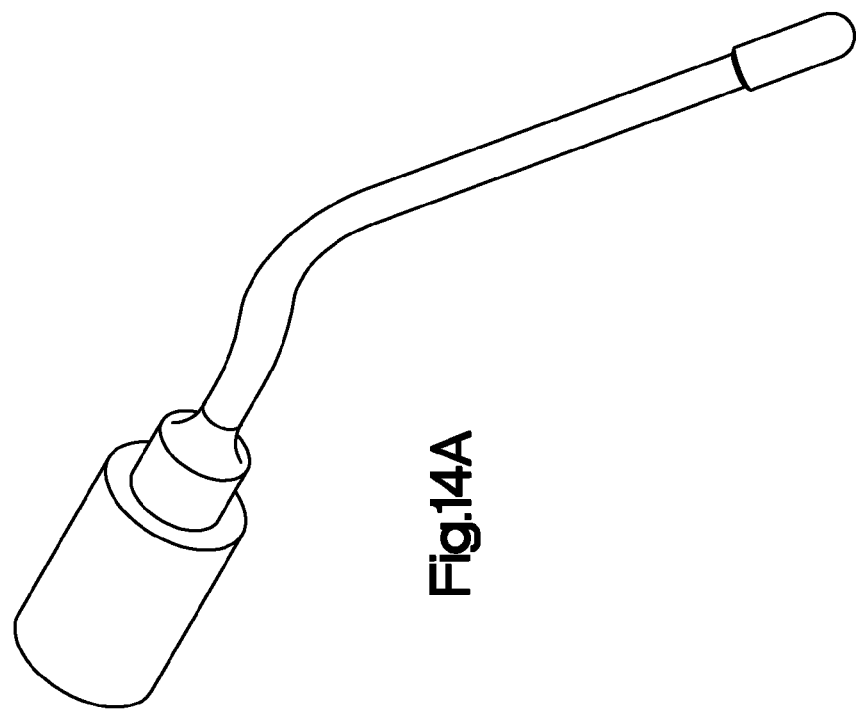

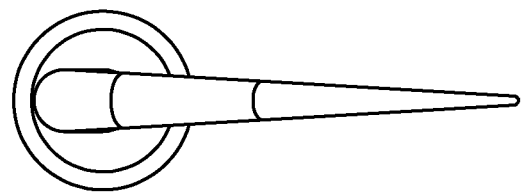
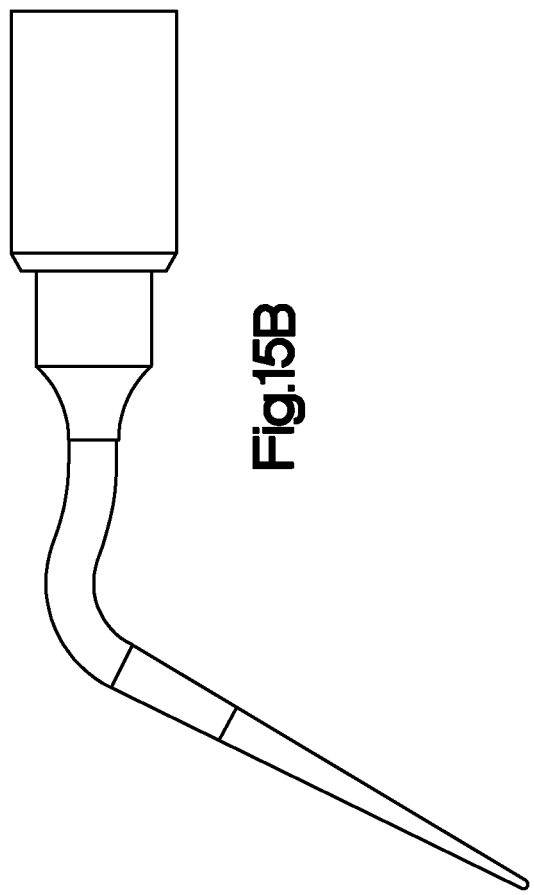
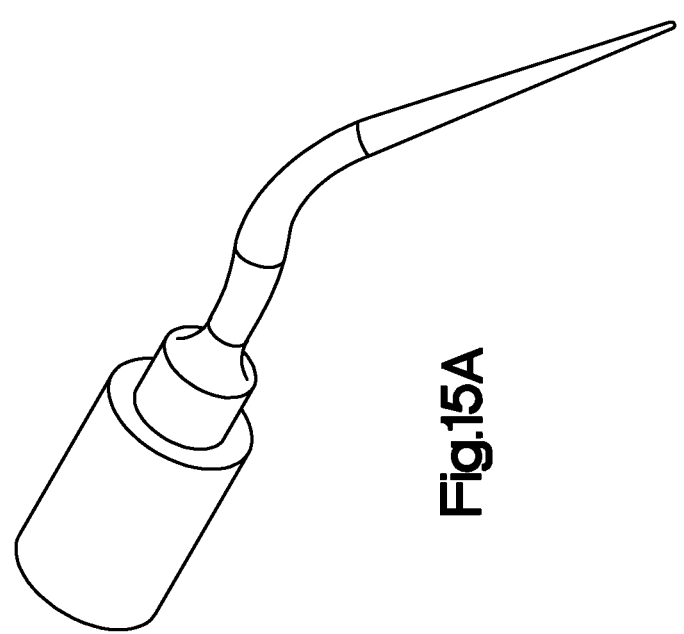

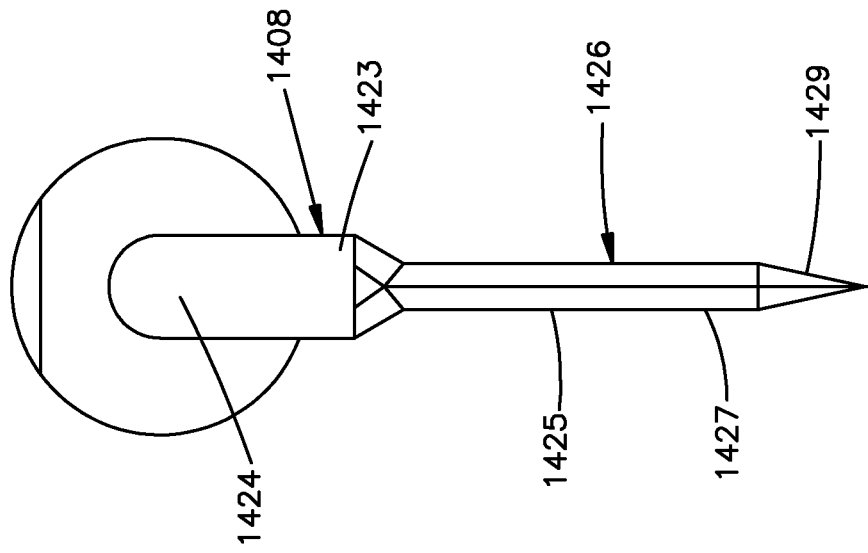
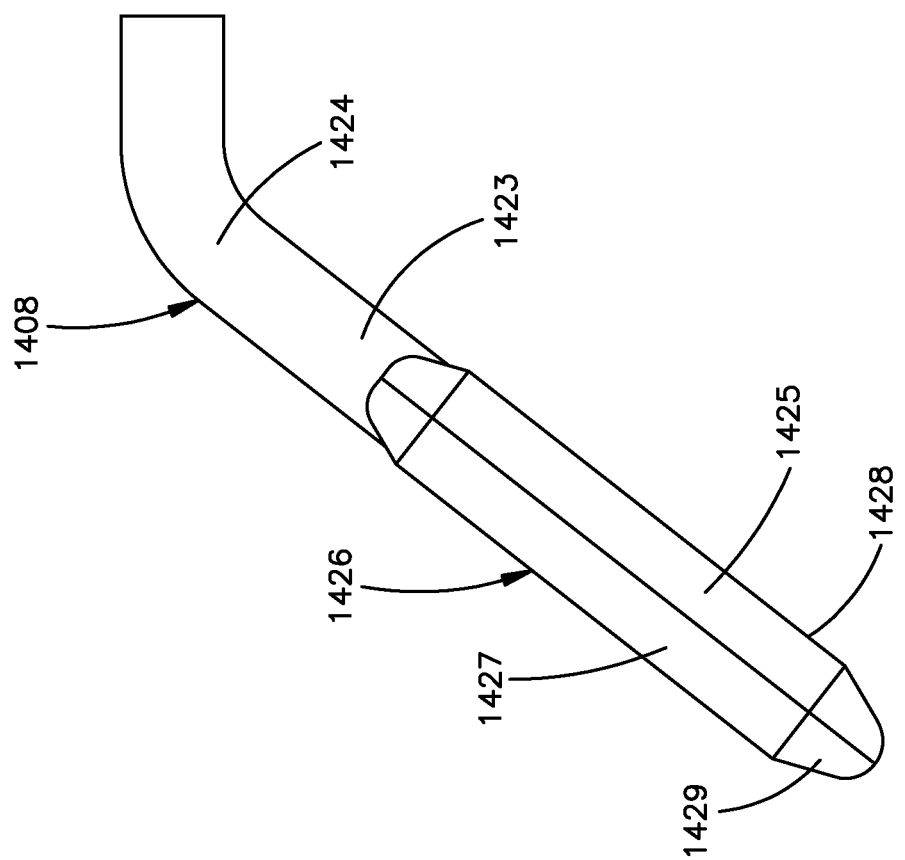

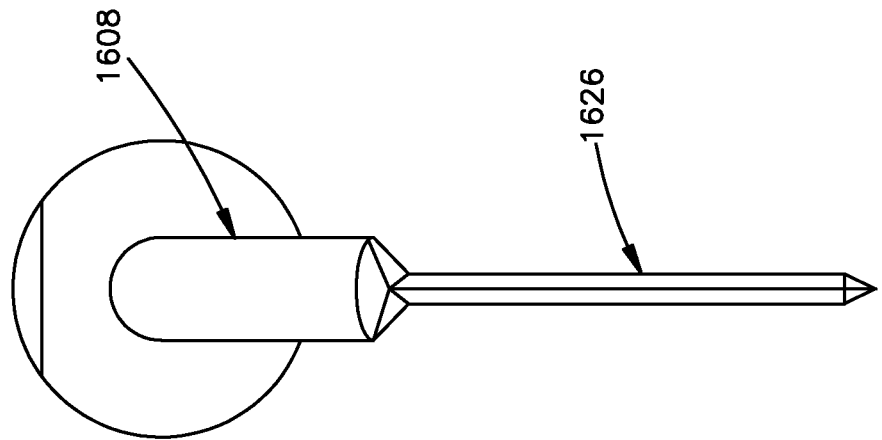
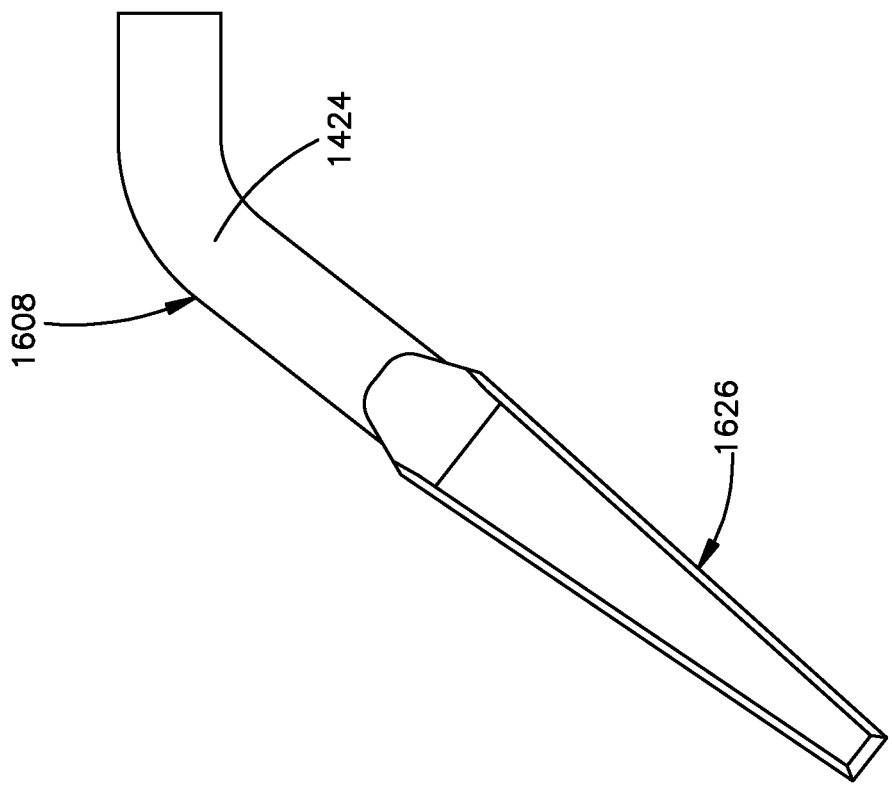

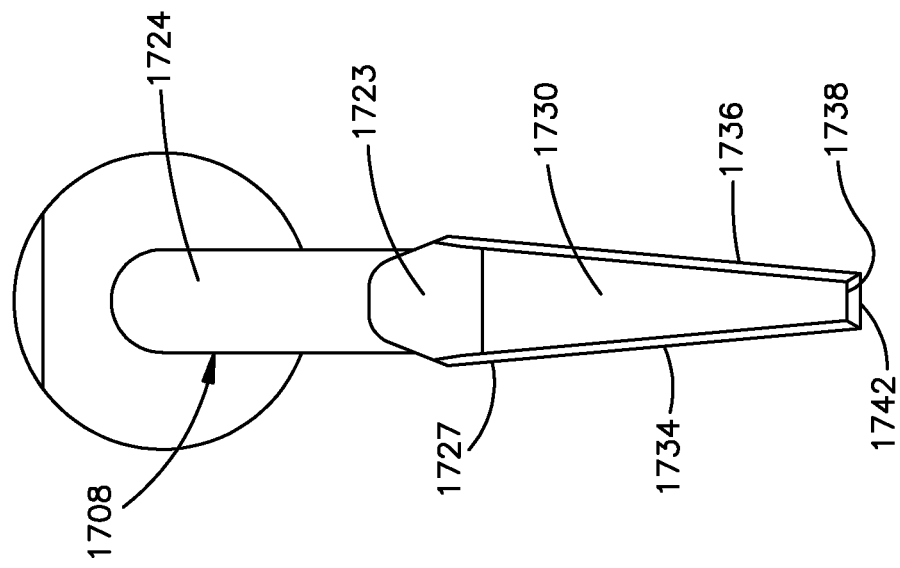
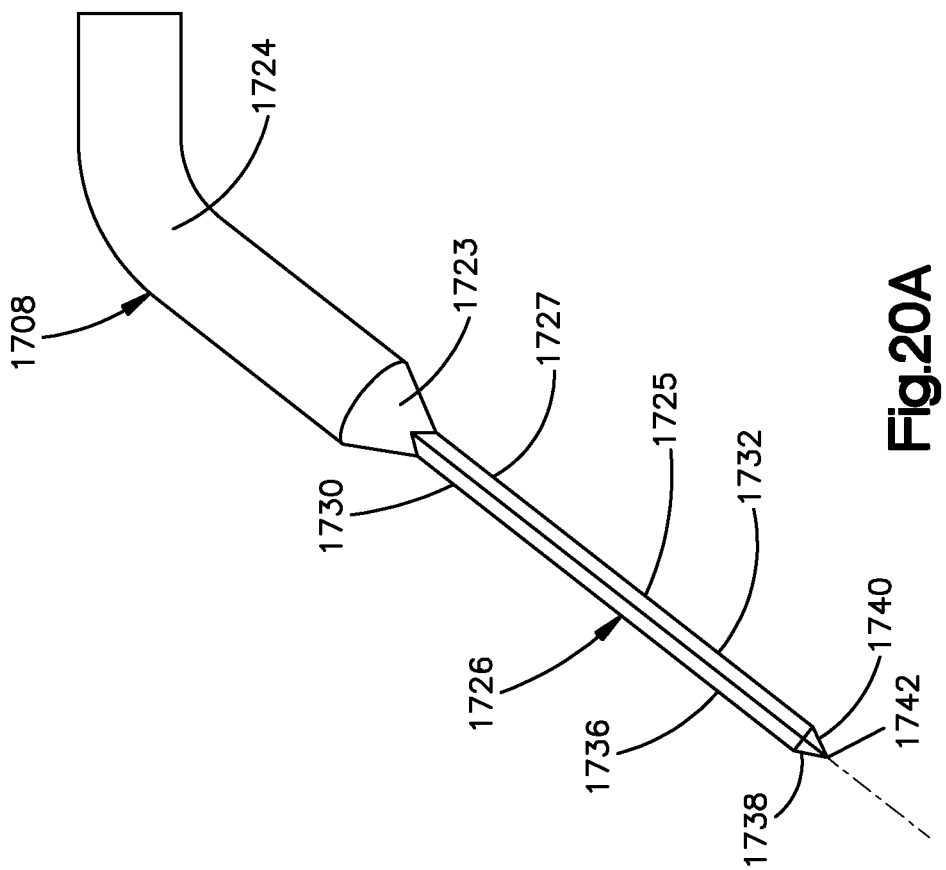

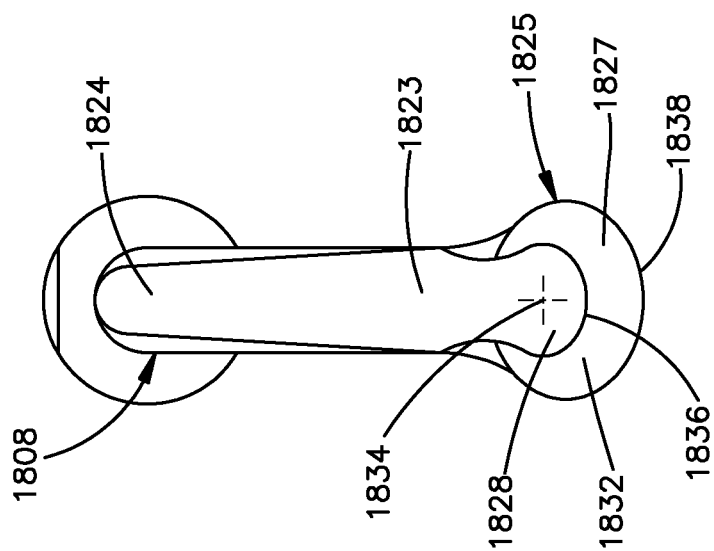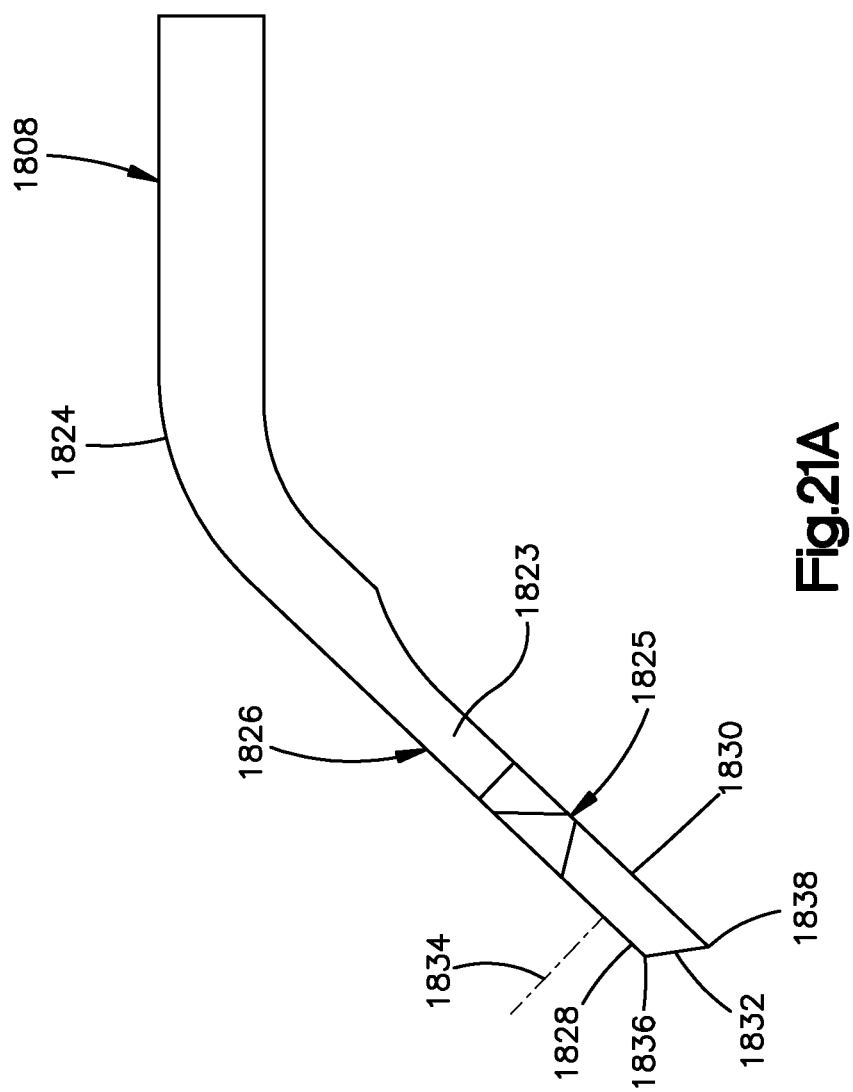

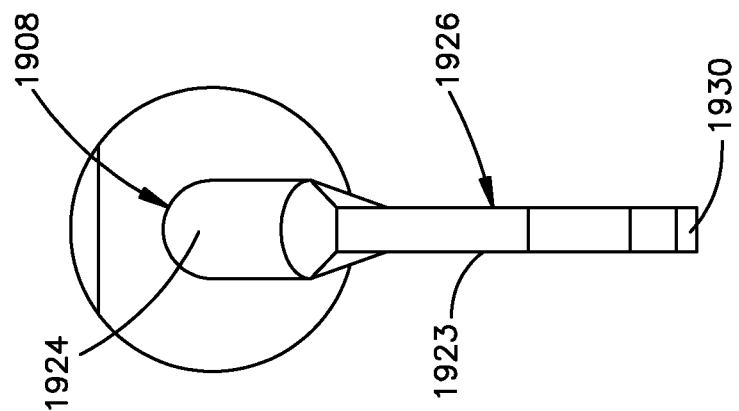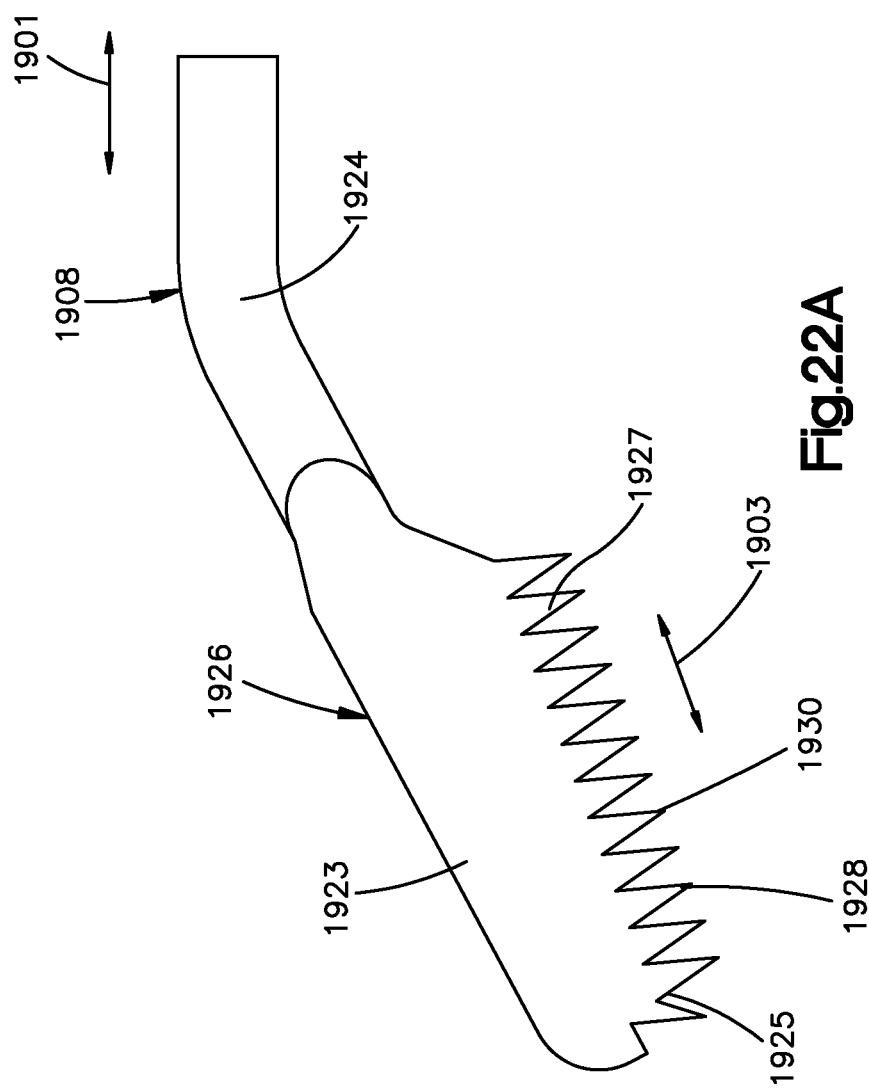

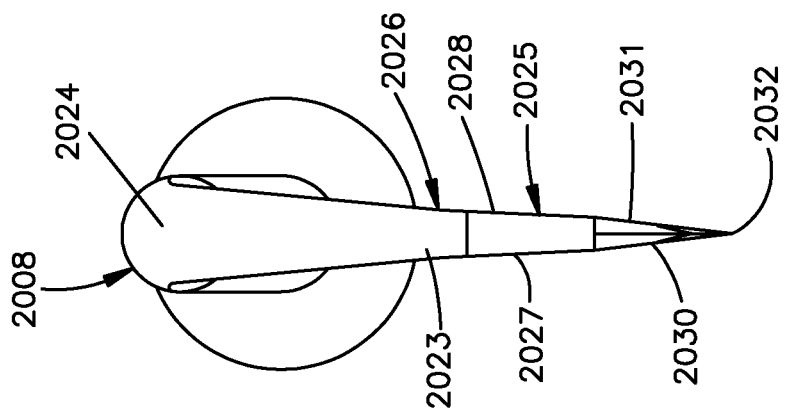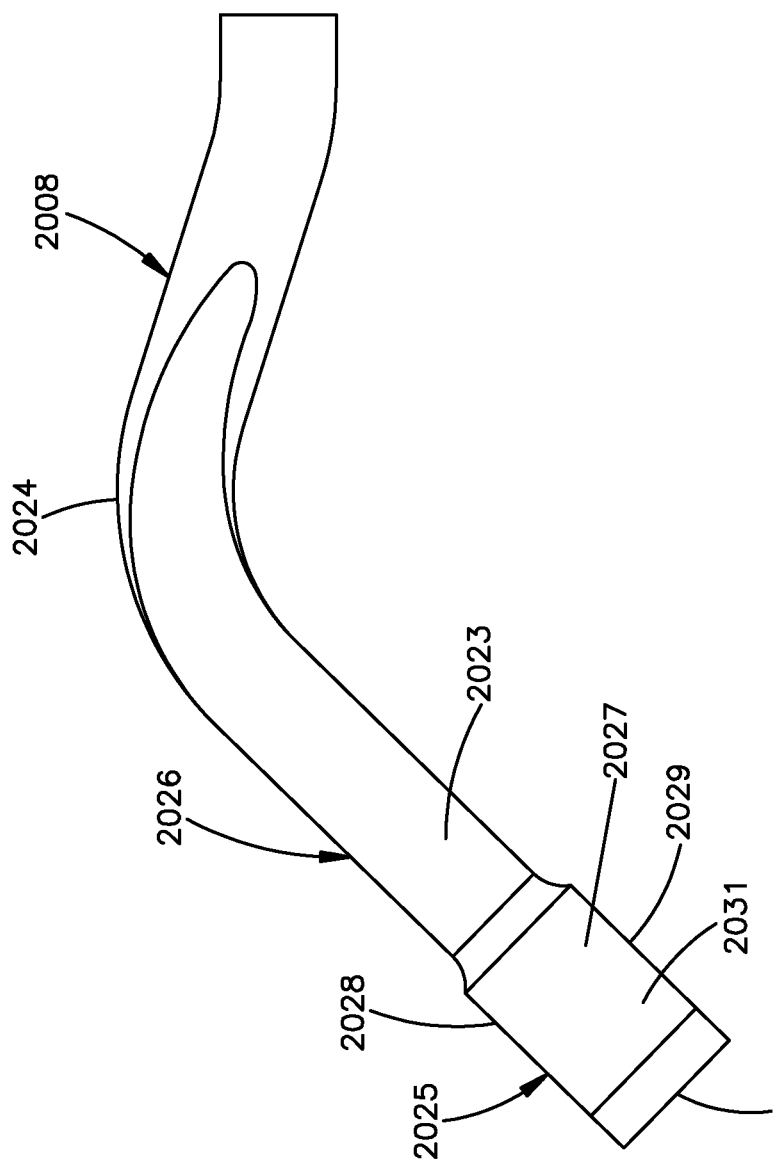

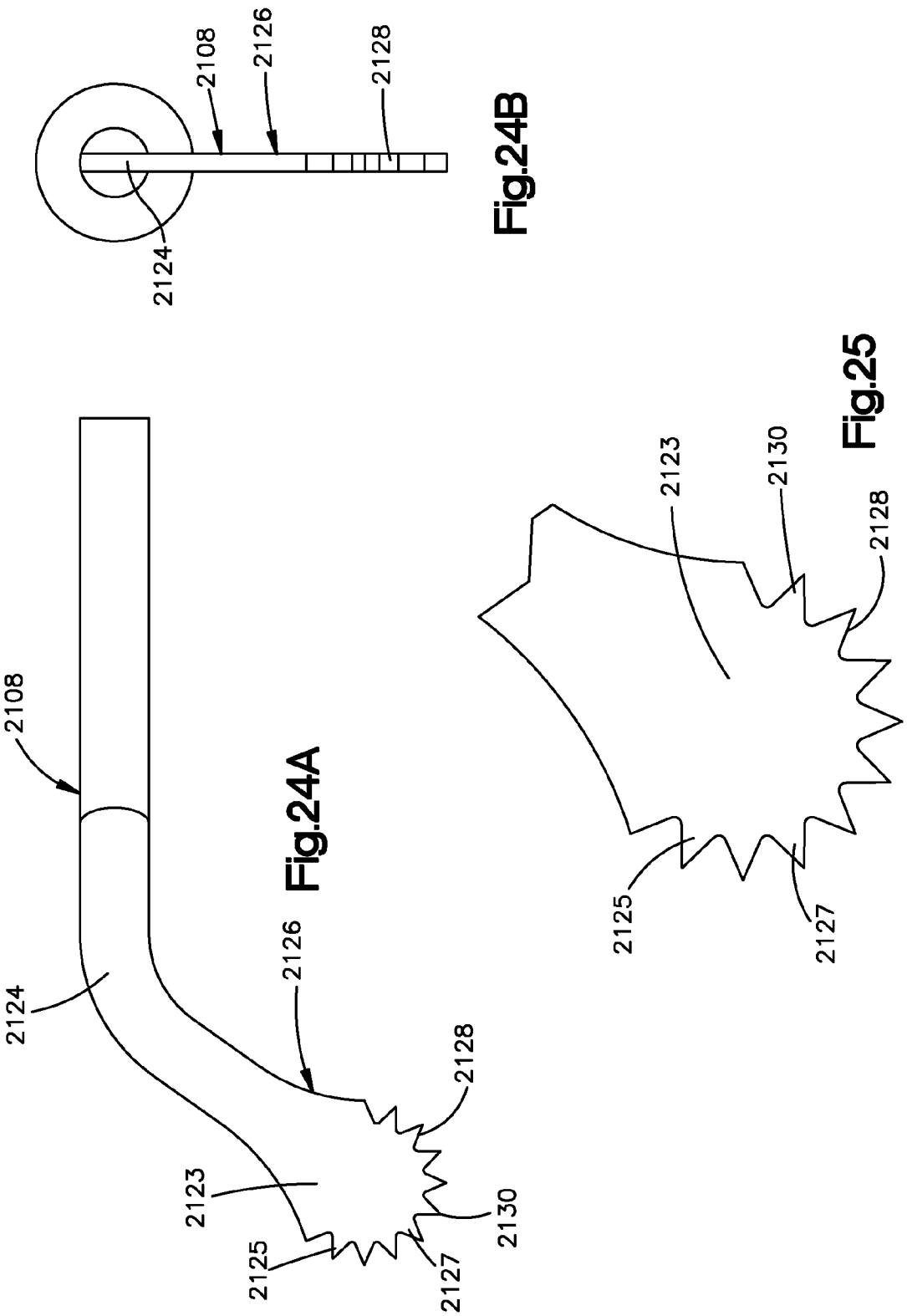

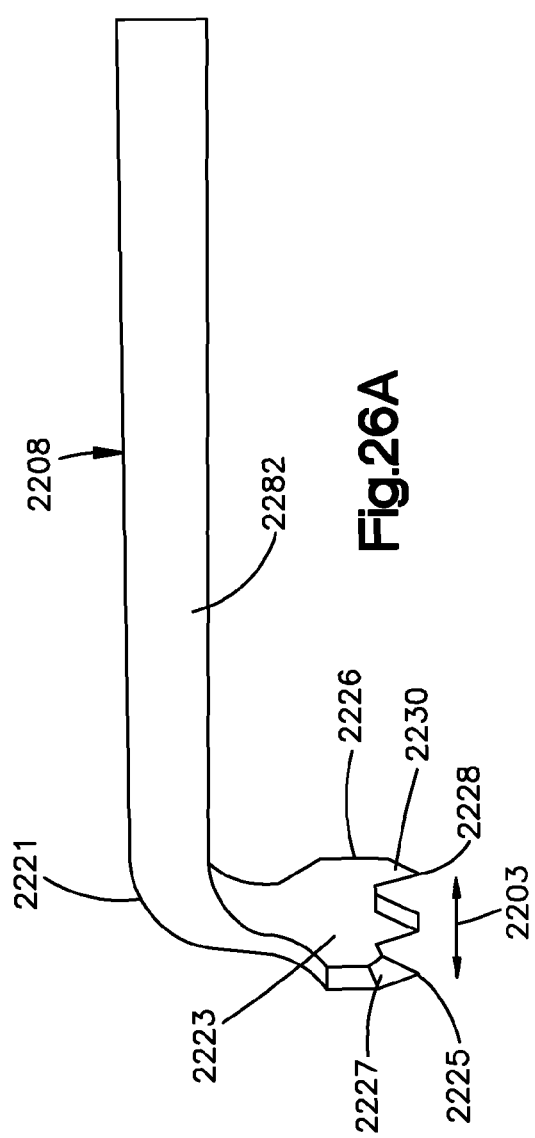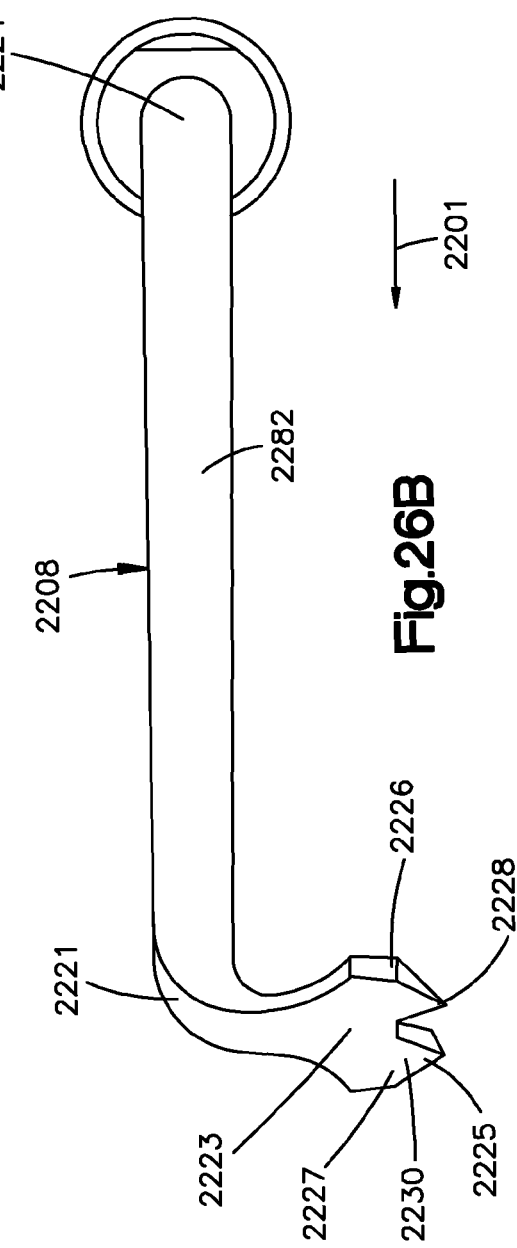

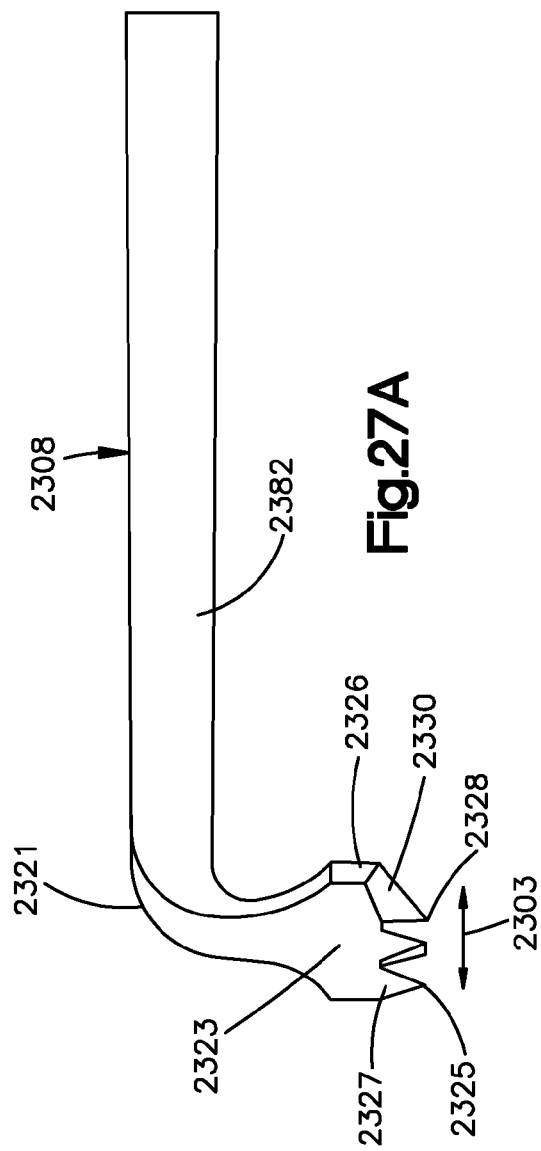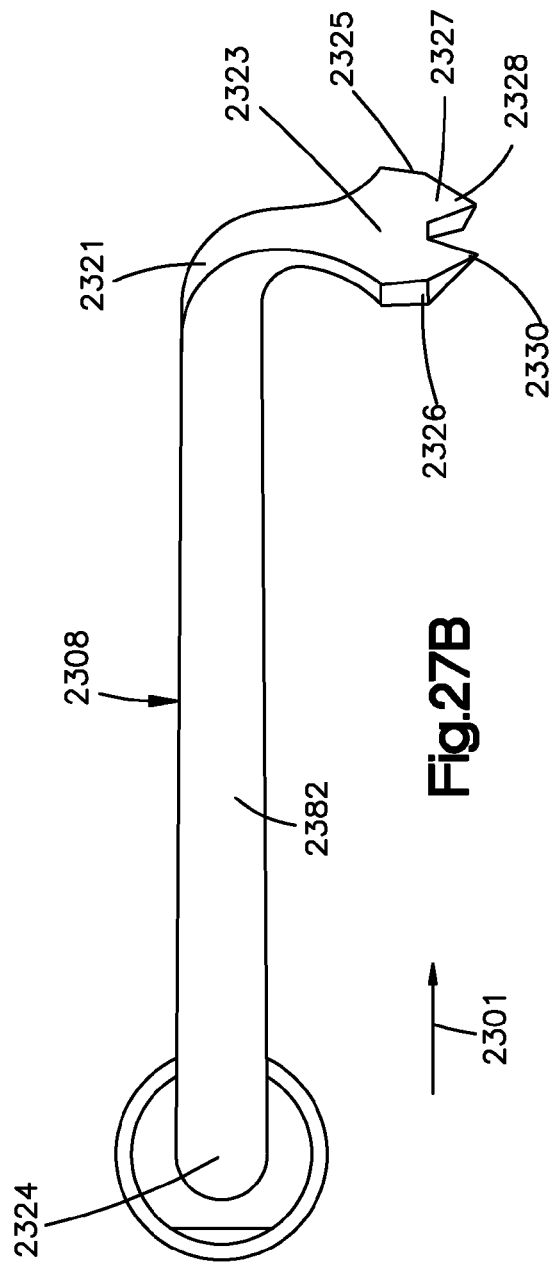

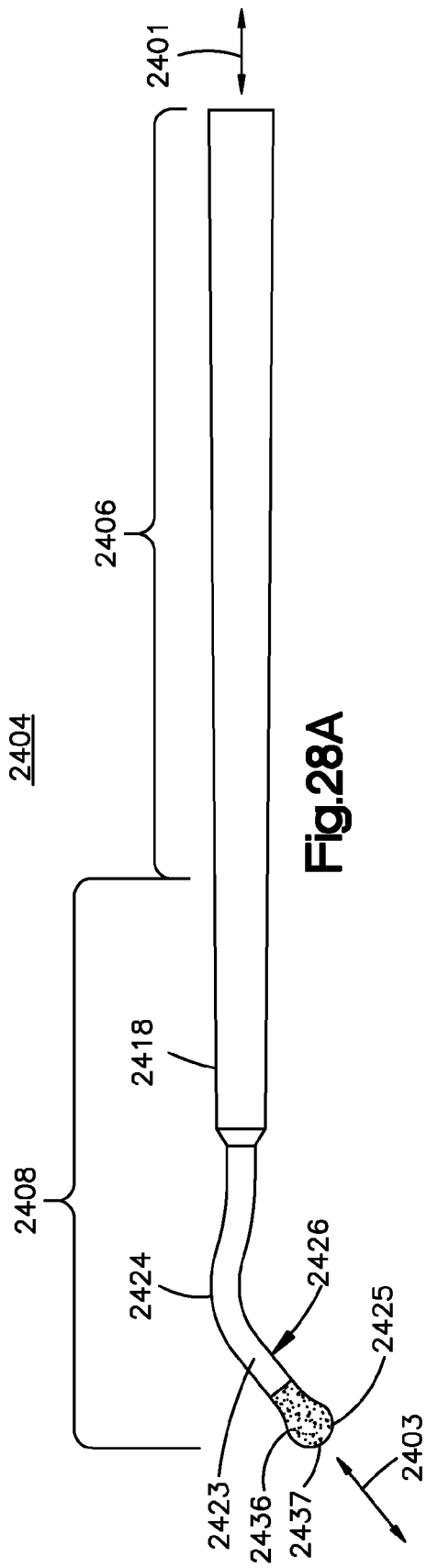
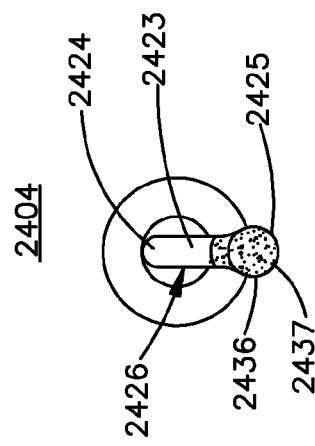
Fig.28A
Fig.28B

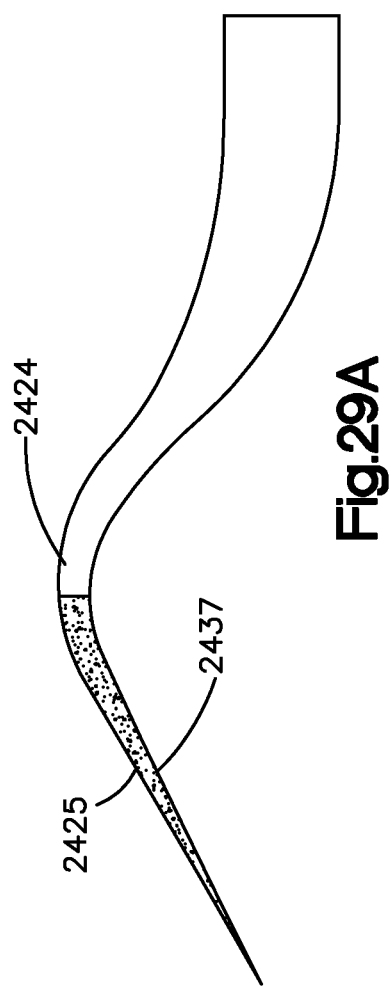
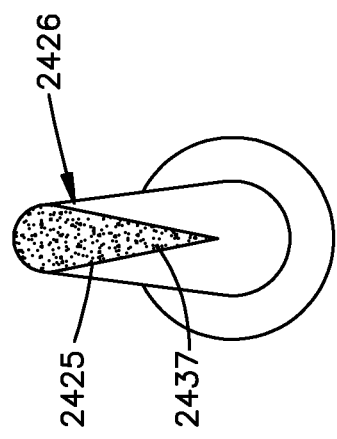

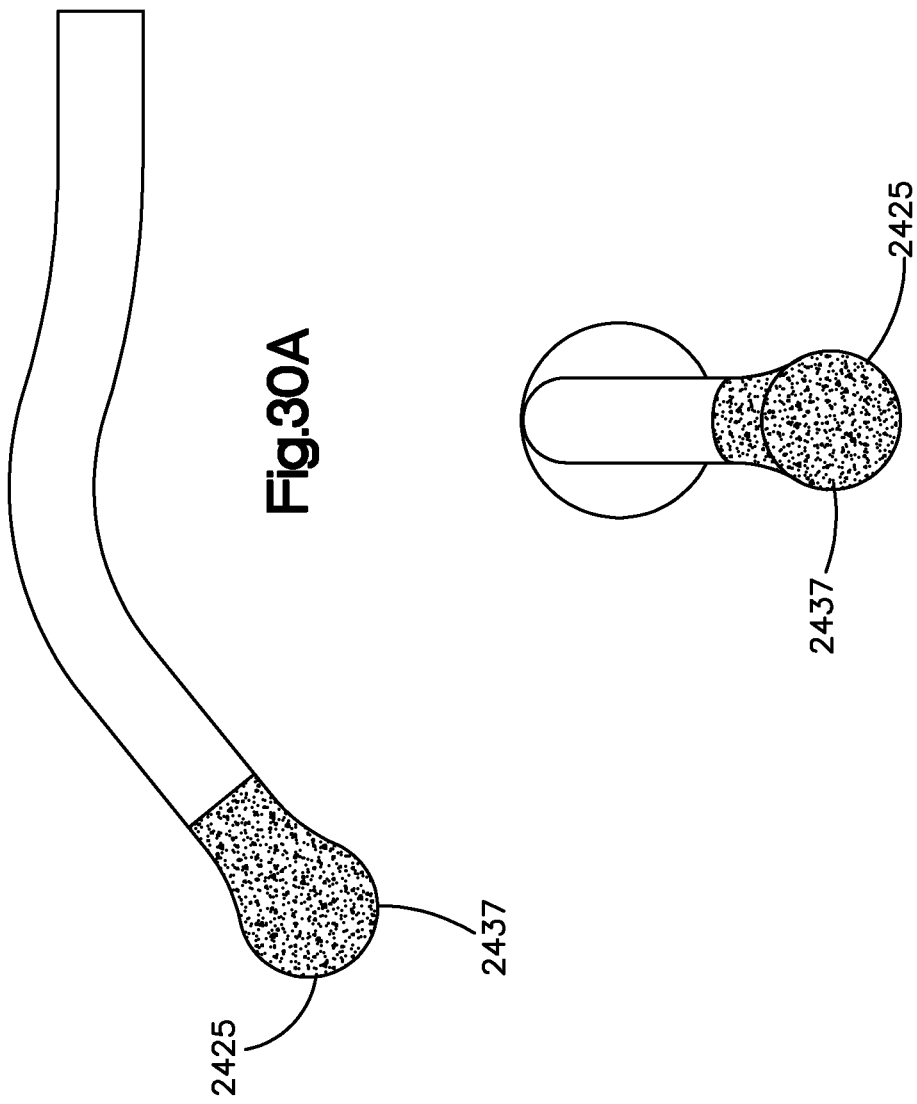

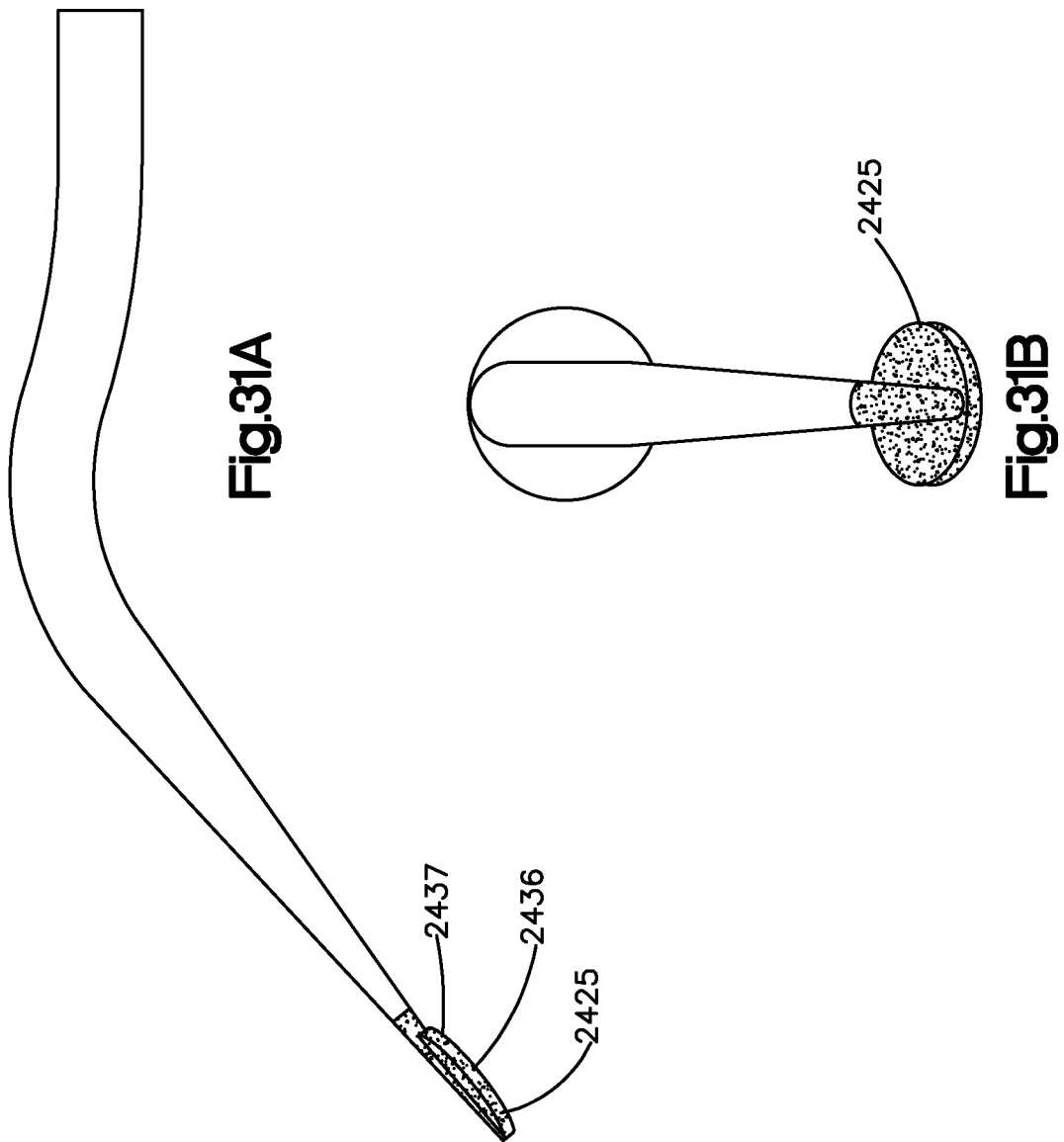

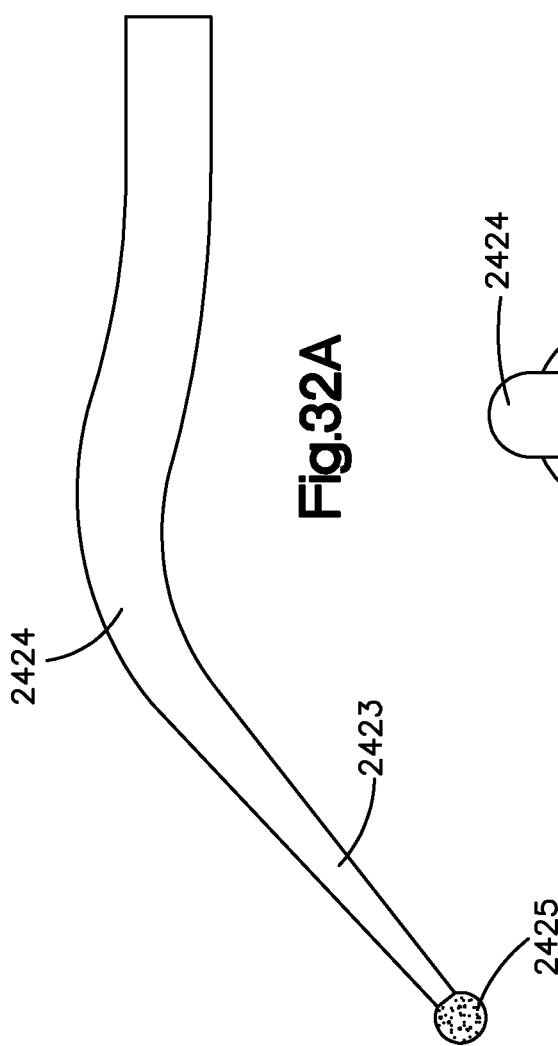
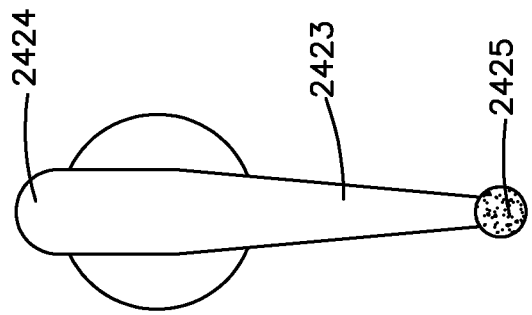

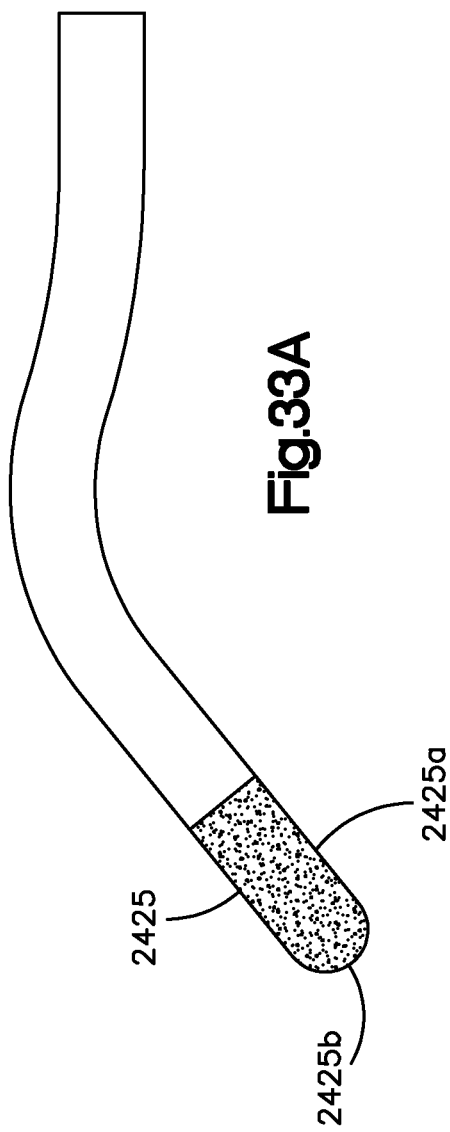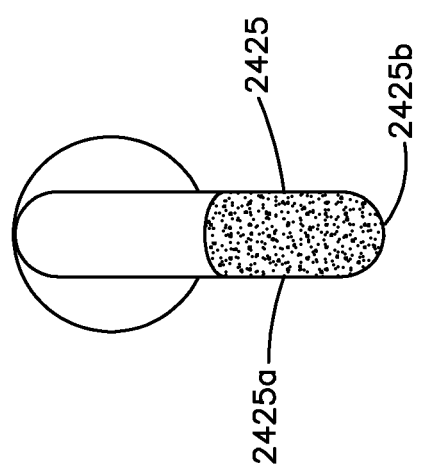

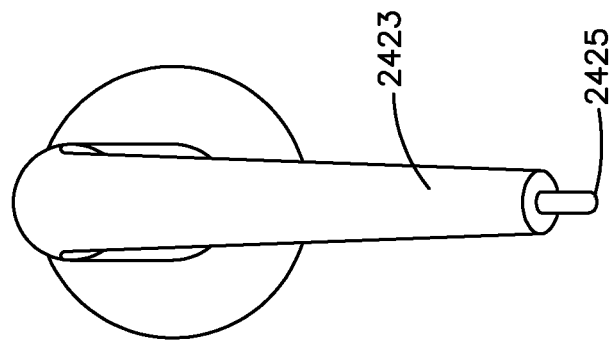

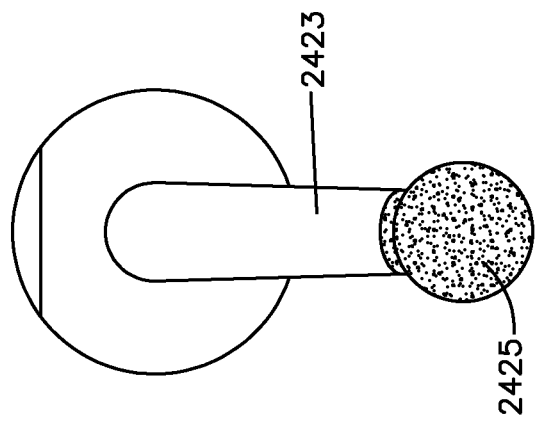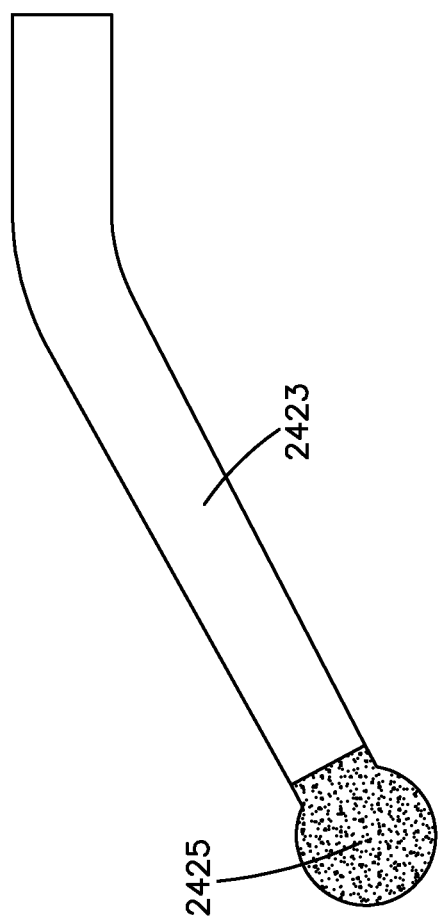

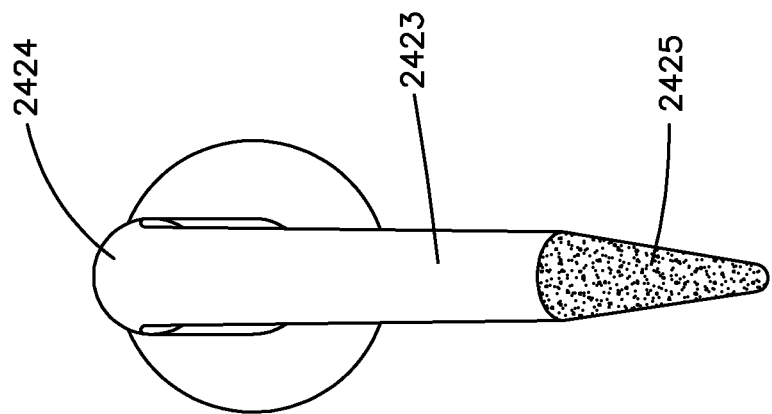
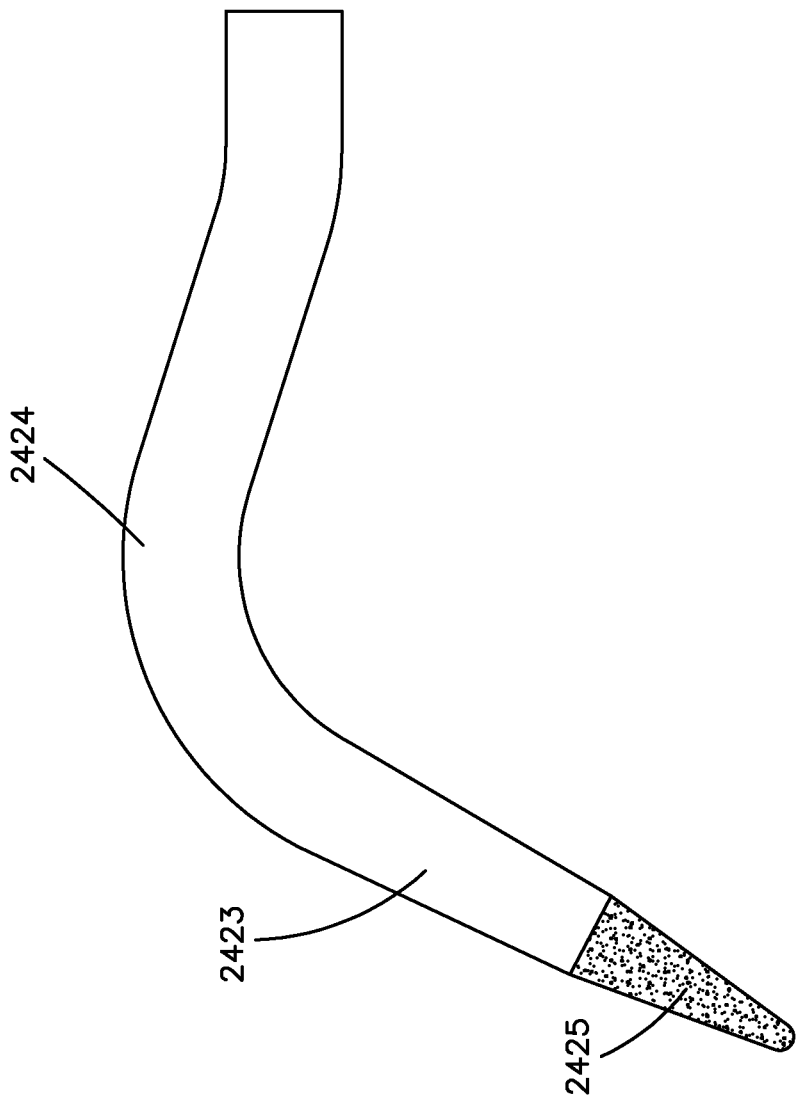
Fig.39B
Fig.39A

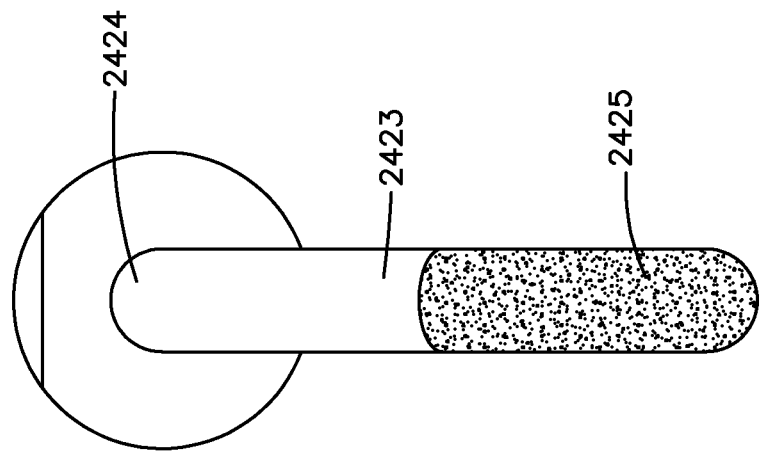
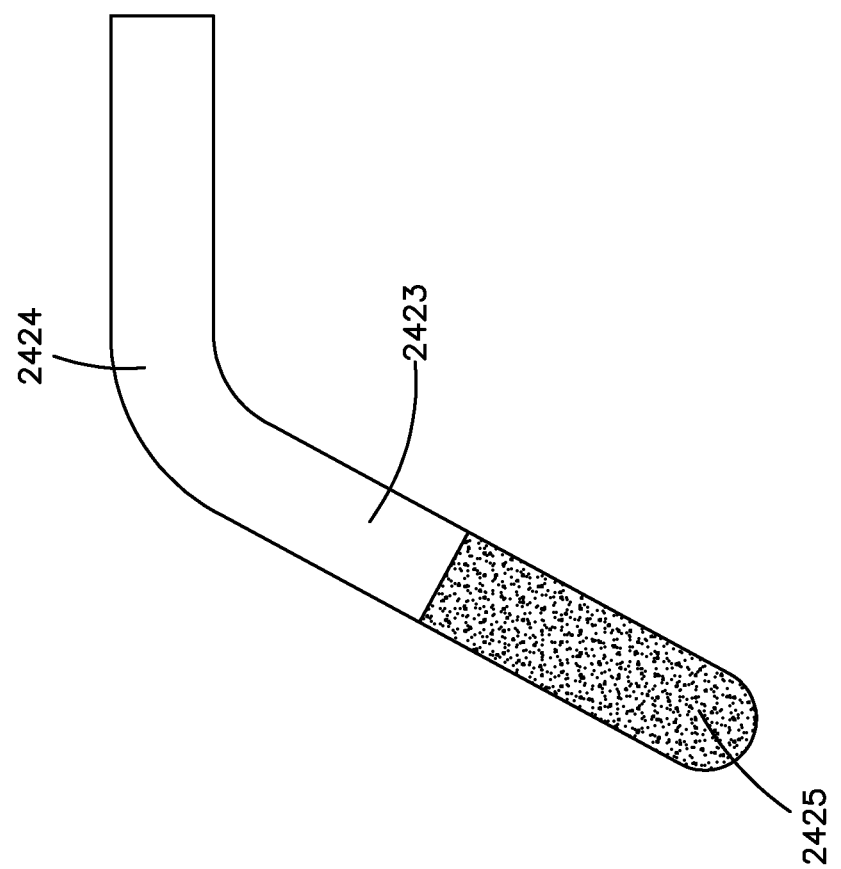

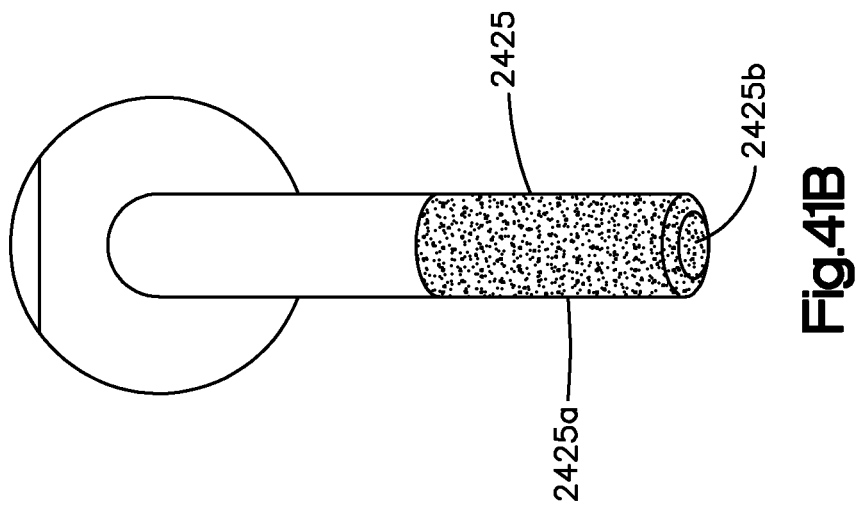
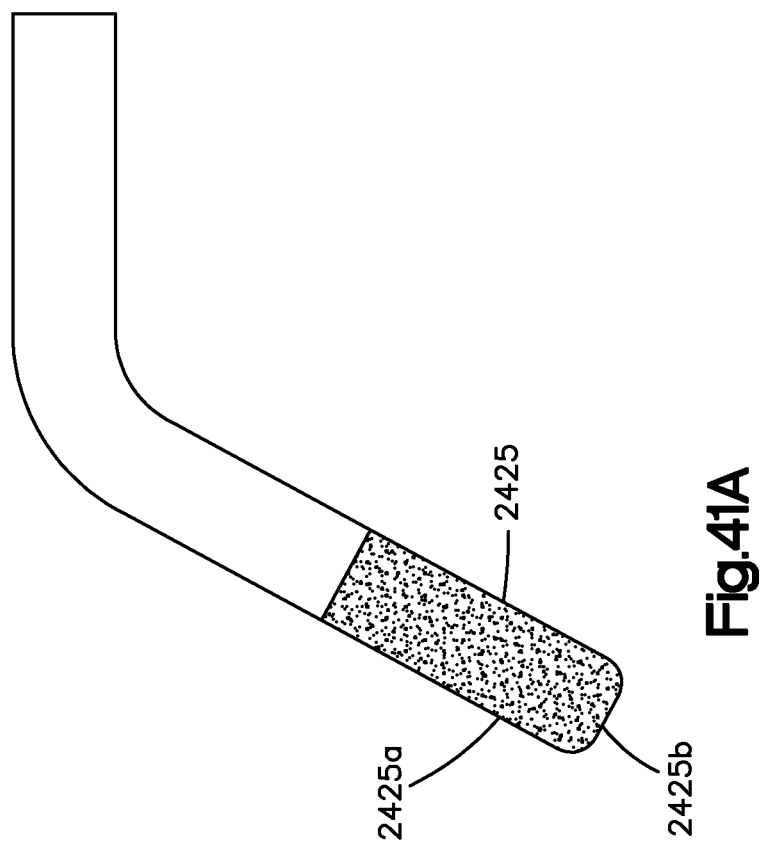

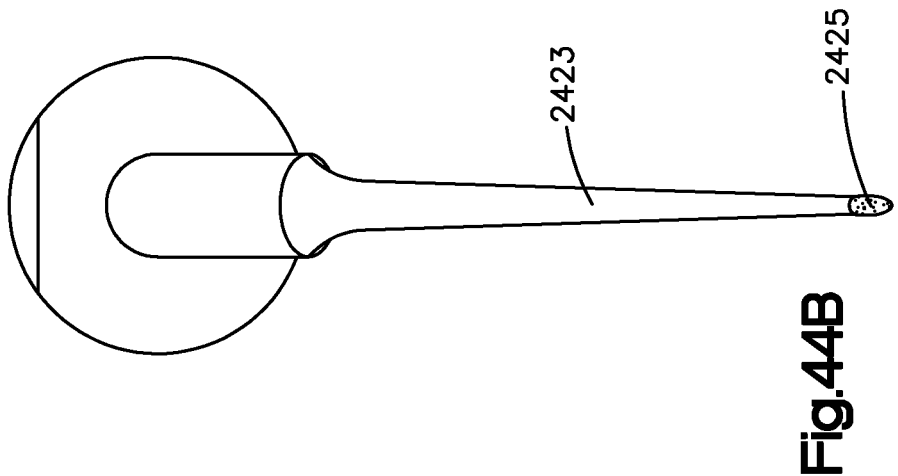
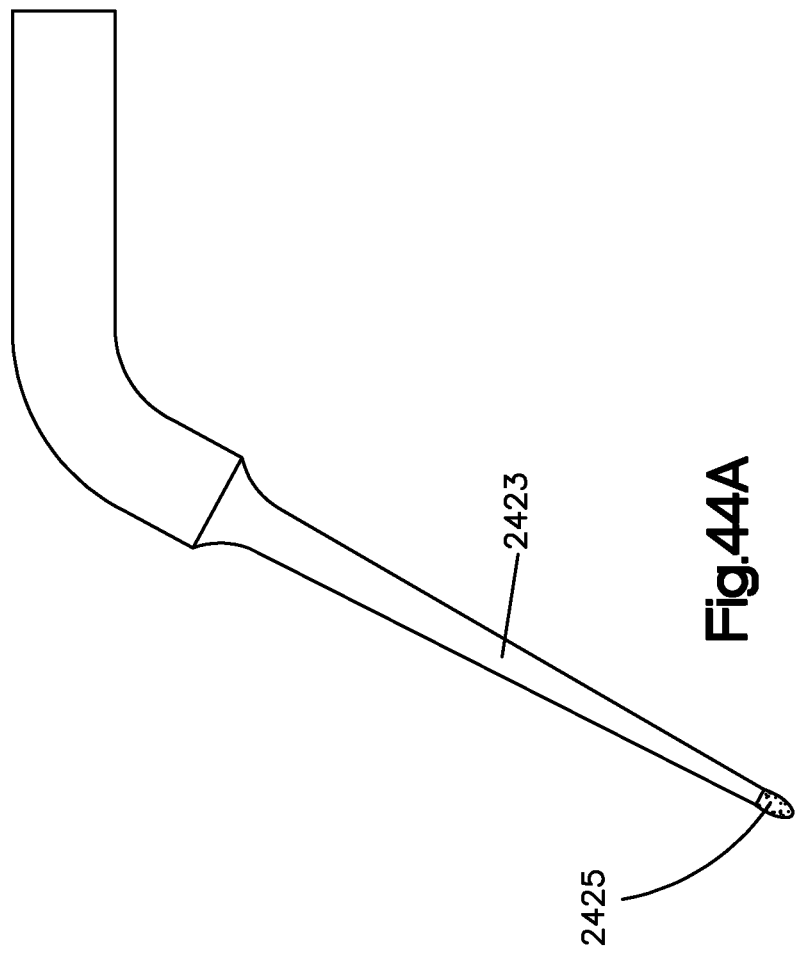
Fig.44B
Fig.44A

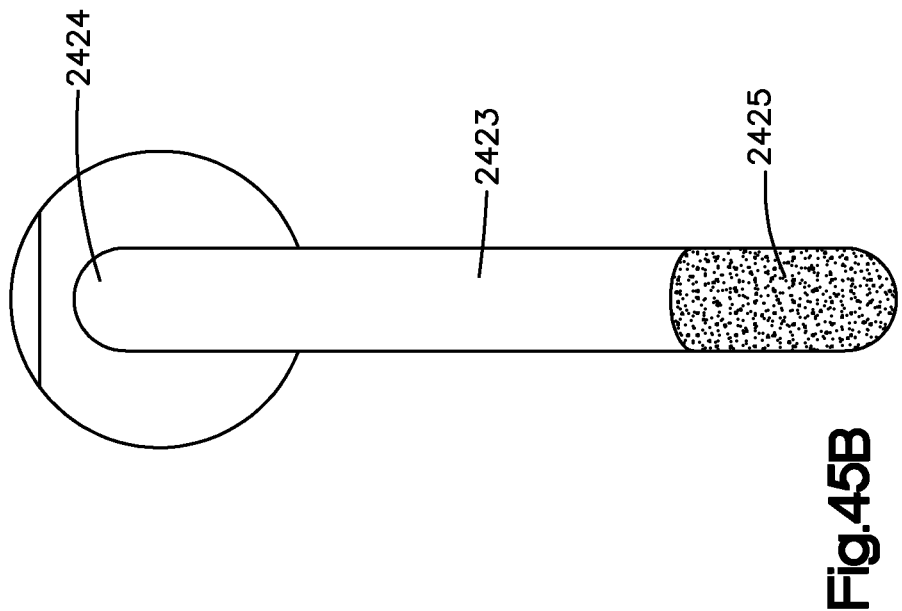
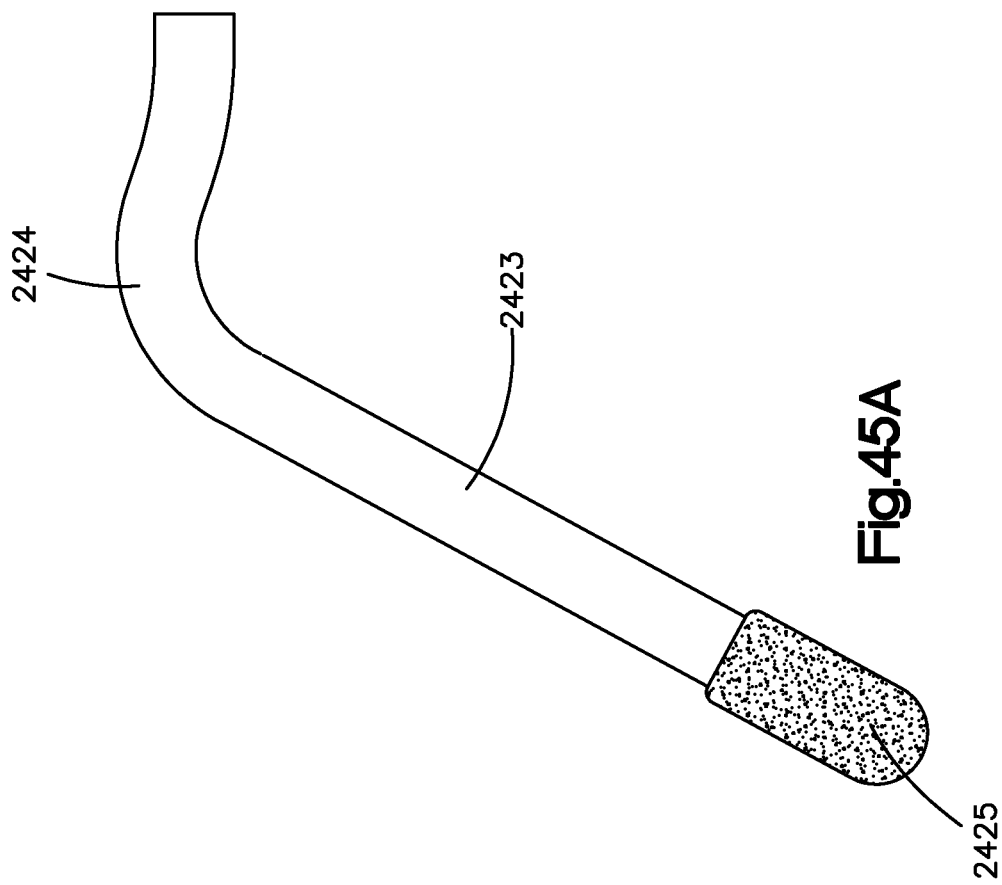
Fig.45B
Fig.45A

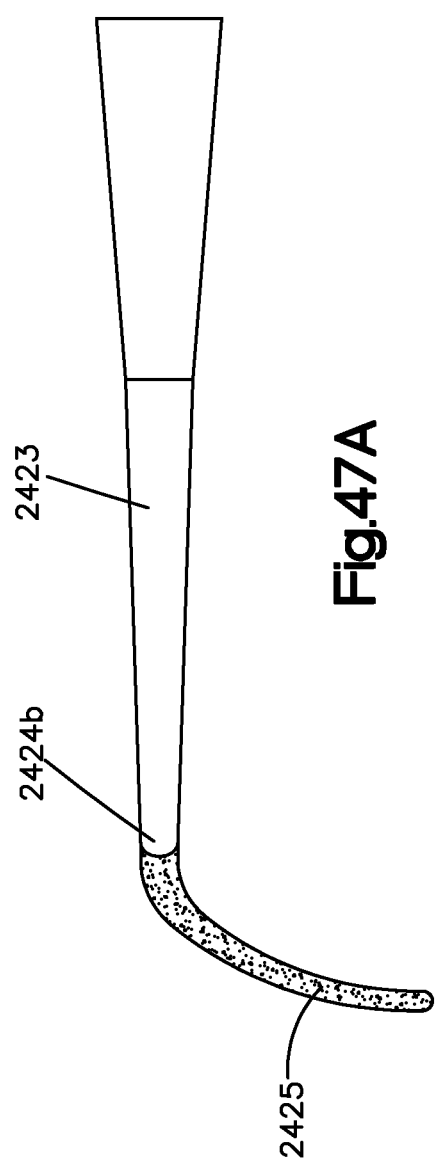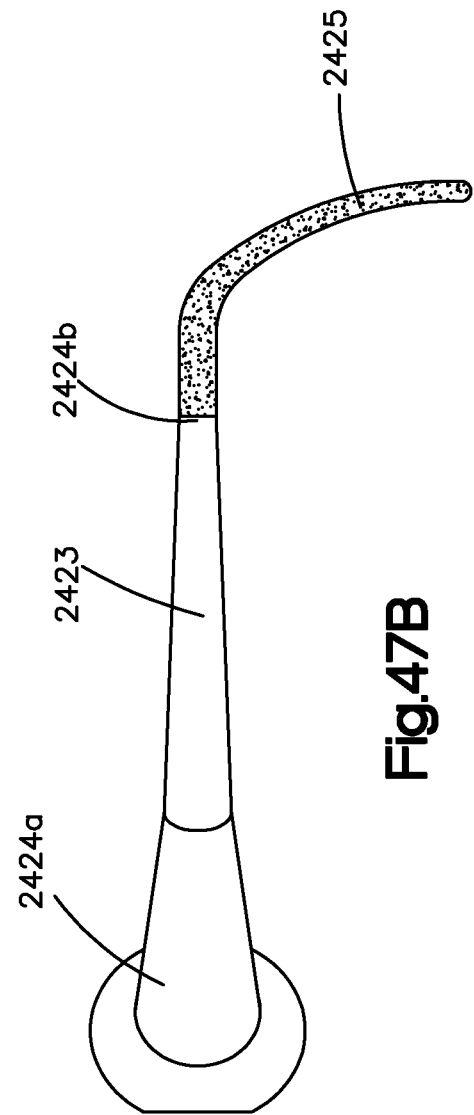
Fig.47A
Fig.47B

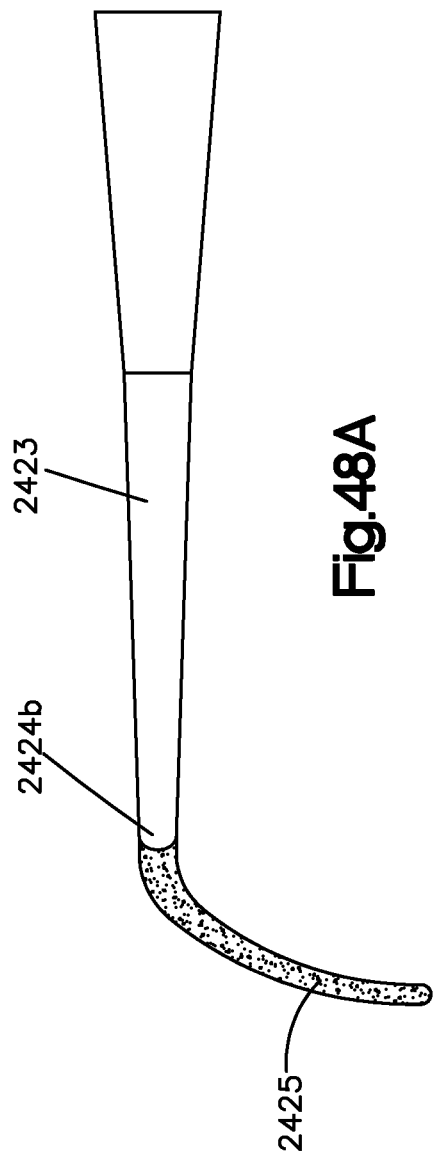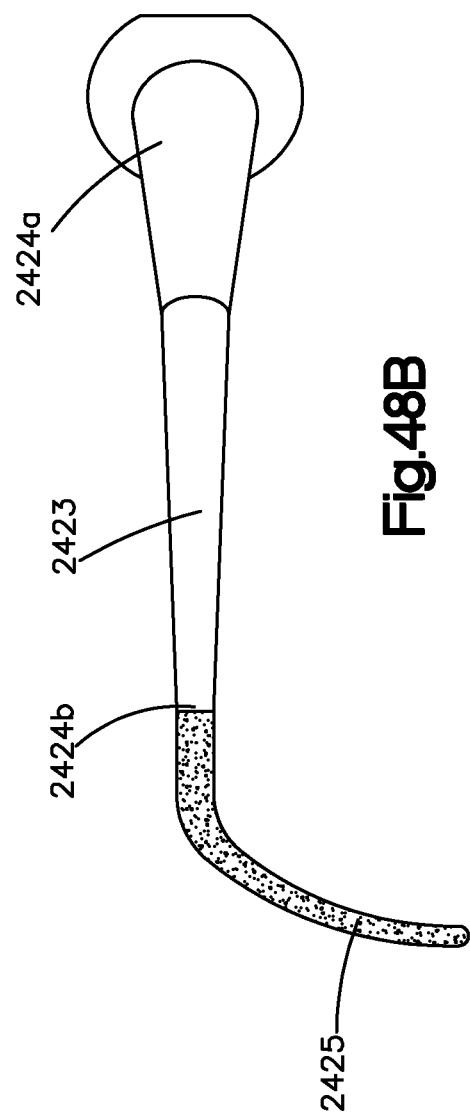

CUTTING TIPS FOR ULTRASONIC SURGICAL SYSTEM

CROSS REFERENCE TO RELATED APPLICATIONS

This application claims the benefit of U.S. Provisional Patent Application Ser. No. 61/594,616 filed Feb. 3, 2012, the contents of which is hereby incorporated by reference in its entirety herein.

FIELD OF THE INVENTION

The present disclosure relates to apparatus, systems, and methods for cutting tissue, and more particularly, to cutting tips for ultrasonic surgical systems.

BACKGROUND

Surgeons currently use, among other things, ultrasonic surgical systems for cutting, removing or shaping tissue or tissue substitutes during a surgical procedure. Ultrasonic surgical systems typically includes a transducer capable of converting electrical energy into mechanical vibrations and a tool mechanically coupled to the transducer. The transducer is conventionally made of a piezoelectric material, and the tool is typically made of stainless steel. The vibrations generated by the transducer travel along the tool until it reaches its tip. The tip of the tool is configured to cut, for instance shape or remove, tissue when it vibrates. Surgeons can contact the target tissue with the vibrating tip of the tool to cut, for instance shape or remove, said tissue.

Conventional tools of ultrasonic surgical systems have relatively short lengths in order to effectively transmit the mechanical vibrations generated by the transducers. It is desirable, however, to develop tools with relatively long lengths in order to allow the surgeon to employ minimally invasive techniques, to reach areas difficult to access and to increase the chances of a safe surgery. It has been found that simply elongating stainless steel may affect the ability of the tool to transmit vibrations effectively. For instance, elongating a stainless steel tool can increase the weight of the tool, which in turn would require additional power to vibrate. This increase in power can in turn overheat the piezoelectric ceramic elements, causing reduced acoustic performance and reliability.

In view of the drawbacks of the conventional tools described above, it desired to develop a tool for an ultrasonic surgical system capable of effectively transmitting vibrations generated by a transducer without comprising acoustic performance and reliability.

SUMMARY

In accordance with one embodiment, a tool can include a first section configured to be coupled to a transducer assembly, and a second section coupled to the first section. The first section at least partially includes a first material. The second section at least partially includes a second material that is different from the first material and denser than the first material. The second section includes a cutting member that is configured to vibrate at a predetermined frequency so as to cut a tissue body an operative portion.

According to an embodiment, the cutting member of the tool is configured to vibrate at a cutting member amplitude that ranges between about 300 percent to about 500 percent of a transducer assembly amplitude of the vibration produced by the transducer assembly when the first section is coupled to the transducer assembly and the transducer assembly is activated.

According to an embodiment, the tool includes a first end and a second end, and defines a length that extends from the first end to the second end in a longitudinal direction. The length of the tool is greater than about 80 millimeters.

According to an embodiment, the length of the tool ranges between about 20 millimeters and about 120 millimeters.

According to an embodiment, the length of the tool is about 105.7 millimeters.

According to an embodiment, the first material is a titanium alloy.

According to an embodiment, the second material is stainless steel.

According to an embodiment, the first section is elongated along a first axis, and the second section includes an elbow, such that at least a portion of the second section is elongated along a second axis. The second axis is oriented at an oblique angle with respect to the first axis.

According to an embodiment, the cutting member could include a serrated edge, a scalpel-like end, diamond ball end, or scraper.

According to an embodiment, the second section further comprises a support body, and the cutting member further comprises teeth that protrude outward from the support body.

According to an embodiment, the cutting member has a substantially spherical shape.

According to an embodiment, the cutting member defines at least one cutting surface, and further comprises a coating that covers at least a portion of the at least one cutting surface.

According to an embodiment, the abrasive material could be diamond particles.

According to an embodiment, the abrasive material includes diamond-like carbons.

According to an embodiment, the cutting member has a substantially frusto-conical shape.

According to an embodiment, the cutting member is substantially shaped as a scalpel.

In accordance with an embodiment, a cutting system that is configured to cut a tissue body includes a transducer assembly and a tool. The transducer assembly is configured to receive electrical energy and convert the received electrical energy to mechanical vibration at a predetermined frequency. The tool is coupled to the transducer assembly such that mechanical vibrations produced by the transducer assembly are transmitted to the tool thereby causing the tool to vibrate at the predetermined frequency. The tool includes a first section and a second section. The first section is coupled to the transducer assembly. The first section at least partially includes a first material. The second section is coupled to the first section, and at least partially includes a second material that is different from the first material and denser than the first material. The second section includes an operative portion that includes a cutting member configured to cut the tissue body when the cutting member vibrates.

According to an embodiment, the cutting member of the system is configured to vibrate at a cutting member amplitude that ranges between about 300 percent to about 500 percent of a transducer assembly amplitude of the vibration produced by the transducer assembly when the first section is coupled to the transducer assembly and the transducer assembly is activated.

According to an embodiment, the system further includes a power supply electrically coupled to the transducer assembly. The power supply is configured to supply electrical energy to the transducer assembly.

According to an embodiment, the system further includes a controller electrically coupled to the transducer assembly. The controller is configured to control electrically energy supplied to the transducer assembly.

According to an embodiment, the tool includes a first end and a second end, and defines a length that extends from the first end to the second end in a longitudinal direction. The length of the tool is greater than about 80 millimeters.

According to an embodiment, the length of the tool ranges between about 20 millimeters and about 120 millimeters.

According to an embodiment, the length of the tool is about 105.7 millimeters.

According to an embodiment, the first material is a titanium alloy.

According to an embodiment, the titanium alloy is a Ti6-Al 4-V alloy.

According to an embodiment, the second material is stainless steel.

According to an embodiment, the first section is elongated along a first axis, and the second section includes an elbow, such that at least a portion of the second section is elongated along a second axis. The second axis is oriented at an oblique angle with respect to the first axis.

According to an embodiment, the cutting member defines a serrated edge.

According to an embodiment, the second section includes a support body, and the cutting member includes teeth that protrude outwardly from the support body.

According to an embodiment, the cutting member has a substantially spherical shape.

According to an embodiment, the cutting member defines at least one cutting surface, and further includes an abrasive coating that covers at least a portion of the at least one cutting surface. The abrasive coating is at least made from an abrasive material.

According to an embodiment, the abrasive material includes diamond particles.

According to an embodiment, the abrasive material includes diamond-like carbons.

According to an embodiment, the cutting member has a substantially frusto-conical shape.

According to an embodiment, the cutting member is substantially shaped as a scalpel.

BRIEF DESCRIPTION OF THE DRAWINGS

The foregoing summary, as well as the following detailed description of a preferred embodiment, are better understood when read in conjunction with the appended diagrammatic drawings. For the purpose of illustrating the present disclosure, reference to the drawings is made. The scope of the disclosure is not limited, however, to the specific instrumentalities disclosed in the drawings. In the drawings:

FIG. 3A is a side elevation view of a transducer assembly of the ultrasonic surgical system represented in FIG. 1;

FIG. 3B is a side sectional view of the transducer assembly of FIG. 3A, showing the some internal components;

FIG. 3C is a perspective exploded view of the transducer assembly of FIG. 3A;

FIG. 3D is an enlarged perspective exploded view of region 3D of the transducer assembly as shown in FIG. 3C;

FIG. 5B is a side elevation view of the tool illustrated in FIG. 5A;

FIG. 5C is a front elevation view of the tool illustrated in FIG. 5C;

FIG. 5D is a cross-sectional side view of the tool illustrated in FIG. 5A, taken along section line 5D-5D of FIG. 5C;

FIGS. 10A-16 illustrate schematics of a tool in accordance with various alternate embodiments of the present disclosure;

FIG. 17A is a side elevation view of a second section of a tool in accordance with an embodiment of the present disclosure;

FIG. 17B is a front elevation view of the second section shown in FIG. 17A;

FIG. 19A is a side elevation view of a second section of a tool in accordance with an embodiment of the present disclosure;

FIG. 19B is a front elevation view of the second section shown in FIG. 19A;

FIG. 20A is a side elevation view of a second section of a tool in accordance with an embodiment of the present disclosure;

FIG. 20B is a front elevation view of the second section shown in FIG. 20A;

FIG. 21A is a side elevation view of a second section of a tool in accordance with an embodiment of the present disclosure;

FIG. 21B is a front elevation view of the second section shown in FIG. 21A;

FIG. 22A is a side elevation view of a second section of a tool in accordance with an embodiment of the present disclosure;

FIG. 22B is a front elevation view of the second section shown in FIG. 22A;

FIG. 23A is a side elevation view of a second section of a tool in accordance with an embodiment of the present disclosure;

FIG. 23B is a front elevation view of the second section shown in FIG. 23A;

FIG. 24A is a side elevation view of a second section of a tool in accordance with an embodiment of the present disclosure;

FIG. 24B is a front elevation view of the second section shown in FIG. 24A;

FIG. 25 is an enlarged side elevation view of a portion of the second section shown in FIG. 24A;

FIG. 26A is a side elevation view of a second section of a tool in accordance with an embodiment of the present disclosure;

FIG. 26B is a front elevation view of the second section shown in FIG. 26A;

FIG. 27A is a side elevation view of a second section of a tool in accordance with an embodiment of the present disclosure;

FIG. 27B is a front elevation view of the second section shown in FIG. 27A;

FIG. 28A is a side elevation view of a tool in accordance with an embodiment of the present disclosure;

FIG. 28B is a front elevation view of the tool shown in FIG. 28A;

FIG. 29A is a side elevation view of a second section of a tool in accordance with an embodiment of the present disclosure;

FIG. 29B is a front elevation view of the second section shown in FIG. 29A;

FIG. 30A is a side elevation view of a second section of a tool in accordance with an embodiment of the present disclosure;

FIG. 30B is a front elevation view of the second section shown in FIG. 30A;

FIG. 31A is a side elevation view of a second section of a tool in accordance with an embodiment of the present disclosure;

FIG. 31B a front elevation view of the second section shown in FIG. 31A;

FIG. 32A is a side elevation view of a second section of a tool in accordance with an embodiment of the present disclosure;

FIG. 32B is a front elevation view of the second section shown in FIG. 32A;

FIG. 33A is a side elevation view of a second section of a tool in accordance with an embodiment of the present disclosure;

FIG. 33B is front elevation view of the second section shown in FIG. 33A;

FIG. 36A is a side elevation view of a second section of a tool in accordance with an embodiment of the present disclosure;

FIG. 36B is front elevation view of the second section shown in FIG. 36A;

FIG. 38A is a side elevation view of a second section of a tool in accordance with an embodiment of the present disclosure;

FIG. 38B is front elevation view of the second section shown in FIG. 38B;

FIG. 39A is a side elevation view of a second section of a tool in accordance with an embodiment of the present disclosure;

FIG. 39B is front elevation view of the second section shown in FIG. 39A;

FIG. 40A is a side elevation view of a second section of a tool in accordance with an embodiment of the present disclosure;

FIG. 40B is front elevation view of the second section shown in FIG. 40A;

FIG. 41A is a side elevation view of a second section of a tool in accordance with an embodiment of the present disclosure;

FIG. 41B is front elevation view of the second section shown in FIG. 41A;

FIG. 44A is a side elevation view of a second section of a tool in accordance with an embodiment of the present disclosure;

FIG. 44B is front elevation view of the second section shown in FIG. 44A;

FIG. 45A is a side elevation view of a second section of a tool in accordance with an embodiment of the present disclosure;

FIG. 45B is a front elevation view of the second section shown in FIG. 45A;

FIG. 47A is a side elevation view of a second section of a tool in accordance with an embodiment of the present disclosure;

FIG. 47B is a front elevation view of the second section shown in FIG. 47A;

FIG. 48A is a side elevation view of a second section of a tool in accordance with an embodiment of the present disclosure; and FIG. 48B is a front elevation view of the second section shown in FIG. 48A.

DETAILED DESCRIPTION

Figure 1:
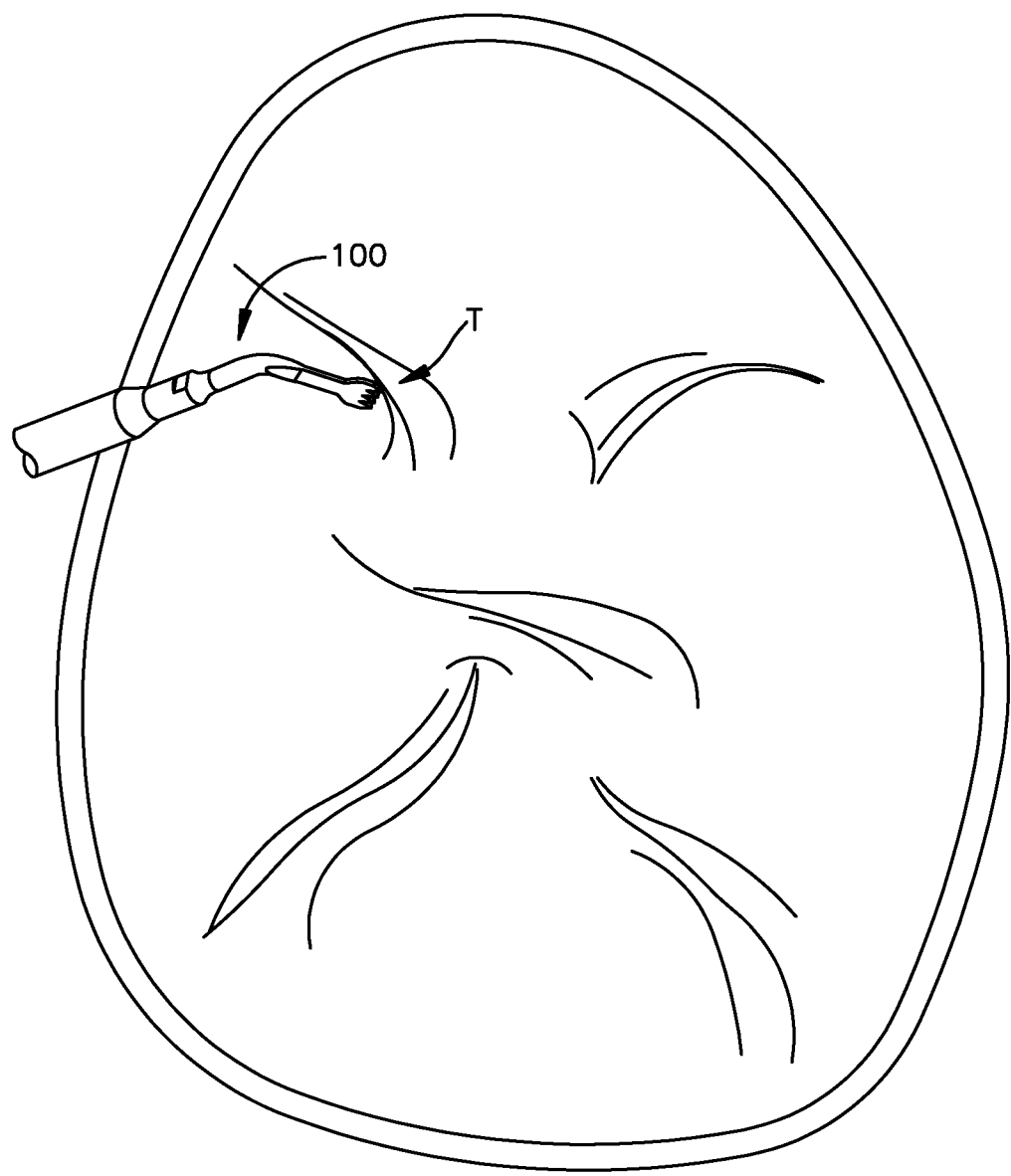
FIG. 1 is a perspective view of a portion of an ultrasonic surgical system in accordance with an embodiment of the present disclosure.
Figure 2:
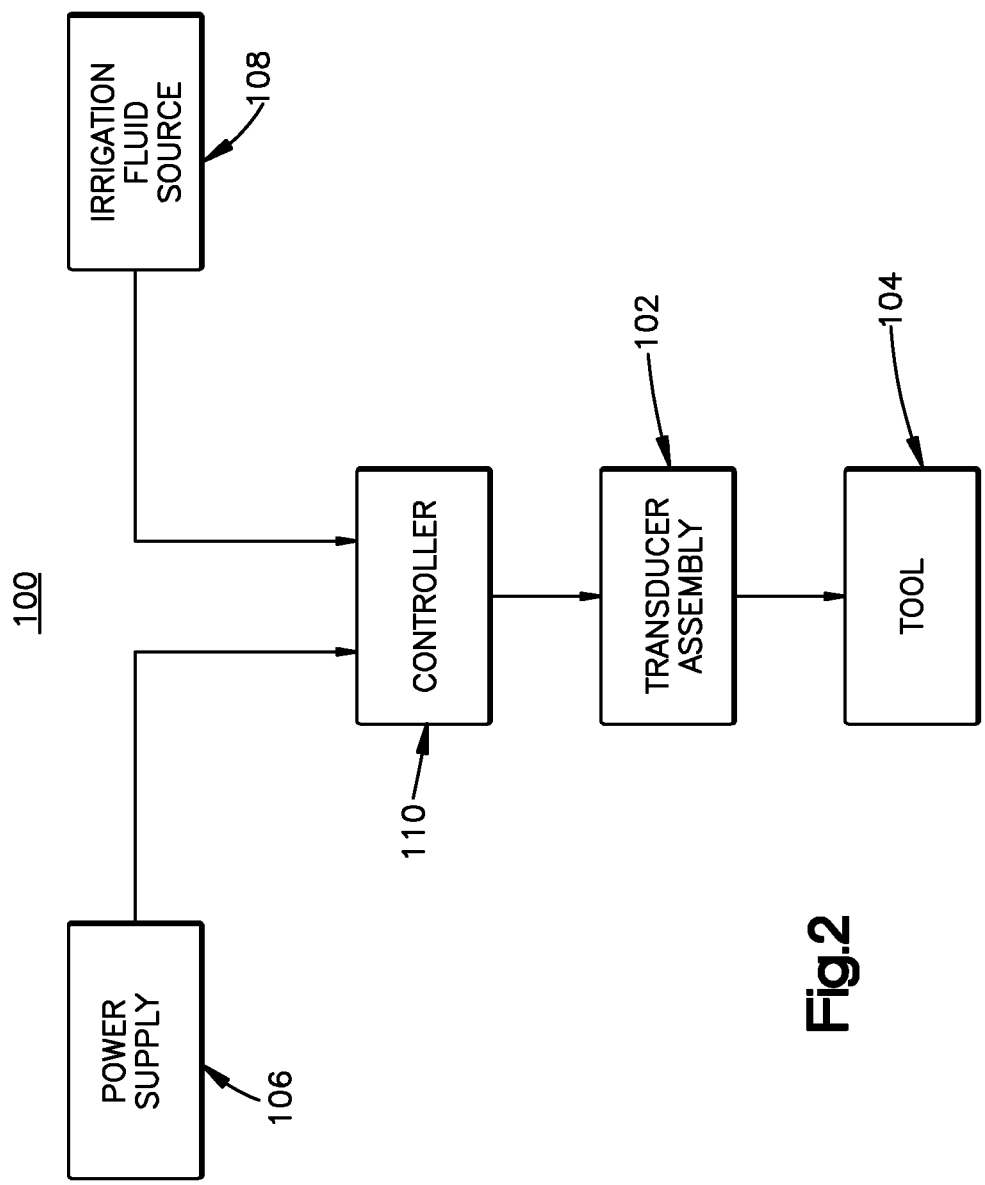
FIG. 2 is a schematic representation, in block diagram form, of an ultrasonic surgical system in accordance with an embodiment of the present disclosure.

With reference to FIGS. 1 and 2, an ultrasonic surgical system 100 employs mechanical vibrations to cut, for instance to remove or shape, a tissue body, such as anatomical tissue or a tissue substitute T. As used herein, the term tissue includes, but is not limited to, soft tissue and hard tissue. Soft tissue includes, but is not limited to, skin, tendons, ligaments, fascia, fibrous tissues, fat, Synovial membrane, muscle, nerves, and blood vessels. Hard tissue includes, but is not limited to, enamel, dentin, and bone. Tissue substitutes include soft tissue substitute, such as a graft, and hard tissue substitutes, such as calcium-phosphate cement. In one embodiment, the ultrasonic surgical system 100 includes a transducer assembly 102 and a tool 104 mechanically coupled to the transducer assembly 102. The transducer assembly 102 can covert energy, such as electrical energy, into mechanical vibrations. In an embodiment, the transducer assembly 102 is a piezoelectric transducer assembly capable of converting electrical energy into mechanical vibrations as described in detail below. Given the mechanical connection between the transducer assembly 102 and the tool 104, the mechanical vibrations generated by the transducer assembly 102 can be propagated through the tool 104. The tool 104 carries at least one cutting surface 227 that is configured to vibrate at a predetermined frequency while being brought into operative communication with the tissue body, such that the vibration of the cutting tool 104 cut, for instance shaped or remove, tissue body.

As discussed above, the transducer assembly 102 can be a piezoelectric transducer assembly configured to convert electrical energy into mechanical vibrations. A power supply 106 can supply electrical energy to the transducer assembly 102. In order to supply electrical energy to the transducer assembly 102, the power supply 106 can be electrically coupled to the transducer assembly 102. The power assembly 106 can be any suitable power supply capable of supplying the transducer assembly 102 with an electrical energy. In one embodiment, the ultrasonic surgical system 100 includes the power supply described in U.S. Pat. No. 6,765,333, the disclosure of which is hereby incorporated by reference in its entirety. Moreover, the power supply 106 can be part of, or be electrically coupled to, a frequency tracking oscillator circuitry, such as the frequency tracking oscillator circuitry described in U.S. Pat. No. 6,765,333. The frequency tracking oscillator maintains the resonance frequency of the tool 104 during operation regardless of the operating conditions by adjusting the electrical energy supplied to the transducer assembly 102 by the power supply 106. As such, even if the tool 104 is moved from a position where it contacts hard tissue to another position where it is only in contact with a fluid, such as blood, the frequency tracking oscillator circuitry adjusts the supply voltage provided by the power supply 106 to the transducer assembly 102 in order to maintain the resonance frequency of the tool 104 substantially constant. Alternatively, the power supply 106 can be electrically connected to any other device, apparatus, or circuitry capable of controlling the power supply 106 in order to maintain the resonance frequency of the tool 104 substantially constant regardless of the operating conditions or environment.

In the depicted embodiment, the ultrasonic surgical system 100 can further include an irrigation fluid source 108 disposed in fluid communication with the tool 104. The irrigation fluid source 108 can be directly coupled to the tool 104. Alternatively, the water supply 108 can be fluidly coupled to the tool 104 through a controller 110 and/or the transducer assembly 102. The irrigation fluid source 108 contains any fluid, such as water or a saline solution, suitable for irrigating a target tissue site. As discussed in detail below, tool 104 can define openings for delivering the irrigation fluid to the target site to prevent, or at least minimizes, heat generation and necrosis.

The controller 110 can be electrically coupled to the power supply 106 and fluidly coupled to the irrigation fluid source 108. In operation, the controller 110 can be configured to control the electrical energy supplied to the transducer assembly 102. An embodiment of the controller 110 is in the form of a console that includes a user interface that allows a user to adjust the power supplied to the transducer assembly 102. The user interface can include a touchscreen capable of receiving input commands from a user. In addition or alternatively to the touchscreen, the controller 110 can include a foot pedal or any other external manual control that allows a user to control the power or electrical energy supplied to the transducer assembly 102. In one embodiment, the controller 110 includes the frequency tracking oscillator circuitry described above.

The controller 110 can additionally or alternatively be configured to control the delivery of irrigation fluid to the tool 104. As discussed above, the irrigation fluid source 108 is fluidly coupled to the tool 104 directly or indirectly via the controller 110 and/or the transducer assembly 102. The ultrasonic surgical system 10 can include one or more pumps for displacing the irrigation fluid from the irrigation fluid source 108 to the tool 104. The controller 110 can be configured to control the pumps in order to the control the delivery of irrigation fluid to the tool 104. As such, the controller 110 can include circuitry configured to control the pumps.

With reference to FIGS. 3A and 3B, the transducer assembly 102 can be coupled to the controller 110 (FIG. 2). In one embodiment, the transducer assembly 102 includes a housing 112 defining an inner cavity 115. The housing 112 can be configured as a handle or handpiece to allow a user to easily grasp the transducer assembly 102. Moreover, the housing 112 defines a first or proximal end 114 and a second or distal end 116 spaced from the first end 114 along a longitudinal axis L. The terms "proximal," "distal," and derivatives thereof as used with respect to the transducer assembly 102 and components thereof are made with reference to a direction from distal end 116 toward the proximal end 114, and a direction from the proximal end 114 toward the distal end 116, respectively. The proximal end 114 of the housing 112 is configured to be connected to at least one electrical connector 118, such as an electrical cable. The electrical connector 118 can be any suitable structure, apparatus, or device, capable of electrically coupling the controller 110 (FIG. 2) and the transducer assembly 102. In one embodiment, the electrical connector 118 can also mechanically connect the transducer assembly 102 to the controller 110. However, any suitable wireless connection can electrically couple the controller 110 to the transducer assembly 102.

With continued reference to FIGS. 3A and 3B, the housing 112 defines an outer surface 120 and an inner surface 122. At least a portion 124 of the outer surface 120 can define a substantially cylindrical shape. Another portion 126 of the outer surface 120 adjacent the distal end 116 can define a substantially frusto-concial shape. The inner surface 122 of the housing defines the inner cavity 115. The inner cavity 115 extends at least between the proximal end 114 and the distal end 116 of the housing 112. In one embodiment, the inner cavity 115 is configured and sized to receive at least a portion of the electrical connector 118.

With continued reference to FIGS. 3A and 3B, in an embodiment, the transducer assembly further includes one or more piezoelectric members or resonators 128 each electrically coupled to the power supply 106 via, for instance, electrical connector 118. The electrical connector 118 can electrically couple the piezoelectric members 128 to the controller 110 (FIG. 2). The controller 110 (FIG. 2) is in turn electrically connected to the power supply 106. Irrespective of the specific structure employed to electrically couple the piezoelectric members 128 to the power supply 106, the power supply 106 can supply electrical energy to the piezoelectric members 128. In the depicted embodiment, the electrical connector 118 transmits electrical energy supplied by the power supply 106 to the piezoelectric members 128. Each of the piezoelectric members 128 is configured to vibrate upon receive of electrical energy from, for example, the power supply 106. In one embodiment, at least one of the piezoelectric members 128 is configured to vibrate at an ultrasonic frequency when it receives electrical energy. At least one piezoelectric member 128 can be a piezo-ceramic plate. In the depicted embodiment, the piezoelectric members 128 include a plurality of stacked piezo-ceramic plates 130. For instance, the piezoelectric members 128 can be six piezo-ceramic plates stacked togheter. Nevertheless, the piezoelectric members 128 can have other shapes and be made of other piezoelectric materials. For example, the piezoelectric members 128 can be shaped as rings. Alternatively, the piezoelectric member 128 can be constructed as single monolithic (one-piece) structure. Irrespective of its construction, the piezoelectric member 128 defines a proximal or first end 134 and a distal or second end 136.

With continued reference to FIGS. 3A and 3B, in addition to the backing mass structure 132, the transducer assembly 102 can further include vibration transmission member 138, such as an impedance matching member, attached to the distal end 136 of the piezoelectric member 128. In the depicted embodiment, the entire vibration transmission member 138 is disposed within the housing 112. The vibration transmission member 138 is configured to facilitate the propagation of the mechanical vibrations generated by the piezoelectric member 128 into the tool 104. To this end, vibration transmission member 138 can substantially match the output impedance of the source (i.e., the piezoelectric member 128) to the input impedance of the load (i.e., tool 104). In one embodiment, the vibration transmission member 138 is at least partly made from a material that has an acoustic impedance that gradually changes from that of the piezoelectric member 128 to that of the tool 104. In another embodiment, the vibration transmission member 138 is at least partly made of a material that has an acoustic impedance between the that of the piezoelectric member 128 and the acoustic impedance of the tool 104. The vibration transmission member 138 can be made of one or more layers. These layers of the vibration transmission member 138 can each be made of materials having different acoustic impedances. Alternatively, all the layers forming the vibration transmission member 138 can have the substantially the same acoustic impedance. In an embodiment, the vibration transmission member 138 can be a single monolithic ("one-piece") structure capable of facilitating the transmission of the mechanical vibrations stemming from the piezoelectric member 128 into the tool 104.

With continued reference to FIGS. 3A and 3B, the vibration transmission member 138 defines a proximal or first end 140 attached to the piezoelectric member 128 and a distal or second end 142 configured to be attached to the tool 104. Thus, the tool 104 is configured to be attached to the distal end 142 of the vibration transmission member 138. In one embodiment, the tool 104 can vibrate at selected frequency range between 28 and 36 kHz upon actuation of the piezoelectric member 128. At this frequency range, the tool 104 only cuts mineralized tissue, such as teeth and bone, in a very precise way, while limiting the risk of soft tissue lesions. Soft tissues such as nerves, blood vessels, dura or membrane are not altered by the tool 104 because of their ability to oscillate at the same speed and amplitude as the tool 104.

With continued reference to FIGS. 3A and 3B, the ultrasonic surgical system 100 can further include fluid conduit 144 configured to convey irrigation fluid from the irrigation fluid source 108 (FIG. 2) into an inner portion of the tool 104 as described in detail below. The fluid conduit 144 can be a tube defining a channel or any other structure capable of conveying an irrigation fluid from the irrigation fluid source 108 into an inner portion of the tool 104. A portion of the fluid conduit 144 can be disposed within the housing 112 and can extend from a proximal end 114 in a direction toward the distal end 116 of the housing 112. The fluid conduit 144 fluidly interconnects the irrigation fluid source 108 (FIG. 2) and an inner portion of the tool 104. Accordingly, the fluid conduit 144 can be in fluid communication with the fluid source 108 (FIG. 2) and an inner portion of the tool 104.

With continued reference to FIGS. 3A and 3B, the ultrasonic surgical system 100 can further include a light source 146 configured to illuminate a the surgical target site. In the depicted embodiment, the light source 146 is supported within the housing 112 and includes a support body 148, such as a support ring, and one or more light emitting diodes (LEDs) 150 supported by the support body 148. The support body 148 is disposed around a portion of the vibration transmission member 138. The LEDs 150 are attached to the support body 148 such that they illuminate in a direction toward the distal end 116 of the housing 112. The distal end 116 of the housing 112 defines an open end 152 that allows light emitted by the light source 146 to travel in a direction toward the surgical target site to enhance visibility of the surgical target site near the tool 104.

With reference to FIGS. 3C-D, the transducer assembly 102 can include a mounting member 149, such as a frame, that is configured to hold the support body 148. In the present disclosure, the mounting member 149 can also be referred to as a mount. The support body 148 can be connected to the mounting member 149. In the depicted embodiment, the mounting member 149 is disposed around the vibration transmission member 138, and is attached to the housing 112. The mounting member 149 supports one or more electrical contacts 151. The electrical contacts 151 are configured to be electrically coupled to the power supply 106 (see FIG. 2) when the transducer assembly 102 is electrically connected to the power supply 106. The support body 148 also supports one or more electrical contacts 153 that are configured to be electrically coupled to the electrical contacts 151. The electrical contacts 153 can be shaped as rods that protrude from the support body 148 in a direction toward the proximal end 114 (see FIG. 3B) of the transducer assembly 102. In operation, the electrical contacts 153 are configured to transmit electrical energy to the light source 146 (e.g., LEDs 150) such that the light source 146 can illuminate in a direction toward the distal end the distal end 116 of the housing 112.

With continued reference to FIGS. 3C-D, the transducer assembly 102 includes a light diffuser 147 configured to be disposed over the light source 146. The light diffuser 147 is configured to receive light from the light source 146 and regulate the light such that the regulated light has an intensity distribution suitable for substantially uniform illumination of a target site. In the depicted embodiment, the light diffuser 147 has a substantially frusto-conical shape. However, the light diffuser 147 may have any other suitable shape. The transducer assembly 102 further includes a nose cone 154 configured and sized to be disposed over the light diffuser 147. In the depicted embodiment, the nose cone 154 has a substantially frust-conical shape. However, the nose cone 154 may have other suitable shapes.

With reference to FIGS. 3C-D, the vibration transmission member 138 includes a body 139 and a connecting member 141 that protrudes from the body 139 in a direction toward the distal end 116 of the housing 112. The body 139 can have a cross-sectional dimension, such as a diameter, that is greater than the cross-sectional dimension, such as a diameter, of the connecting member 141. The connecting member 141 defines an outer surface 143 and external threads 145 that are formed on the outer surface 143. The external threads 145 are configured to mate with the inner threads 219 of the tool 204 such that the tool 204 can be connected to the transducer assembly 102.

Figure 4:
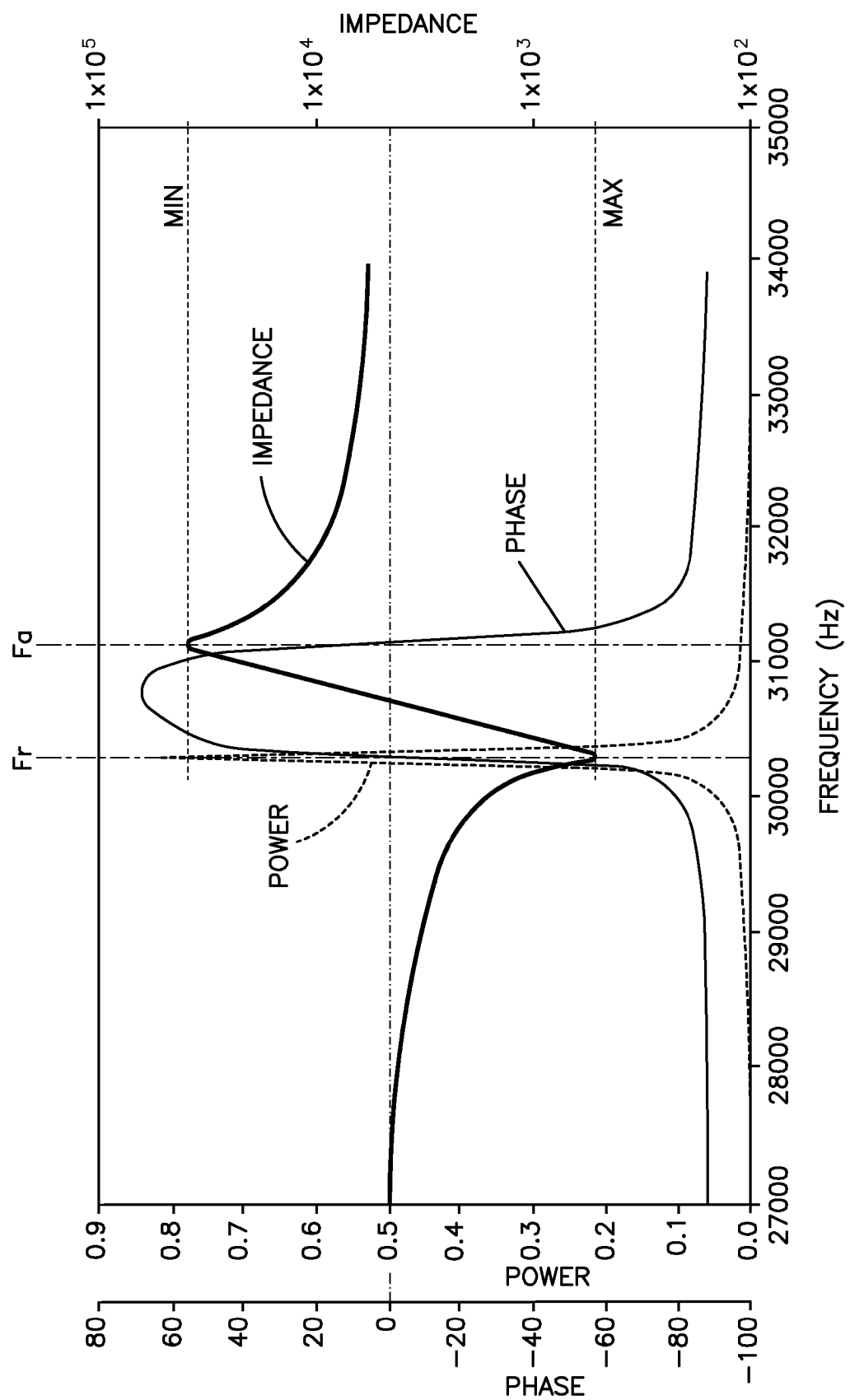
FIG. 4 is a graph illustrating the variations of phase-shift and power as a function of the frequency.

With reference to FIGS. 1 and 4, as discussed in detail above, some of the embodiments of the tools described in the present disclosure are relatively longer and thinner than conventional tools. The length and cross-sectional dimension of conventional tools herein allow the surgeon to employ minimally invasive approaches and to reach areas difficult to access. Moreover, in conventional tools, when the user grabs the handpiece that is connected to the tool, the user's fingers and the handpiece must be positioned very close to the target surgical site. As a consequence, the user's fingers and the handpiece obstruct the user's line of sight to the target surgical site. To enhance visibility, surgeons often cut soft tissue surrounding the target surgical site. Such cuts, however, may cause post-operative inflammation. When using the relatively longer tools described in the present disclosure, the user's fingers and the housing 112 (e.g., handpiece) are positioned farther away from the target surgical site and, consequently, the user has a direct line of sight to the target site and does not need to cut soft tissue surrounding the target bone, thereby reducing post-operative swelling Conventional tools cannot simply be elongated to have the longer lengths as some of the tools described in the present disclosure, because such elongation would significantly affect the efficiently of the transducer assembly. Typically, conventional tools are made of stainless steel. Stainless steel is relatively heavy in comparison with other materials. If a conventional stainless steel tool is elongated to reach the relatively longer lengths of some of the tools described in the present disclosure, vibrating such a heavy stainless steel tool would require significant amount of power from a power supply. In turn, this increase in power can overheat the piezoelectric members of the transducer assembly, thereby causing, among other things, inefficiencies in the transducer assembly. In other words, if the piezoelectric members or resonators overheat, the transducer assembly does not operate at its optimal conditions.

With reference to FIGS. 1 and 4, in an embodiment, the transducer assembly 102 can vibrate in response to a sinusoidal electrical signal having a frequency band between about 27 and about 34 kilohertz (KHz). However, it is envisioned that the transducer assembly 102 can vibrate when it receives any other modulated electrical signal having other frequency bands. As discussed above, the transducer assembly 102 propagates vibrations to the tool 102. The vibration of the tool 102 depends, among other things, of the power supplied to the transducer assembly 102. The power supplied to the transducer assembly 102 can be at least partially controlled by the frequency tracking oscillator circuitry, such as the frequency tracking oscillator circuitry described in U.S. Pat. No. 6,765,333, the entire disclosure of which is hereby incorporated by reference. The transducer assembly 102 can receive power ranging between about 0.5 and about 10 Watts (W). This power can be in the form of a sinusoidal signal and is a function of the voltage, the current, and the phase shift of the current relative to the voltage. To determine the optimal operating conditions of the transducer assembly 102, tests were conducted to determine the power, the phase, and the impedance of the transducer for each frequency in the range between 27 and 34 kilohertz (KHz). The results of these tests are shown in the graph depicted in FIG. 4. By observing this graph, the resonance frequency and the anti-resonance frequency of the transducer assembly 102 can be obtained. The resonance frequency Fr is the frequency at which the impedance is minimum and the phase shift is zero. The anti-resonance frequency Fa is the frequency at which the impedance is maximum and the phase shift is zero. In this test, it was determined that the resonance frequency Fr is about 30,297 Hz, and the minimum impedance was 509 ohms When vibrated at the resonance frequency Fr, the transducer assembly 102 most efficiently converts electrical energy input into mechanical vibrations. As the frequency is increased, the transducer assembly 102 can reach its anti-resonance frequency, at which point the impedance reaches its maximum value. Thus, the transducer assembly 102 should be vibrated at or close to the resonance frequency Fr but its vibration frequency should not reach or exceed the anti-resonance frequency Fa while maintain a zero phase shift.

Figure 5A:
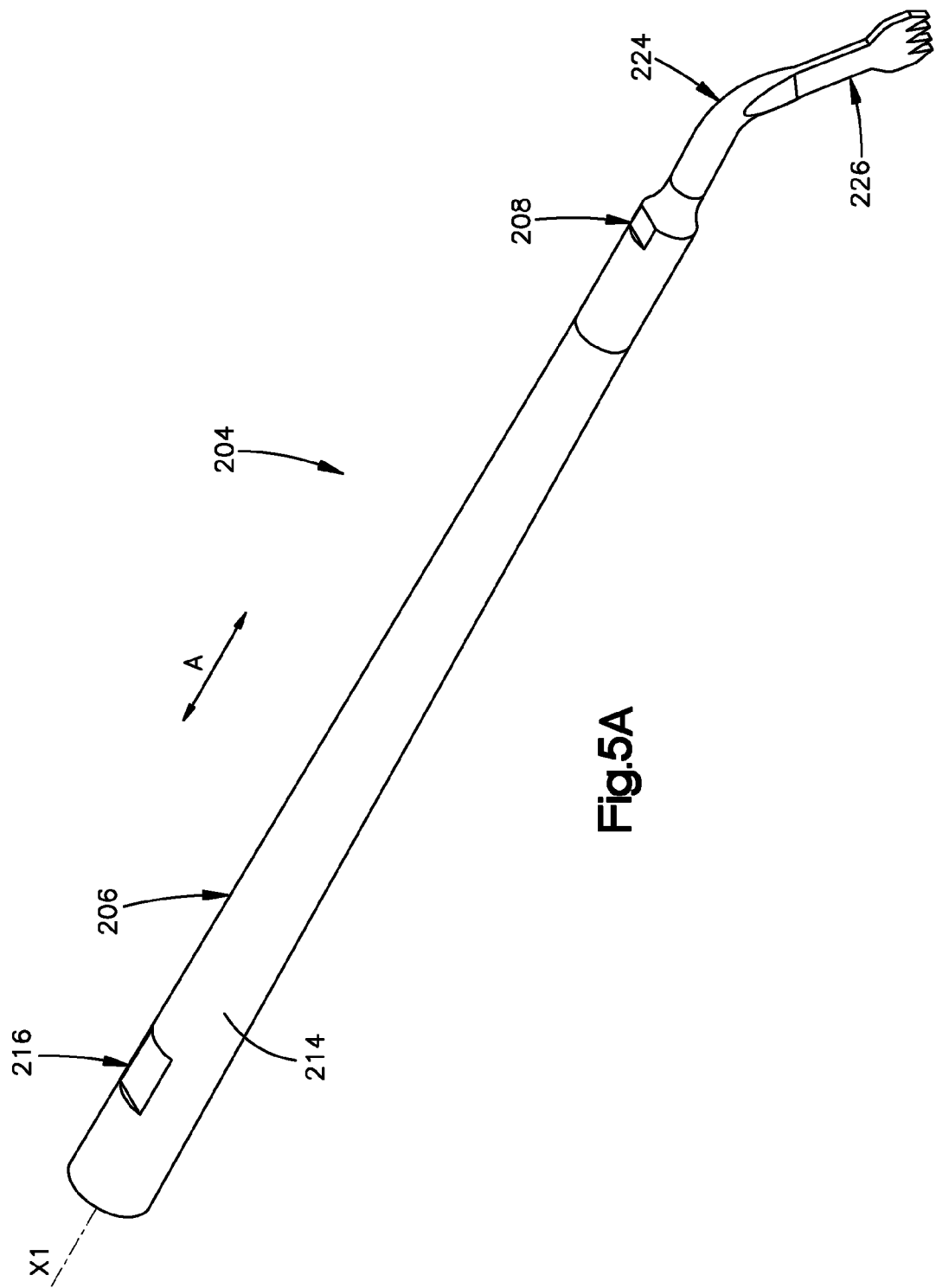
FIG. 5A is a perspective view of a tool in accordance with an embodiment of the present disclosure.

With reference to FIGS. 5A-5C, an embodiment of a tool 204 that is at least partly made of a titanium alloy, has length L1 that is greater than the length of conventional tools. The length L1 is defined by the distance from a first or proximal end 210 and a second or distal end 212 of the tool 204 along a direction defined by the longitudinal axis X1. The longitudinal axis X1 extends along at least a portion of the tool 204 in a longitudinal direction indicated by the arrow A. In the depicted embodiment, the length L1 of the tool 204 is greater than about 80 millimeters. In an embodiment, the length L1 of the tool 204 ranges between about 20 millimeters and 120 millimeters. In one embodiment, the length L1 of the tool 204 is about 105.7 millimeters. As discussed above, the length L1 of the tool 204 is important, because it allows the surgeon to employ minimally invasive approaches and to reach areas difficult to access. The length L1 of the tool 204 also enhances visibility of the surgical target site and forgoes the need to cut soft tissue surrounding the target bone or soft tissue, thereby reducing post-operative swelling.

With reference to FIGS. 5A-5C, the tool 204 is configured to be removably attached to the transducer assembly 102 (FIG. 2). In one embodiment, tool 204 can be removably coupled to the vibration transmission member 138 by any suitable apparatus, device, or mechanism. For instance, the tool 204 can define a threaded bore configured to mate with an external thread formed on outer surface of the vibration transmission member 138. As discussed above, the vibration transmission member 138 transmits vibrational motion from the piezoelectric members 128 to the tool 204. Thus, the tool 204 is configured to vibrate when the piezoelectric member 128 vibrate in response to an electrical signal.

With continued reference to FIGS. 5A-5C, in the depicted embodiment, the tool 204 includes a first or proximal section 206 and a second or distal section 208 that is spaced from the first or proximal section 206 along the longitudinal direction A. The first section 206 can extend into the housing 112, and is configured to be attached to the transducer assembly 102. The second section 208 carries at least one cutting surface 227 that is configured to operate on a surgical target site so as to cut, for instance shape or remove, tissue from the surgical site. In an embodiment, the first and second sections 206 and 208 are made from different materials. For instance, the first section 206 can be made of a first material, and the second section 208 can be made from a second material that is heavier than the first material. In other words, the density of the second material is greater than the density of the first material. Thus, the second material is denser than the first material. The combination of the two materials (e.g., alloys) having different densities allows the production of an efficient and effective tool 204 that is longer than the conventional tools made of a single material. Moreover, the use of materials having different densities enhances the vibration transmission from the transducer assembly 102 to the extremity of the tool 204 (e.g., cutting member 225). Therefore, a tool, such as the tool 204, that is made of the materials having different densities (as described in the present disclosure) enhances the tissue cutting efficiency in a very precise way. As discussed above, the term "tissue" includes hard tissue, such as bone or tooth, and soft tissue while the term "cutting" includes shaping. In addition, the tool 204, which is made of materials having different densities, is safer to use relative to conventional tools because the user can select via a controller 110 to vibrate the tool 204 at a vibration that would only cut the desired tissue. For instance, at predetermined frequency range, the tool 204 only cuts hard tissue and does not cut soft tissue, such as nerve, membrane, skin, dura matter etc. The first section 206 can have an elongated configuration and be made of a material that is lighter than the stainless steel used in conventional tools. Thus, the first section 206 can be partly or entirely made of a material that has a density lower than the density of stainless steel. The materials with different densities listed above are important because it allows the cutting member 225 of the tool 204 to vibrate at a cutting member amplitude that ranges between about 300 percent to about 500 percent of a transducer assembly amplitude of the vibration produced by the transducer assembly 102 when the first section 206 is coupled to the transducer assembly 102 and the transducer assembly 102 is activated and is receiving power from the power supply 106.

With continued reference to FIGS. 5A-5C, in an embodiment, the first section 206 can be partly or wholly made of any suitable biocompatible titanium alloy. For instance, the first section 206 is partly or entirely made from a titanium-aluminum-vanadium alloy. The first section 206 can be sufficiently flexible to transmit the mechanical vibrations generated by the piezoelectric member 128 to tissue or tissue substitute in order to cut, for instance shape or remove, such tissue. To this end, the first section 206 can be partly or entirely made from a material sufficiently flexible to transmit vibrational motion from the piezoelectric member 128 but sufficiently rigid to allow the tool 204 to cut, for instance shape or remove, hard tissue, soft tissue, or tissue substitutes. The moduli of elasticity described above are important because it provides the first section 204 with sufficient flexibility to allow the propagation of mechanical vibrations along the tool 204 and also because it provides the tool 204 with sufficiently rigidity so that it can cut, for instance shape or remove, hard tissue, soft tissue, or tissue substitutes. The use of a titanium alloy for the first section 206 also allows the transducer assembly 102 to generate mechanical vibrations efficiently and minimizes the risk of overheating the transducer assembly 102.

With continued reference to FIGS. 5A-5C, the first section 206 of tool 204 extends in a direction along a longitudinal axis X1 and has an outer surface 214. The outer surface 214 of the first section 206 defines a cross-sectional dimension or diameter D1. The first section 206 can be tapered so that the cross-sectional dimension decreases in a direction from the proximal end 210 toward the distal end 212. The cross-sectional dimension or diameter D1 is less than cross-sectional dimension or diameter of conventional tools to allow the surgeon to reach difficult areas to access.

With continued reference to FIGS. 5A-5C, the first section 206 can further include one or more recesses 216 on the outer surface 214. The recesses 216 are configured and sized to allow a holding tool, such as a wrench, to securely hold the tool 204. During assembly, a user can place portion of the holding tool, such as a wrench, to hold the tool 204. The user can then turn the holding tool to turn tool 204 and thereby disconnect the tool 204 from the transducer assembly 104. In this embodiment, the tool 204 can be connected to the transducer assembly via a threading mechanism. In one embodiment, the tool 204 defines two identical recesses 214 disposed in a diametrically-opposed relationship to each other.

With continued reference to FIGS. 5A-5C, the second section 208 of the tool 204 can be directly or indirectly connected to the first section 206. The second section 208 can be of a different material than the first section 206. For instance, the second section 208 can be partly or wholly made of a stainless steel. In one embodiment, the stainless steel used for making the second section 208 can be sufficiently strong to allow this second section 208 to cut, for instance shape or remove, even hard tissue. Thus, in one embodiment, the stainless steel of the second section 208 is subjected to thermal treatment to increase its strength and hardness In the depicted embodiment, the second section 208 can include a connection or elongated portion 218 coupled to the first section 206. The connection portion 218 extends along the longitudinal axis X1 and defines an outer surface 220. The outer surface 220 of the connection portion 218 defines a cross-sectional dimension or diameter D2. The outer surface 220 can be tapered so that the cross-sectional dimension or diameter D2 decreases in a direction toward the distal end 212.

With continued reference to FIGS. 5A-5D, the second section 208 can further include a shoulder 222 coupled to the connection portion 218. The shoulder 222 can be in turn connected to an elbow 224. The elbow 224 allows the tool 204 to change it direction relative to the longitudinal axis X1.

With continued reference to FIGS. 5A-5D, the second section 208 further includes an operative portion 226 coupled to the elbow 224. The operative portion 226 includes a support body 223 and cutting member 225 that is carried by the support body 223. For instance, the cutting member 225 can be monolithic with the support body 223. The cutting member 225, in turn, carries at least one cutting surface 227 that is configured to vibrate and to contact a tissue body in order to cut, for instance shape or remove, the tissue body. In the depicted embodiment, the operative portion 226 can extend along an axis Z1 that is oriented at an oblique angle relative to the longitudinal axis X1. At least part of the operative portion 226 can have a substantially flat or planar configuration as shown in FIG. 5C. In accordance with one embodiment, the cutting member 225 can define more than one cutting surface 227, such as at least a pair of cutting surfaces 227, that define a cutting edge 228 that is configured to cut, for instance shape or remove, a tissue body as it vibrates at a predetermined frequency. The edge 228 can thus be sharp and can be serrated or non-serrated. In the embodiment illustrated in FIGS. 5A-C, the cutting member 225 defines a serrated edge 228 so as to define a plurality of teeth 230 that protrude outward from the support body 223 along a direction away from the elbow 224, which can be angularly offset with respect to the longitudinal direction A. Alternatively, it should be appreciated that the teeth 230 can protrude outward from the support body 223 along a direction substantially parallel to the longitudinal direction A. The teeth 230 of the cutting member 225 are spaced from each other along a row direction indicated by arrow Y1.

With continued reference to FIGS. 5A-5D, the tool 204 can further define an inner surface 213. The inner surface 213 defines an irrigation fluid channel 215 that can be disposed in fluid communication with the fluid conduit 144 (FIG. 3B) when the tool 204 is coupled to the transducer assembly 102. The irrigation fluid channel 215 is sized and configured to receive any suitable irrigation fluid, such as water or saline. Moreover, the irrigation fluid channel 215 can extend at least into or through at least a portion of the tool 204, such as at least a portion of the first section 206, along a direction having a directional component along the longitudinal direction A, and can further extend at least into or through at least a portion of the second section 208, so as to define an outlet 217 of the tool 204. The irrigation fluid channel 215 can alternatively define more than one outlet 215. The outlet 217 can be located at the operative portion 226 of the tool 204, such that irrigation fluid can travel through the irrigation fluid channel 215 and exit the tool 204 at the outlet 217. The irrigation fluid can thus exit the outlet 215 and be brought into contact with the cutting member 225 so as to cause the physical phenomenon of cavitation effect. For instance, cavitation can occur when the cutting member 225 is in contact irrigation fluid as the cutting member 225 vibrates, such that irrigation fluid creates micro-bubbles that have hemostatic effects on the cutting surface 227, partially due to the production of nascent oxygen during cavitation. The cavitation phenomenon provides visibility of the operative site, removes bone debris and limits temperature rise due to tissue degradation. The inner surface 213 further defines an inner thread 219 at the proximal end 210 of the tool 210.

In operation, tool 204 can be used for mandible and skull based procedures, transnasal and transorbital approaches, lateral decompression, and full ramus osteotomy. Thus, the tool 204 can be used in neurosurgery and cranio-maxillofacial (CMF) surgery. For example, in neurosurgery, the tool 204 can be used for decompression of neurovascular structures (i.e., optic nerve), frontal craniotomy, and a transorbital approach. The tool 204 can also be used to gain access the following anatomies, namely: the anterior clinoid process, dorsum sellae, internal acoustic meatus, posterior cranial fossa, middle cranial fossa, groove for sigmoid sinus, superorbital fissure, optical canal, cribriform plate, crista galli, clinoid process, lesser wing of sphenoid, and greater wing of sphenoid. In CMF surgery, the tool 204 can also be used to gain access the following anatomies, namely coronoid process, condyle, ramus, angle, groove for external maxillary artery, maxillary frontal process, anterior lacrimal crest, lacrimal groove, orbital surface, maxillary tuberosity, zygomatic process, alveolar process, nasal bone, vomer bone, sphenoid, and palatine bones.

In use, the tool 204 can be connected to the transducer assembly 102 using any suitable apparatus or mechanism. The tool 204 can be pre-connected to the transducer assembly 102. Once the tool 204 is connected to the transducer assembly 102, the power supply 106 is activated to energize the transducer assembly 102. When the power supply 106 is activated, electrical energy is supplied to the transducer assembly 102. The transducer assembly 106 can then convert the electrical energy into mechanical vibrations. In one embodiment, the piezoelectric members or resonators 128 vibrates upon receipt of the electrical energy. The transducer assembly 102 propagates the mechanical vibrations to the tool 204. When tool 204 receives the mechanical vibrations generated by the transducer assembly 104, its first section 206 and at least a part of the section 208 vibrate in a direction back and forth in the direction indicated by arrows A. This back and forth vibration of the first section 206 and at least a part of the section 208 causes the elbow 224 to move in a whipping manner such that the operative portion 226 can vibrate in the direction indicated by arrows Y1. The edge 228 can be placed in contact with the tissue body to be cut, for instance shaped or removed. As the operative portion 226 vibrates in the direction indicated by arrow Y1, the teeth 230 of the edge 228 contact the target tissue body and cut, for instance shape or remove, such tissue body.

Figure 6:
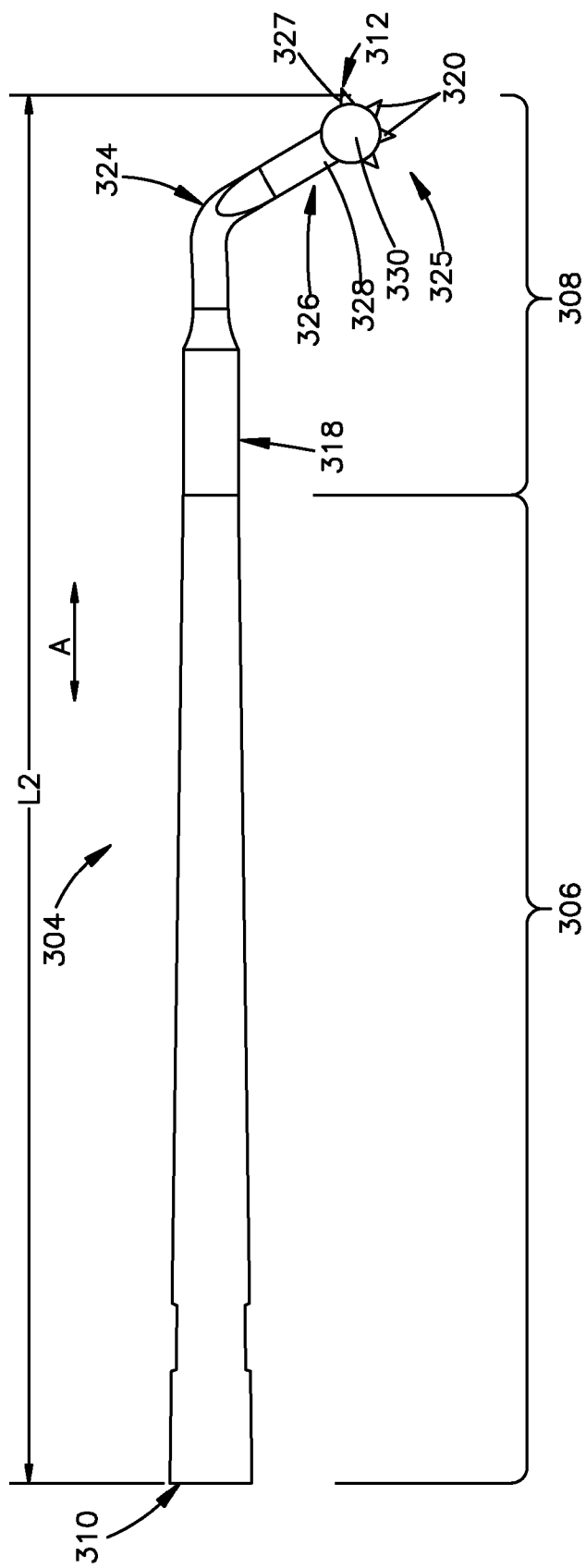
FIG. 6 is a side elevation view of a tool in accordance with an embodiment of the present disclosure.

With reference to FIG. 6, another embodiment of a tool 304 can be mechanically coupled to the transducer assembly 102 (FIG. 2). The tool 304 is substantially similar to the tool 204 shown in FIGS. 5A-5C, except for the operative portion 326, and defines a first or proximal end 310 and a second or distal end 312. The tool 304 can have length L2 defined between the proximal end 310 and the distal end 312 along a longitudinal direction A. The length L2 can be substantially similar or identical to the length L1 described above with respect to FIGS. 5A-5C. In the depicted embodiment, the length L2 of the tool 304 is greater than about 80 millimeters. In an embodiment, the length L2 of the tool 304 ranges between about 20 millimeters and 120 millimeters. In one embodiment, the length L2 of the tool 304 is about 105.7 millimeters. The length L2 of the tool 304 is important, because it allows the surgeon to employ minimally invasive approaches and to reach areas difficult to access. The length L2 of the tool 304 also enhances visibility of the surgical target site and forgoes the need to cut soft tissue surrounding the target bone or soft tissue, thereby reducing post-operative swelling.

With continued reference to FIG. 6, the tool 304 includes a first section 306 and second section 308. The first section 306 and the second section 308 can be made of different materials. For example, the first section 306 can be made of a titanium alloy, whereas the second section 308 can be made of stainless steel. In one embodiment, the first section 306 can be substantially similar or identical to the first section 206 shown in FIGS. 5A-5C. The second section 308 can be substantially similar or identical to the second section 208 shown in FIGS. 5A-5C except for its operative portion 326. Like the second section 208 shown in FIGS. 5A-5C, the second section 308 of the tool 304 can include a connection portion 318 that is directly or indirectly connected to the first section 306 and an elbow 324 that is coupled to the connection portion 318. The operative portion 326 is substantially shaped as a mace. As used herein, the term "mace" refers to a spiked staff or club used especially in the Middle Ages for breaking armor. Thus, the operative portion 326 includes a support body 323 and cutting member 325 that is carried by the support body 323. For instance, the cutting member 325 can be monolithic with the support body 323. The cutting member 325, in turn, carries at least one cutting surface 327 that is configured to vibrate and to contact a tissue body in order to cut, for instance shape or remove, the tissue body. The cutting surface 327 can define a cutting edge 328 so as to define a plurality of spikes 330 that produce radially outward from the support body 323. The spikes 320 can protrude from the support body 323 in different directions with respect to the longitudinal direction A. For instance, some of the spikes 320 can protrude from the support body 323 along a direction that is angularly offset with respect to the longitudinal direction A. One or more spikes 320 can protrude from the support body 323 along a direction that is substantially parallel to the longitudinal direction A. The support body 323 can have a substantially ellipsoidal shape. As used herein, the term "ellipsoidal" includes, but is not limited to, the following terms, namely: spherical, oblate spheroidal, prolate spheroidal, and a scalene ellipsoidal. Hence, the body 323 can have a substantially spherical shape, a substantially oblate spheroidal shape, a substantially prolate spheroidal shape, or a substantially scalene ellipsoidal. The spikes 330 can have a substantially pyramidal shape. The tool 304 can additionally include an irrigation channel and inner threads as described above with respect to FIG. 5D.

With continued reference to FIG. 6, the operation of the tool 304 is substantially similar or identical to the operation of the tool 204 described above in connection with FIGS. 5A-5C. Thus, tool 304 can vibrate upon activation of the transducer assembly 102 (FIG. 2). The tool 304 can be used for skull base surgery. For example, in neurosurgery, the tool 304 can be used for decompression of neurovascular structures (i.e., optic nerve), frontal craniotomy, and transorbital approach. The tool 304 can also be employed for accessing or doing work on the following anatomies, namely: anterior clinoid process, dorsum sellae, internal acoustic meatus, posterior cranial fossa, middle cranial fossa, groove for sigmoid sinus, superorbital fissure, optical canal, cribriform plate, crista galli, clinoid process, lesser wing of sphenoid, and greater wing of sphenoid. In CMF surgery, the tool 304 can be used for accessing or doing work on the coronoid process, condyle, ramus, angle, groove for external maxillary artery, maxillary frontal process, anterior lacrimal crest, lacrimal groove, orbital surface, maxillary tuberosity, zygomatic process, alveolar process, nasal bone, vomer bone, Sphenoid, and palatine bones.

Figure 7:
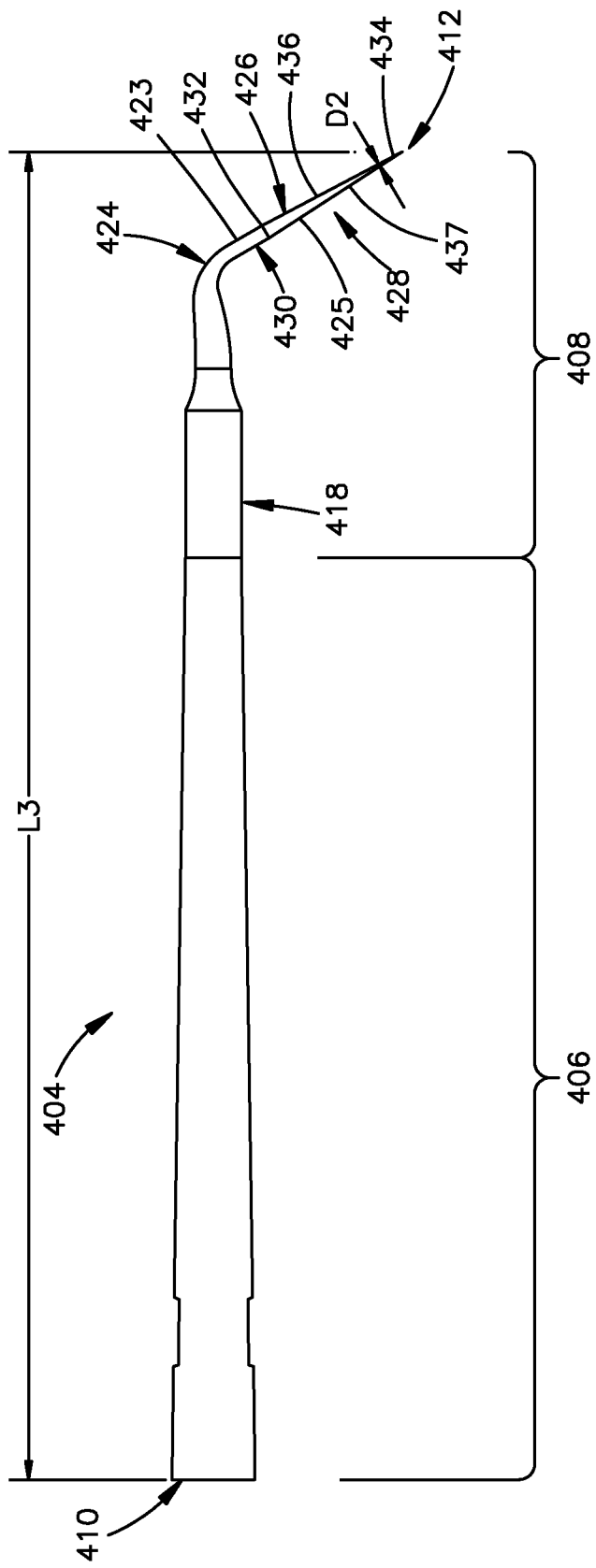
FIG. 7 is a side elevation view of a tool in accordance with an embodiment of the present disclosure.

With reference to FIG. 7, an embodiment of a tool 404 can be removably coupled to the transducer assembly 102 (FIG. 2). The tool 404 is substantially similar to the tool 204 described above with respect to FIGS. 5A-5C, and defines a first or proximal end 410 and a second or distal end 412. For instance, the tool 404 can a length L3 defined between the proximal end 410 and the distal end 412 along the longitudinal direction A. The length L3 can be substantially similar or identical to the length L1 described above with respect to FIGS. 5A-5C. In the depicted embodiment, the length L3 of the tool 404 is greater than about 80 millimeters. In an embodiment, the length L3 of the tool 404 ranges between about 20 millimeters and 120 millimeters. In one embodiment, the length L3 of the tool 404 is about 105.7 millimeters. The length L3 of the tool 404 is important, because it allows the surgeon to employ minimally invasive approaches and to reach areas difficult to access. The length L3 of the tool 404 also enhances visibility of the surgical target site and forgoes the need to cut soft tissue surrounding the target bone or soft tissue, thereby reducing post-operative swelling.

In an embodiment, the tool 404 includes a first section 406 and a second section 408. The first section 408 is configured to be coupled to the transducer assembly 102 (FIG. 2), whereas the second section 408 has a free end and is connected to the first section 408. The first and second sections 406 and 406 can be made of different materials. In one embodiment, the first section 406 can be substantially similar or identical to the first section 206 shown in FIGS. 5A-5C. Hence, the first section 406 can be partly or entirely made from a titanium alloy, such as the titanium alloys described above with respect to the tool 204. The second section 408 can be substantially similar or identical to the second section 208 shown in FIGS. 5A-5C, except for its operative portion 426. For example, the section section 408 can be partly or wholly made from any suitable stainless steel, such as the stainless steel grades listed above in connection with the tool 204. Like the second section 208 shown in FIGS. 5A-5C, the second section 408 of the tool 404 can include a connection portion 418 that is directly or indirectly connected to the first section 406 and an elbow 424 that is coupled to the connection portion 418. At least part of the operative portion 426 can have an abrasive coating.

The operative portion 426 has a proximal end section 430 that is coupled to the elbow 424, and a distal end section 428. The distal end section 428 is partly or entirely coated with a suitable abrasive material. The operative portion 426 includes a support body 423 and a cutting member 425 that is carried by the support body 423. For instance, the cutting member 425 can be monolithic with the support body 423. The cutting member 425, in turn, carries at least one cutting surface 436 that is configured to vibrate and to contact a tissue body in order to cut, for instance shape or remove, the tissue body. The cutting surface 436 can be partly or entirely covered with an abrasive coating 437. The abrasive coating 437 can be made from any suitable abrasive material that is configured to cut, for instance shape or remove, a tissue body when the cutting surface 436 vibrates. Suitable abrasive materials include, but are not limited to, diamond and diamond-like carbons (DLC), such as tetrahedral amorphous carbon (ta-C). The abrasive material can have a nano-crystalline or micro-crystalline structure. In one embodiment the cutting surface 436 is coated with diamond or diamond particles. The distal end section 428 has a first end 432 that is coupled to the proximal end section 430 and a second free end 434. The second free end 434 of the distal end section 428 can coincide with the distal end 412 of the tool 404. Further, the cutting surface 436 defines a cross-sectional dimension or diameter D2. In one embodiment, the distal end section 432 has a substantially frusto-conical shape. In one embodiment, the distal end section 432 is tapered so that the cross-sectional dimension or diameter D2 decreases in a direction from the first end 432 toward the second free end 434. The tool 404 can have an irrigation fluid channel and inner threads as described above with respect to FIG. 5D.

The operation of the tool 404 is substantially similar or identical to the operation of the tool 202 described above with respect to FIGS. 5A-D. In operation, tool 404 can be used for mandible and skull based procedures, transnasal and transorbital approaches, lateral decompression, and full ramus osteotomy. Thus, the tool 404 can be used in neurosurgery and cranio-maxillofacial (CMF) surgery. For example, in neurosurgery, the tool 404 can be used for decompression of neurovascular structures (i.e., optic nerve), frontal craniotomy, and a transorbital approach. The tool 404 can also be used to gain access the following anatomies, namely: the anterior clinoid process, dorsum sellae, internal acoustic meatus, posterior cranial fossa, middle cranial fossa, groove for sigmoid sinus, superorbital fissure, optical canal, cribriform plate, crista galli, clinoid process, lesser wing of sphenoid, and greater wing of sphenoid. In CMF surgery, the tool 404 can also be used to gain access the following anatomies, namely coronoid process, condyle, ramus, angle, groove for external maxillary artery, maxillary frontal process, anterior lacrimal crest, lacrimal groove, orbital surface, maxillary tuberosity, zygomatic process, alveolar process, nasal bone, vomer bone, sphenoid, and palatine bones.

Figure 8:
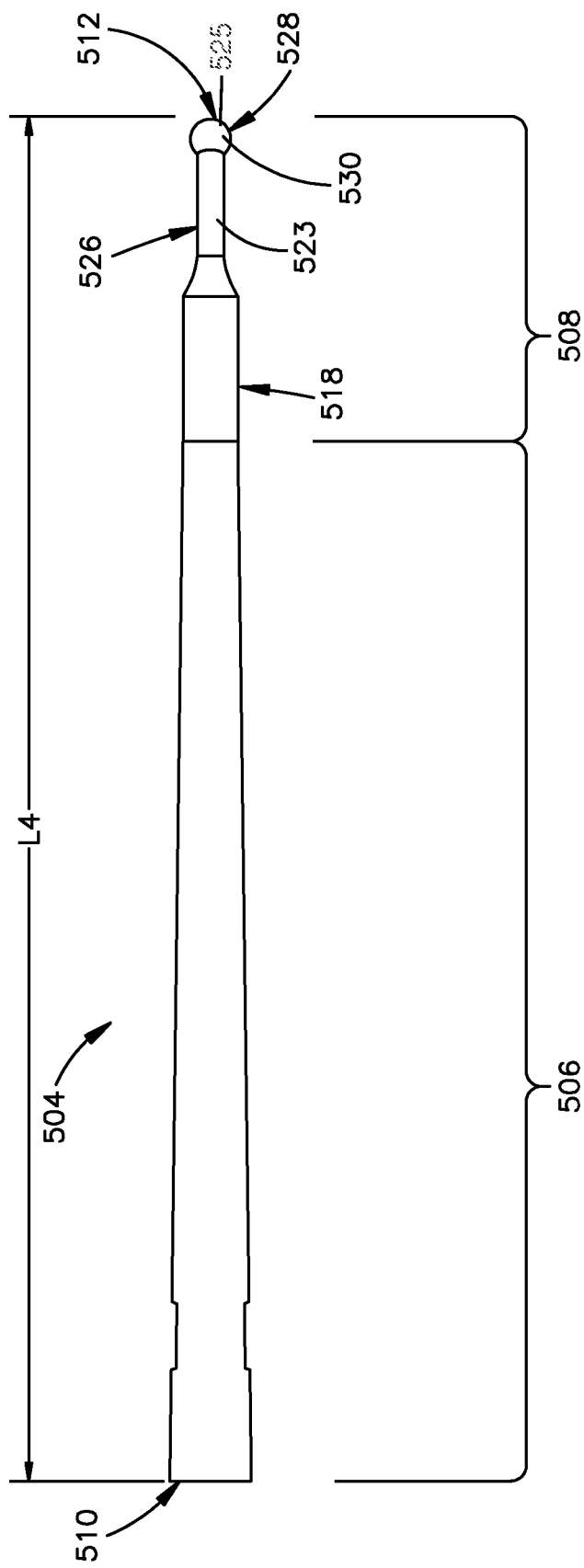
FIG. 8 is a side elevation view of a tool in accordance with an embodiment of the present disclosure.

With reference to FIG. 8, an embodiment of a tool 504 can be removably coupled to the transducer assembly 102 (FIG. 2). The tool 504 is substantially similar to the tool 204 described above with respect to FIGS. 5A-C, and defines a first or proximal end 510 and a second or distal end 512. For instance, the tool 504 can a length L4 defined between the proximal end 510 and the distal end 512. The length L4 can be substantially similar or identical to the length L1 described above with respect to FIGS. 5A-5C. In the depicted embodiment, the length L4 of the tool 504 is greater than about 80 millimeters. In an embodiment, the length L4 of the tool 504 ranges between about 20 millimeters and 120 millimeters. In one embodiment, the length L4 of the tool 504 is about 105.7 millimeters. The length L4 of the tool 504 is important, because it allows the surgeon to employ minimally invasive approaches and to reach areas difficult to access. The length L3 of the tool 404 also enhances visibility of the surgical target site and forgoes the need to cut soft tissue surrounding the target bone or soft tissue, thereby reducing post-operative swelling.

In an embodiment, the tool 504 includes a first section 506 and a second section 508. The first section 508 is configured to be coupled to the transducer assembly 102 (FIG. 2), whereas the second section 508 is connected to the first section 508. The first and second sections 506 and 506 can be made of different materials. In one embodiment, the first section 506 can be substantially similar or identical to the first section 206 shown in FIGS. 5A-5C. Thus, the first section 506 can be partly or wholly made from a titanium alloy, such as the titanium alloys described above in connection with the tool 204. The second section 508 can be substantially similar or identical to the second section 208 shown in FIGS. 5A-5C, except for its operative portion 526. For example, the second section 508 can be partly or wholly made from any suitable stainless steel, such as the stainless steel described above in connection with the tool 204. Like the second section 208 shown in FIGS. 5A-5C, the second section 408 of the tool 404 can include a connection portion 518 that is directly or indirectly connected to the first section 506. Although the operative portion 526 of the depicted embodiment does not include an elbow, it is envisioned that the operative portion 524 can include an elbow, such as the elbow 224 described above in connection with FIGS. 5A-5C.

The operative portion 526 includes a support body 523 and a cutting member 528 that is carried by the support body 523. For instance, the cutting member 528 can be monolithic with the support body 523. The cutting member 528, in turn, carries at least one cutting surface 525 that is configured to vibrate and to contact a tissue body in order to cut, for instance shape or remove, the tissue body. The cutting member 528 can be located at the distal end 512 of the tool 504. In an embodiment, the cutting member 528 can have a substantially ellipsoidal shape. As used herein, the term "ellipsoidal" includes, but is not limited to, the following terms, namely: spherical, oblate spheroidal, prolate spheroidal, and a scalene ellipsoidal. Hence, the cutting member 528 can have a substantially spherical shape, a substantially oblate spheroidal shape, a substantially prolate spheroidal shape, or a substantially scalene ellipsoidal. The cutting surface 525 is partly or entirely coated with a suitable abrasive material. At least a portion of the cutting member 528 can be coated with an abrasive coating 530. The abrasive coating 530 can be partly or entirely made from an abrasive material suitable to cut, for instance shape or remove, a tissue body when the cutting surface 525 vibrates at a predetermined frequency. Suitable abrasive materials include, but are not limited to, diamond and diamond-like carbons (DLC), such as tetrahedral amorphous carbon (ta-C). The abrasive material can have a nano-crystalline or micro-crystalline structure. The abrasive coating 530 can be about 107 micrometers (μm) thick. The tool 504 can include an irrigation fluid channel and inner threads as described above with respect to FIGS. 5D.

The operation of the tool 504 can be substantially similar or identical to the operation of the tool 204 described above with respect to FIGS. 5A-C. In operation, tool 504 can be used for mandible and skull based procedures, transnasal and transorbital approaches, lateral decompression, and full ramus osteotomy. Thus, the tool 504 can be used in neurosurgery and cranio-maxillofacial (CMF) surgery. For example, in neurosurgery, the tool 504 can be used for decompression of neurovascular structures (i.e., optic nerve), frontal craniotomy, and a transorbital approach. The tool 504 can also be used to gain access the following anatomies, namely: the anterior clinoid process, dorsum sellae, internal acoustic meatus, posterior cranial fossa, middle cranial fossa, groove for sigmoid sinus, superorbital fissure, optical canal, cribriform plate, crista galli, clinoid process, lesser wing of sphenoid, and greater wing of sphenoid. In CMF surgery, the tool 504 can also be used to gain access the following anatomies, namely coronoid process, condyle, ramus, angle, groove for external maxillary artery, maxillary frontal process, anterior lacrimal crest, lacrimal groove, orbital surface, maxillary tuberosity, zygomatic process, alveolar process, nasal bone, vomer bone, sphenoid, and palatine bones.

Figure 9A:
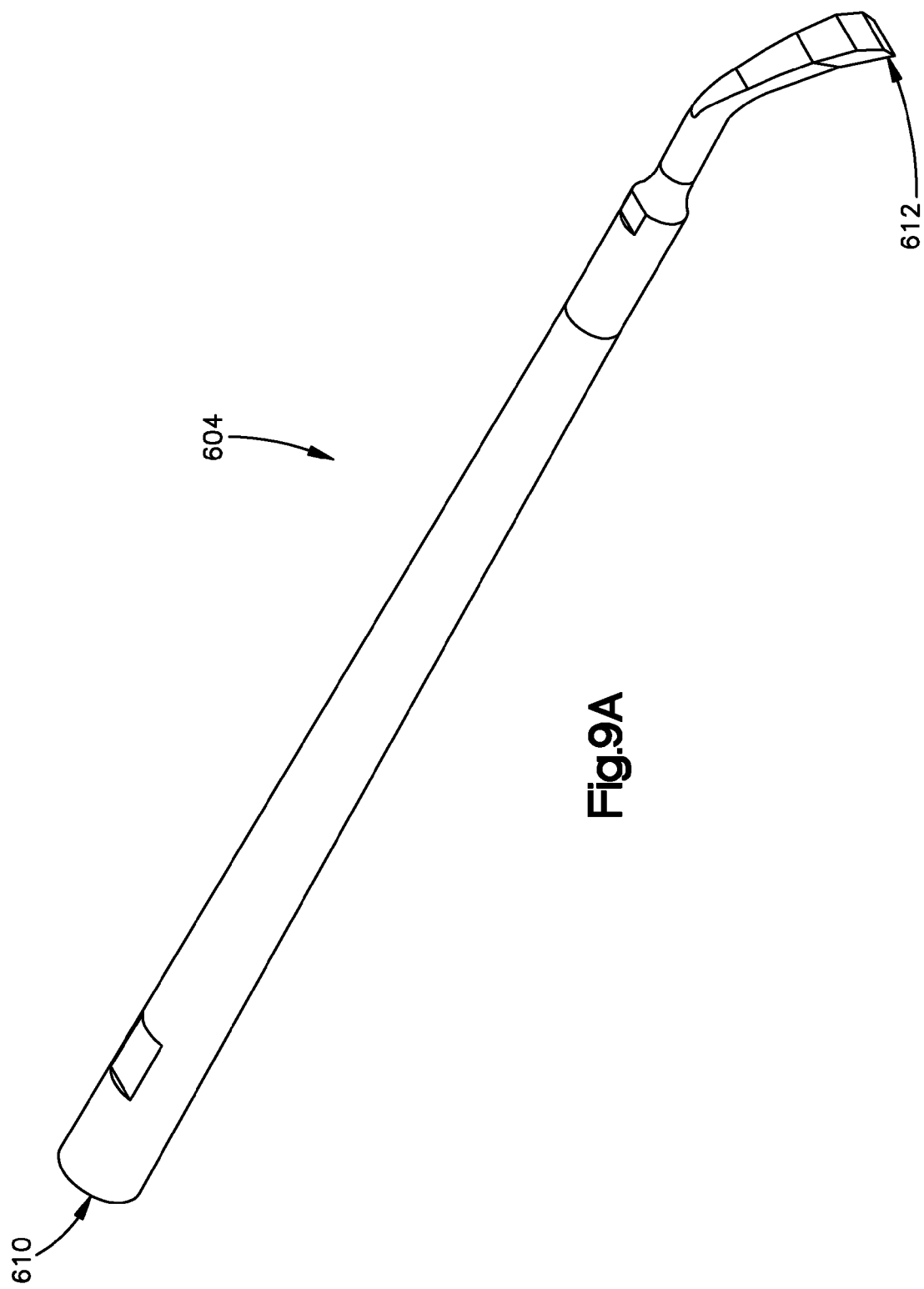
FIG. 9A is a perspective view of a tool in accordance with an embodiment of the present disclosure.
Figure 9B:
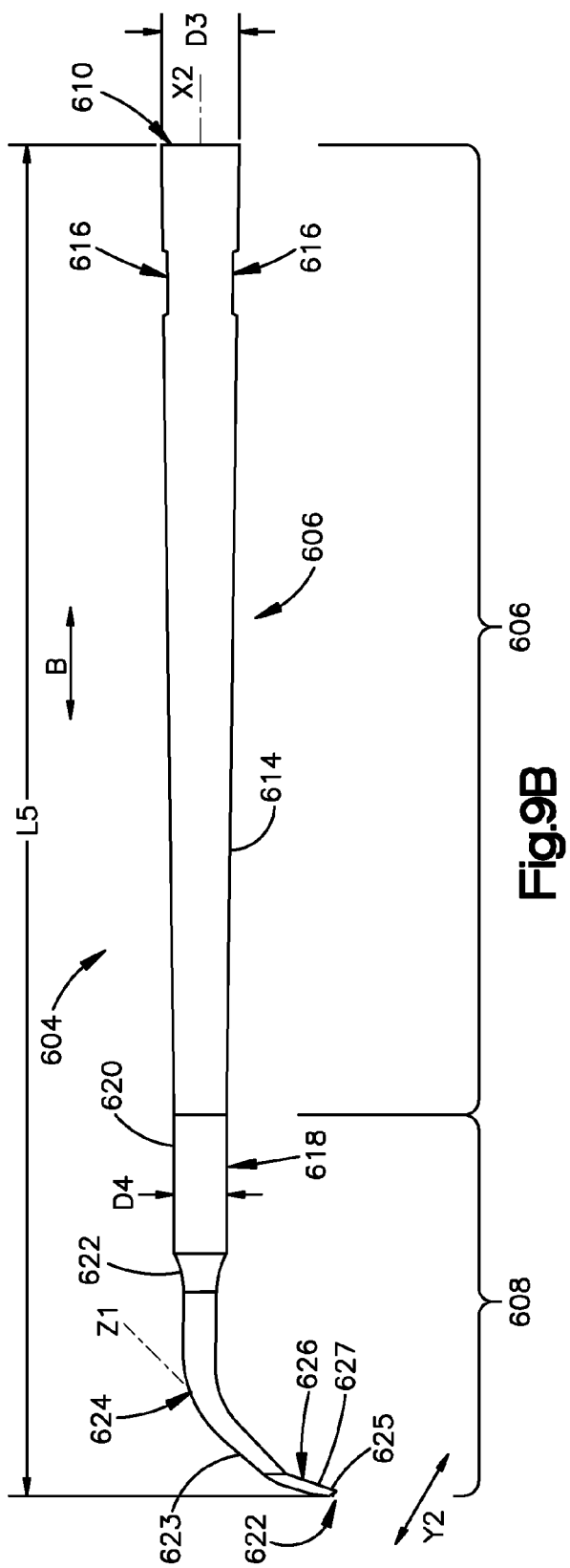
FIG. 9B is a side elevation view of the tool illustrated in FIG. 9A.
Figure 9C:
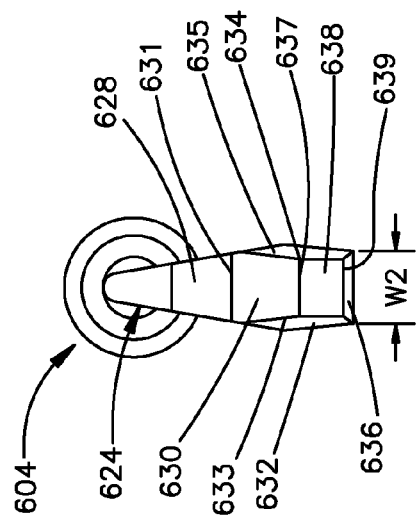
FIG. 9C is a top view of the tool illustrated in FIG. 9A.
Figure 11A:
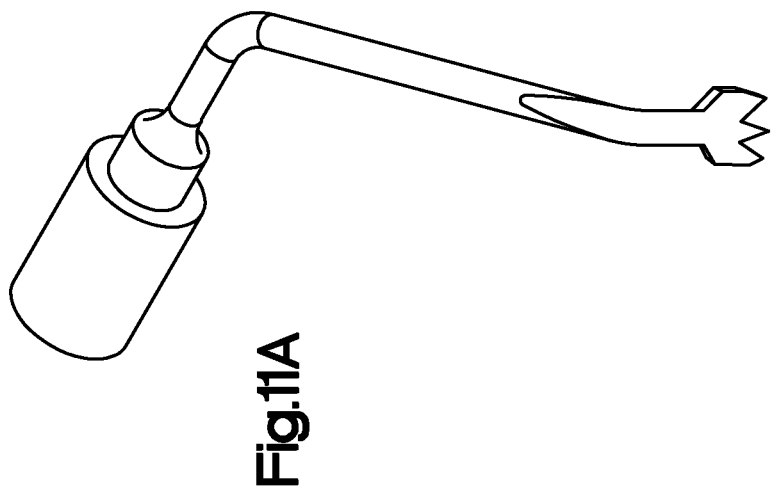
Figure 11B:
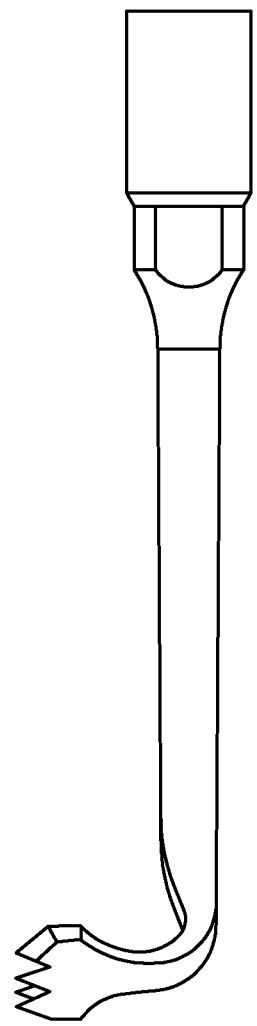
Figure 11C:
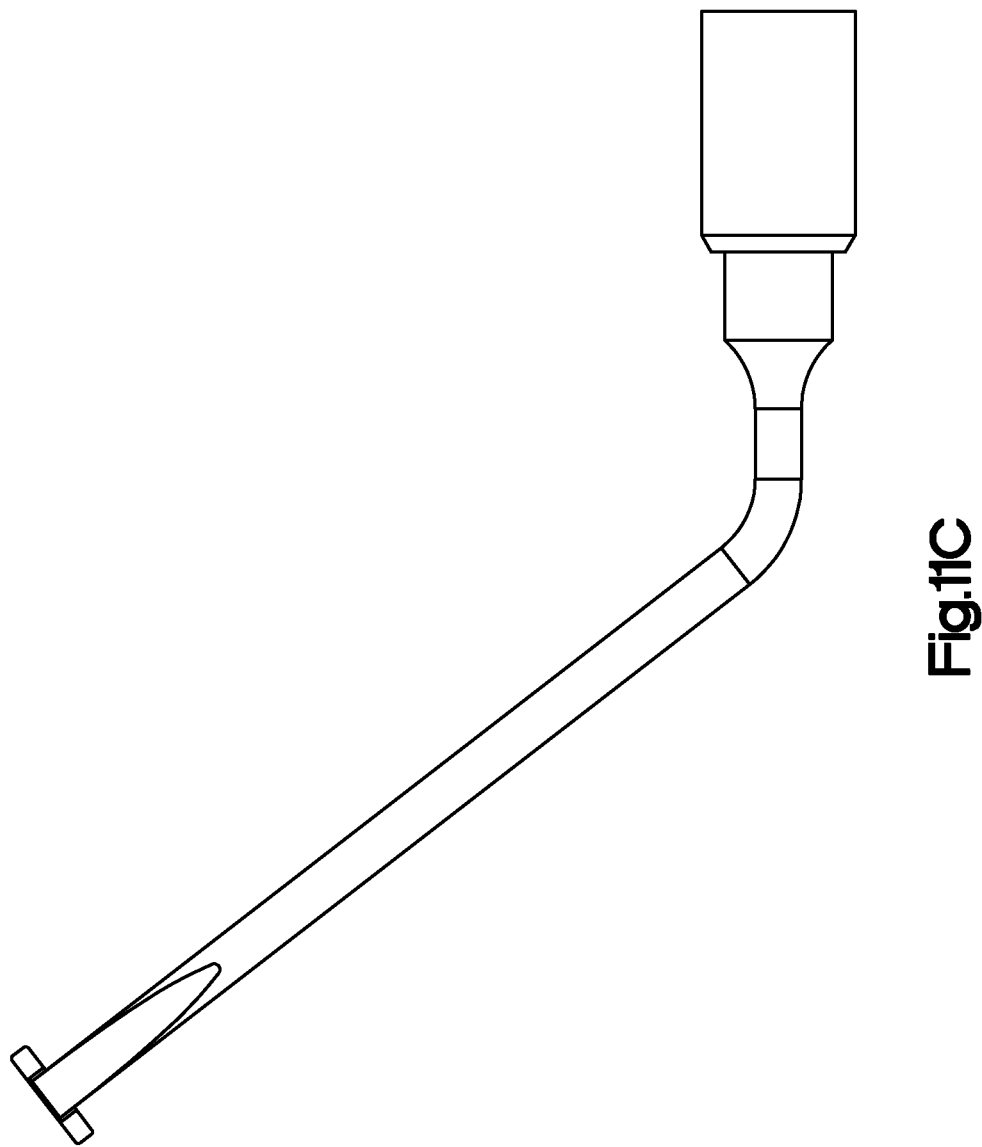
Figure 16:
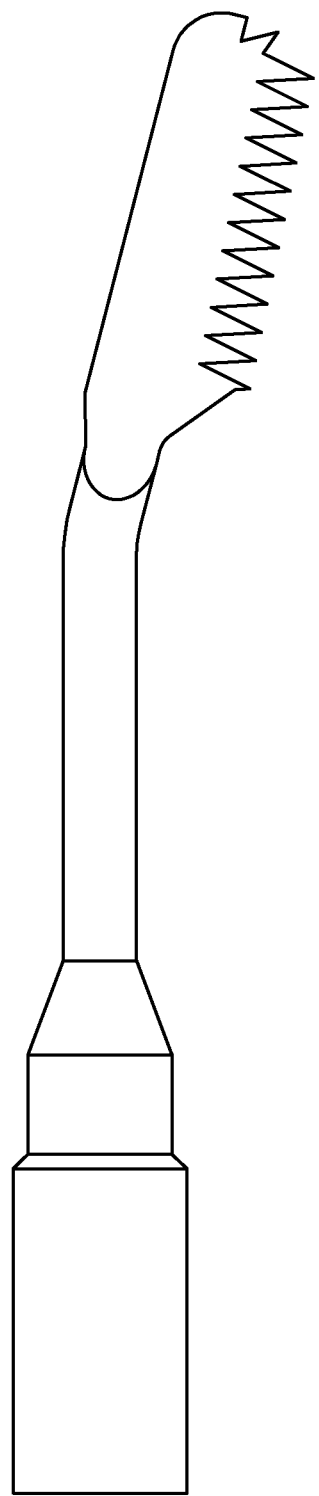

With reference to FIGS. 9A-9C, an embodiment of a tool 604 is configured to be removably coupled to the transducer assembly 102, and defines a first or proximal end 610 and a second or distal end 612. The tool 604 has a length L5 defined between the proximal end 610 and the distal end 612 along a longitudinal direction indicated by arrows B. The tool 604 is substantially similar to the tool 204 described with respect to FIGS. 5A-5C, except for the operative portion 626. In the depicted embodiment, the length L5 of the tool 604 is greater than about 80 millimeters. In an embodiment, the length L5 of the tool 604 ranges between about 20 millimeters and about 120 millimeters. In one embodiment, the length L5 of the tool 604 is about 105.7 millimeters. The length L5 of the tool 604 is important, because it allows the surgeon to employ minimally invasive approaches and to reach areas difficult to access. The length L5 of the tool 604 also enhances visibility of the surgical target site and forgoes the need to cut soft tissue surrounding the target bone or soft tissue, thereby reducing post-operative swelling.

With continued reference to FIGS. 9A-9C, in an embodiment, the tool 604 includes a first section 606 and a second section 608. The first section 606 is configured to be coupled to the transducer assembly 102 (FIG. 2), whereas the second section 608 is connected to the first section 606. The first and second sections 606 and 608 can be made from different materials. In an embodiment, the first section 606 can be substantially similar or identical to the first section 206 shown in FIGS. 5A-5C. The first section 606 can be partly or wholly made from a titanium alloy, such as the titanium alloys described above in connection with the tool 204. The first section 606 of the tool 604 extends in a direction along a longitudinal axis X2 and has an outer surface 614. The outer surface 614 of the first section 606 defines a cross-sectional dimension or diameter D3. The first section 606 can be tapered so that the cross-sectional dimension or diameter D3 decreases in a direction from the proximal end 610 toward the distal end 612. Thus, the first section 606 can have a substantially frusto-conical shape. The cross-sectional dimension or diameter D3 is less than cross-sectional dimension or diameter of conventional tools to allow the surgeon to reach difficult areas to access. For example, the first section 206 can have a maximum diameter of about 5.8 millimeters.

With continued reference to FIGS. 9A-9C, the first section 606 can define one or more recesses 616 that extend into the outer surface 614. The recesses 616 are configured and sized to allow a holding tool, such as a wrench, to securely hold the tool 604. During assembly, a user can place a portion of the holding tool, such as a wrench, in the recesses 616 to hold the tool 604. The user can also use the holding tool to turn the tool 604 and thereby disconnect the tool 604 from the transducer assembly 104. In an embodiment, the tool 604 defines two identical recesses 614 disposed in a diametrically-opposed relationship to each other.

With continued reference to FIGS. 9A-9C, the second section 608 can be substantially similar or identical to the section 208 shown in FIGS. 5A-5C, except for its operative operation 626. For example, the second section 608 can be partly or entirely made from any suitable stainless steel, such as the stainless steel described above in connection with the tool 204. The second section 608 can include a connection portion 618 coupled to the first section 606. The connection portion 618 is elongate along the longitudinal direction B and defines an outer surface 620. The outer surface 620 of the connection portion 618 defines a cross-sectional dimension or diameter D4. The outer surface 620 can be tapered so that the cross-sectional dimension or diameter decreases in a direction toward the distal end 612. Thus, the connection portion 618 can have a substantially frusto-conical shape.

With continued reference to FIGS. 9A-9C, the second section 608 can further include a shoulder 622 coupled to the connection portion 618. The shoulder 622 can be connected to an elbow 624. The second section 608 can further include an operative section 626 directly or indirectly coupled to the elbow 624. The operative portion 626 is configured to contact a tissue body in order to cut, for instance shape or remove, such tissue body. In the depicted embodiment, the operative portion 626 is elongate along an axis Z2 that is oriented at an oblique angle relative to the longitudinal axis X2. At least part of the operative portion 626 can have a substantially flat or planar configuration. In one embodiment, the operative portion 626 can be substantially shaped as a scalpel.

With continued reference to FIGS. 9A-9C, the operative portion 626 includes a support body 623 and a cutting member 625 that is carried by the support body 623. For instance, the cutting member 625 can be monolithic with the support body 623. The cutting member 625, in turn, carries at least one cutting surface 627 that is configured to vibrate and to contact a tissue body in order to cut, for instance shape or remove, the tissue body. In accordance with one embodiment, the cutting member 625 can define a first top cutting surface 628 and a second top cutting surface 630. The first top surface 628 can contact the second top surface 630 so that the first top surface 628 and the second top surface 630 cooperate to define a first cutting edge 631. The first top surface 628 can be directly or indirectly connected to the second top surface 630. The cutting member 625 can further define a first side cutting surface 632, a second side cutting surface 634, and a bottom cutting surface 636. The first side cutting surface 632 can extend from the second top surface 630 in a direction toward the bottom surface 636. Moreover, the first side cutting surface 632 can contact the second top cutting surface 630 such that the first side cutting surface 632 and the second top cutting surface 630 cooperate to define a cutting edge 633. The second side cutting surface 634 can extend from the second top cutting surface 630 toward the bottom surface 636. The second side cutting surface 634 can contact the second top cutting surface 630 such that the second side cutting surface 634 and the second top cutting surface 630 cooperate to define a cutting edge 635. The cutting member 625 can further define a front cutting surface 638 that can extend from the second top cutting surface 630 toward the bottom surface 636. The front cutting surface 638 can contact the second top cutting surface 630 such that the front cutting surface 638 and the second top cutting surface 630 cooperate to define a cutting edge 637. The front cutting surface 638 can contact the bottom cutting surface 636 such that the front cutting surface 638 and the bottom cutting surface 636 cooperate to define a cutting edge 639. The cutting member 625 can have a width W2 defined between the first side surface 632 and the second side surface 634 along a direction that is substantially perpendicular to the longitudinal direction B. In one embodiment, the width W2 ranges between approximately 2 millimeters and approximately 5 millimeters. In an embodiment, the width W2 is approximately 3 millimeters. The width W2 described above are important because it they allow the surgeon to perform minimally invasive procedures. The tool 604 can include an irrigation fluid channel and inner threads as described above with respect to FIG. 5D.

With continued reference to FIGS. 9A-9C, the operation of the tool 604 is substantially similar or identical to the operation of the tool 204 described above with respect to FIGS. 5A-D. In operation, the tool 604 can be used for mandible and skull based procedures, transnasal and transorbital approaches, lateral decompression, contouring, osteotomy, and bone harvesting. When the tool 604 is connected to the transducer assembly 102, the transducer assembly 102 can propagates mechanical vibrations along tool 604. Specifically, when the transducer assembly 102 receives electrical energy, it converts the electrical energy into mechanical vibrations. Then, the transducer assembly 102 transmits the mechanical vibrations to the tool 604, causing at least the first section 606 to vibrate in the direction indicated by arrows B. The vibration of the first section 606 causes the operative portion 626 to vibrate in the direction indicated by arrows Y2. The operative portion 626 can then be placed in contact with a tissue body in order to cut, for instance shape or remove, such tissue body.

With continued reference to FIGS. 9A-9C, the tool 604 can be used in neurosurgery. For example, the tool 604 can be used for decompression of neurovascular structures (i.e., optic nerve), frontal craniotomy, and transorbital approach. In addition, the tool 6045 can be used to access the following anatomical structures: anterior clinoid process, dorsum sellae, Internal acoustic meatus, Posterior cranial fossa, Middle cranial fossa, groove for sigmoid sinus, superorbital fissure, optical canal, cribriform plate, crista galli, clinoid process, lesser wing of sphenoid and greater wing of sphenoid. In CMF surgery, the tool 604 can be used to access the following anatomical structures: coronoid process, condyle, ramus, angle, groove for external maxillary artery, maxillary frontal process, anterior lacrimal crest, lacrimal groove, orbital surface, maxillary tuberosity, zygomatic process, alveolar process, nasal bone, vomer bone, sphenoid, and palatine bones.

With reference to FIGS. 17A and 17B, a second section 1408 can entirely or partly replace the second section of any of the tools described in the present disclosure. The second section 1408 includes an elbow 1424 and an operative portion 1426 connected to the elbow 1424. The operative portion 1426 includes a support body 1423 and a cutting member 1425 carried by the support body 1423. The support body 1423 can be monolithically formed with the cutting member 1425. Alternatively, the support body 1423 can be a discrete component connected to the cutting member 1425. The cutting member 1425 can have a substantially flat configuration (e.g., planar configuration) and defines one or more cutting surfaces 1427. In turn, the cutting surfaces 1427 define one or more cutting edges 1428 that are configured to cut, for instance, shape or remove, a tissue body as it vibrates at a predetermined frequency range. The cutting edges 1428 can thus be sharp. The cutting member 1425 further defines a pointed free tip 1429 that is configured to cut tissue. The pointed free end 1429 can have a substantially flat configuration (e.g., planar configuration) and can be tapered.

Figure 18B:
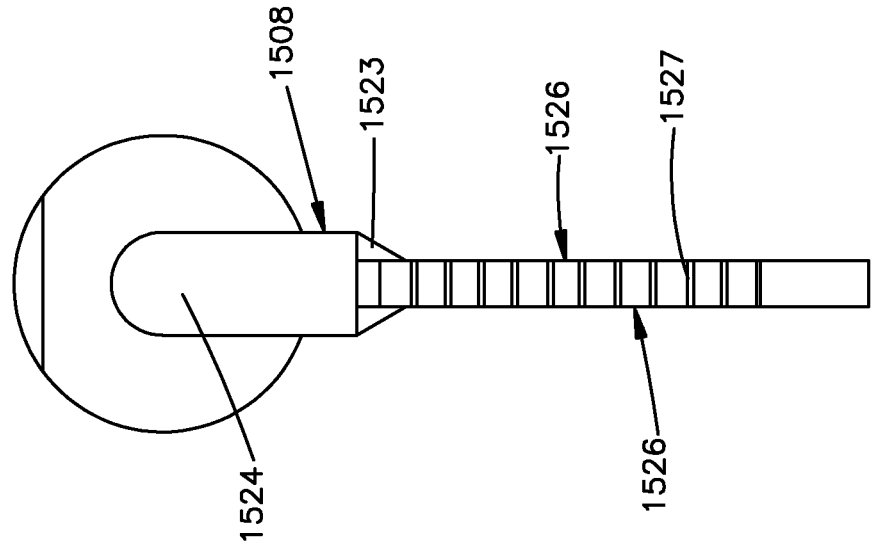
FIG. 18B is a front elevation view of the second section shown in FIG. 18A.
Figure 18A:
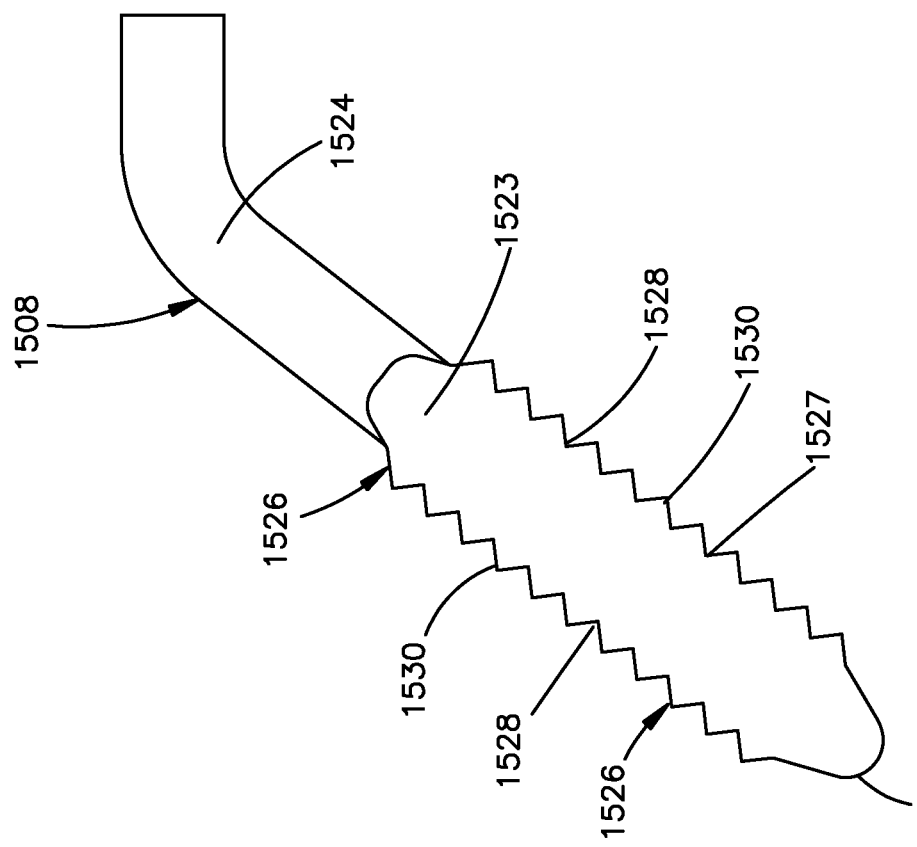
FIG. 18A is a side elevation view of a second section of a tool in accordance with an embodiment of the present disclosure.

With reference to FIGS. 18A and 18B, a second section 1508 can entirely or partly replace the second section of any of the tools described in the present disclosure. The second section 1508 includes an elbow 1524 and an operative portion 1526 connected to the elbow 1524. The operative portion 1526 includes a support body 1523 and a cutting member 1525 carried by the support body 1523. The support body 1523 can be monolithically formed with the cutting member 1525, and can have a substantially flat configuration (e.g, planar configuration). The cutting member 1525 defines one or more cutting surfaces 1527. In turn, the cutting surfaces 1427 define a pair of cutting serrated edges 1528 that are configured to cut, for instance, shape or remove, a tissue body as it vibrates at a predetermined frequency range. The cutting serrated edges 1528 can be formed by a plurality of teeth 1530 that protrude outward from the support body 1523. The cutting surfaces 1527 can further define a free pointed end 1529 that protrudes outward from the support body 1523. The free pointed end 1529 can be sharp and can have a substantially planar configuration (e.g., flat configuration). Further, the free pointed end 1529 can have a substantially tapered configuration.

With reference to FIGS. 19A and 19B, a second section 1608 can entirely or partially replace the second section of any of the tools described in the present disclosure. The second section 1608. The second section 1608 includes an elbow 1624 and an operative portion 1626. The operation portion 1626 is identical or at least substantially similar to the operative portion 926 illustrated in FIGS. 12A-12C. Thus, the description regarding the operative portion 926 applies to the operative portion 1626.

With reference to FIGS. 20A and 20B, a second portion 1708 can entirely or partially replace the second section of any of the tools described in the present disclosure. The second section 1708 includes an elbow 1724 and an operative portion 1726 connected to the elbow 1724. The operative portion 1726 includes a support body 1723 and a cutting member 1725 carried by the support body 1723. The cutting member 1725 carries at least one cutting surface 1727 that is configured to vibrate and to contact a tissue body in order to cut, for instance shape or remove, the tissue body. In an embodiment, the cutting member 1727 can define a substantially flat top surface 1730 and a substantially flat bottom surface 1732 opposite to the substantially flat top surface 1730. The top surface 1730 and the bottom surface 1732 cooperate to define first side cutting edge 1734 and a second side cutting edge 1736. The cutting member 1725 further defines a front upper cutting surface 1738 and a front lower cutting surface 1740. The front upper cutting surface 1738 and the front lower cutting surface 1740 can be substantially flat and can cooperate to define a front cutting edge 1742.

With reference to FIGS. 21A and 21B, a second section 1808 can entirely or partially replace the second section of any of the tools described in the present disclosure. The second section 1808 includes an elbow 1824 and an operative portion 1826 connected to the elbow 1824. The operative portion 1826 includes a support body 1823 and a cutting member 1825 that is carried by the support body 1823. The cutting member 1825 can have a substantially flat configuration (e.g., planar configuration) and includes one or more cutting surfaces 1827 that are configured to vibrate and to contact a tissue body in order to cut, for instance shape or remove, the tissue body. In an embodiment, the cutting member 1825 includes a top cutting surface 1828, a bottom cutting surface 1830 opposite to the top cutting surface 1828, and an outer cutting surface 1832 that interconnects the top cutting surface 1828 and the bottom cutting surface 1830. The top cutting surface 1828 and the bottom cutting surface 1830 can have a substantially flat configuration (e.g., planar configuration). The outer cutting surface 1832 can also have a substantially flat configuration (e.g., planar configuration), and can be oriented at an oblique angle relative to the top cutting surface 1828 and/or the bottom cutting surface 1830. In an embodiment, the outer cutting surface 1832 can be disposed in rounded manner around an axis 1834 that extends substantially perpendicular to the top cutting surface 1828 and/or the bottom cutting surface 1830. As used herein, the term "rounded" includes, but is not limited to, a circular, elliptical, arched, semi-circular, curved, and elliptical arch. The top cutting surface 1828 and the outer cutting surface 1832 cooperate to define a top cutting edge 1836. The top cutting edge 1836 can be disposed in a rounded manner about the axis 1834. The bottom cutting surface 1830 and the outer cutting surface 1832 cooperate to define a bottom cutting edge 1838. The bottom cutting edge 1838 can be disposed in a rounded manner about the axis 1834.

With reference to FIGS. 22A and 22B, a second section 1908 can entirely or partially replace the second section of any of the tools described in the present disclosure. The second section 1908 includes an elbow 1924 and an operative portion 1926 connected to the elbow 1924. The operative portion 1926 includes a support body 1923 and a cutting member 1925 that is carried by the support body 1923. The support body 1923 can have a substantially flat configuration (e.g. planar configuration). The cutting member 1925 can carries at least one cutting surface 1927 that is configured to vibrate and to contact a tissue body in order to cut, for example shape or remove, the tissue body. The cutting member 1925 can define more than one cutting surface 1927, such as a pair of cutting surfaces 1927, that define a cutting edge 1928. In one embodiment, the cutting member 1925 defines a serrated edge 1928 so as to define a plurality of teeth 1930 that protrude outward from the support body 1923 along a direction away from the support body 1923, which can be angularly offset with respect to a longitudinal direction 1901. In an embodiment, the teeth 1930 are spaced apart from one another along a longitudinal row in an angled direction 1903. The angled direction 1903 can be oriented at an oblique angle relative to the longitudinal direction 1901.

With reference to FIGS. 23A and 23B, a second section 2008 can entirely or partly replace the second section of any of the tools described in the present disclosure. The second section 2008 includes an elbow 2024 and an operative portion 2026 connected to the elbow 2024. The operative portion 2026 includes a support body 2023 and a cutting member 2025. The cutting member 2025 carries one or more cutting surfaces 2027 that are configured to vibrate and to contact a tissue body in order to cut, for example shape or remove, the tissue body. In an embodiment, the cutting member 2025 defines an upper cutting surface 2028, a lower cutting surface 2029 opposite to the upper cutting surface 2028, a first side cutting surface 2030, and a second cutting side surface 2031. Each of the first and second side cutting surfaces 2030 and 2031 can interconnect the upper cutting surface 2028 and the lower cutting surface 2029. The distance defined from the first side cutting surface 2030 to the second side cutting surfaces 2031 increases in a direction from the cutting member 2025 toward the elbow 2024 so as to define a tapered cutting member 2025. The first and second side cutting surfaces 2030 and 2031 cooperate to define a front sharp edge 2032.

With reference to FIGS. 24A, 24B, and 25 a second section 2108 can entirely or partially replace the second section of any of the tools described in the present disclosure. The second section 2108 includes an elbow 2124 and an operative portion 2126 directly or indirectly connected to the elbow 2124. The operative portion 2126 includes a support body 2123 and a cutting member 2125 that is carried by the support body 2125. The cutting member 2125 carries at least one cutting surface 2127 that is configured to vibrate and to contact a tissue body in order to cut (e.g., shape or remove) the tissue body. The cutting member can define more than one cutting surface 2127, such as a pair of cutting surfaces 2127, that define a cutting edge 2128. The cutting edge 2128 can be sharp and can be serrated or non-serrated. In one embodiment, the cutting member 2125 can include a serrated edge 2128 so as to define a plurality of teeth 2130 that protrude outward from the support body 2125 as shown in FIG. 25. The serrated edge 2128 can define a plurality of teeth 2130 that are spaced apart from each other along or around a perimeter. This perimeter may, for example, have a round shape. As used herein, the term "round" includes, but is not limited to, the following shapes: curved, elliptical, circular, semi-circular, and oval. In an embodiment, the teeth 2130 are spaced apart from each other around a circumference. Thus, the teeth 2130 can be arranged, for example, along an annular row. Regardless of its shape or arrangement, the serrated edge 2128 is configured to cut (e.g., shape or remove) a tissue body as it vibrates.

With reference to FIGS. 25A and 25B, a second section 2208 can entirely or partially replace the second section of any of the tools described in the present disclosure. The second section 2208 includes a first elbow 2224, a second elbow 2221, and a connecting member 2282, such as a rod, connected between the first elbow 2224 and the second elbow 2221. The first elbow 2224 changes the direction of the second section 2208 from a first direction to a second direction as indicated by arrow 2201. The second section 2208 further includes an operative portion 2226 directly or indirectly connected to the second elbow 2221. The operative portion 2226 includes a support body 2223 and a cutting member 2225 that is carried by the support body 2223. For instance, the cutting member 2225 can be monolithic with the support body 2223. The cutting member 2225, in turn, carries at least one cutting surface 2227 that is configured to vibrate and to contact tissue body in order to cut, for instance, shape or remove, the tissue body. The cutting surfaces 2227 can define at least one cutting edge 2228 that is configured to cut, for instance shape or remove, a tissue body as it vibrates at a predetermined frequency. The cutting edge 2228 can be sharp and can be serrated or non-serrated. In the depicted embodiment, the cutting member 2225 defines a serrated cutting edge 2228 so as to define a plurality of teeth 2230 that protrude outward from the support body 2223 along a direction away from the second elbow 2221. The teeth 2230 of the cutting member 2225 are spaced from each other along a row direction indicated by arrow 2203.

With reference to FIGS. 26A and 26B, a second section 2308 can entirely or partially replace the second section of any of the tools described in the present disclosure. The second section 2308 includes a first elbow 2324, a second elbow, 2321, and a connection member 2382, such as a rod, connected between the first elbow 2324 and the second elbow 2321. The second section 2308 is substantially similar to the second section 2208 illustrated in FIGS. 25A and 25B. However, the first elbow 2324 changes the direction of the second section 2308 from a first direction to a second direction as indicated by arrow 2301. The direction indicated by arrow 2301 is opposite to the direction indicated by arrow 2201 in FIG. 26B. The second section 2308 further includes an operative portion 2326 directly or indirectly connected to the second elbow 2321. The operative portion 2326 includes a support body 2323 and a cutting member 2325 that is carried by the support body 2323. For instance, the cutting member 2325 can be monolithic with the support body 2323. The cutting member 2325, in turn, carries at least one cutting surface 2327 that is configured to vibrate and to contact tissue body in order to cut, for instance, shape or remove, the tissue body. The cutting surfaces 2327 can define at least one cutting edge 2328 that is configured to cut, for instance shape or remove, a tissue body as it vibrates at a predetermined frequency. The cutting edge 2328 can be sharp and can be serrated or non-serrated. In the depicted embodiment, the cutting member 2325 defines a serrated cutting edge 2328 so as to define a plurality of teeth 2330 that protrude outward from the support body 2323 along a direction away from the second elbow 2321. The teeth 2330 of the cutting member 2325 are spaced from each other along a row direction indicated by arrow 2303.

With reference to FIGS. 28A and 29B, an embodiment of a tool 2404 can be removably coupled to the transducer assembly 102 (FIG. 2). The tool 2404 is similar to the tool 404 described above with respect to FIG. 7. Like the tool 404, the tool 2404 includes a first section 2406 configured to be coupled to the transducer assembly 102 (FIG. 2) and a second section 2408 that is connected to the first section 2406. The first section 2406 and the second section 2408 can be made of different materials as discussed above with respect to the embodiment illustrated in FIG. 7. The first section 2406 is elongate along a longitudinal direction 2401. The second section 2408 includes a connection portion 2418, such as a rod, that is connected to the first section 2406, an elbow 2424 that is coupled to the connection portion 2418, and an operative portion 2426 that is connected to the elbow 2424. A portion of the second section 2408 can be elongate along the longitudinal direction 2401; however, the elbow 2424 changes the direction of the second section 2408 such that the operative portion 2426 is elongate along an angled direction 2403. The angled direction 2403 is oriented at an oblique angle relative to the longitudinal direction 2401. The elbow 2424 can define a predetermined curvature or even a substantially right angle. The operative portion 2426 includes a support body 2423 that is connected to the elbow 2424, and a cutting member 2425 that is carried by the support body 2423. The cutting member 2425 defines at least one cutting surface 2436. The cutting surface 2436 is configured to vibrate and to contact a tissue body in order to cut (e.g., shape or remove) the tissue body. The cutting surface 2436 can be entirely or partly covered with an abrasive coating 2437. The abrasive coating 2437 can be made of any suitable abrasive material such as diamond particles. The cutting member 2425 can have a substantially spherical shape or any other ellipsoidal shape. As used herein, the term "ellipsoidal" includes, but is not limited to, the following terms, namely: spherical, oblate spheroidal, prolate spheroidal, and a scalene ellipsoidal. Hence, the body 328 can have a substantially spherical shape, a substantially oblate spheroidal shape, a substantially prolate spheroidal shape, or a substantially scalene ellipsoidal.

Figure 34B:
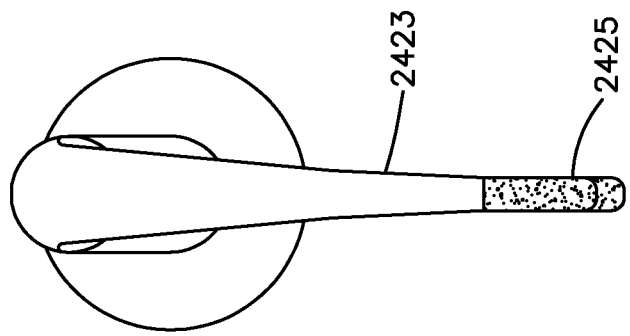
FIG. 34B is front elevation view of the second section shown in FIG. 34A.
Figure 34A:
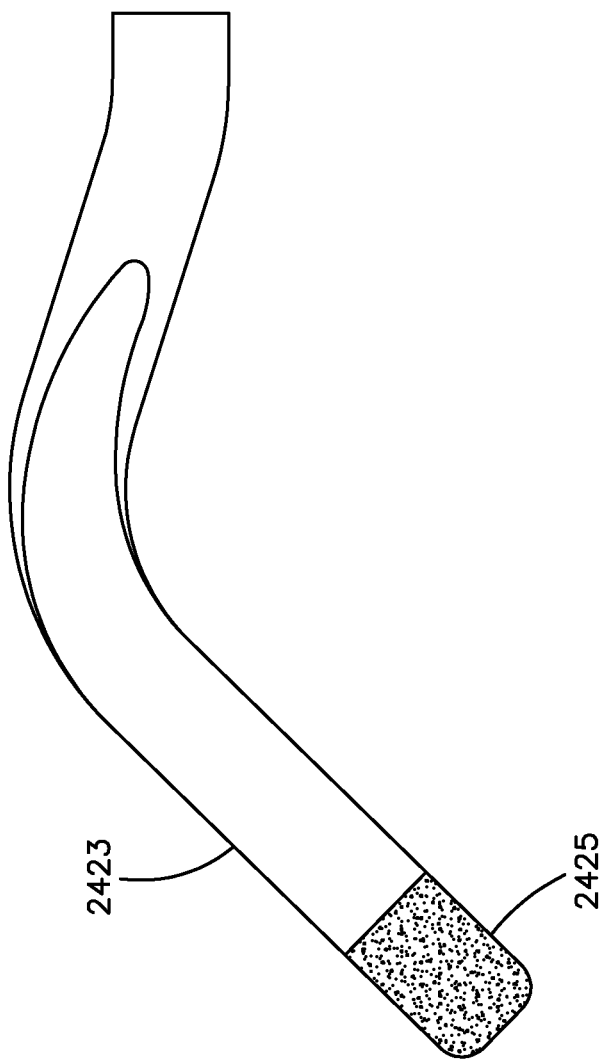
FIG. 34A is a side elevation view of a second section of a tool in accordance with an embodiment of the present disclosure.

The second section 2408 can have different shapes and features as illustrated in FIGS. 29A-48B. The embodiments shown in FIGS. 29A-48B include the abrasive coating 2437. For example, the cutting member 2425 can have an arched-shape and the abrasive coating 2437 can cover the cutting member 2425 and at least a portion of the elbow 2424 as shown in FIGS. 29A and 29B. As seen in FIGS. 30A and 30B, the cutting member 2425 can be substantially spherical but have a different size as the size of the cutting member shown in FIGS. 28A and 28B. As illustrated in FIGS. 31A and 31B, the cutting member 2425 can be spoon-shaped, and the abrasive coating 2437 can partly cover the cutting surface 2436. As depicted in FIGS. 32A and 32B, the support body 2423 can be tapered so that its cross-section dimension (e.g., diameter) can decrease in a direction from the cutting member 2425 toward the elbow 2424. As shown in FIGS. 33A and 33B, the cutting member 2425 can have substantially cylindrical portion 2425a and a substantially hemispherical end 2425b. As seen in FIGS. 34A and 34B, the support body 2423 and the cutting member 2425 can have a substantially flat configuration (e.g., planar configuration).

Figure 35B:
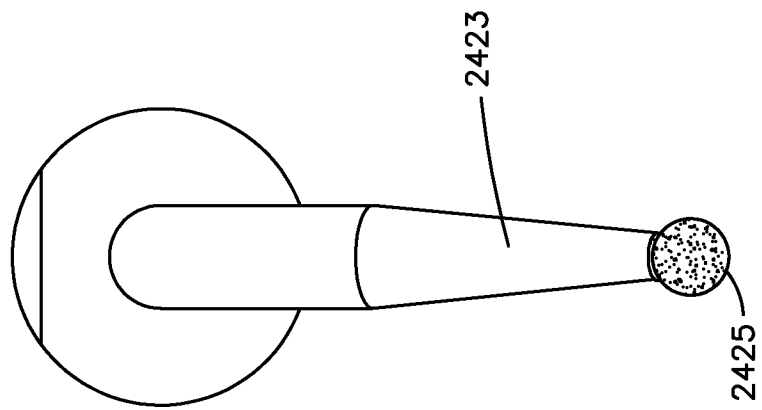
FIG. 35B is front elevation view of the second section shown in FIG. 35A.
Figure 35A:
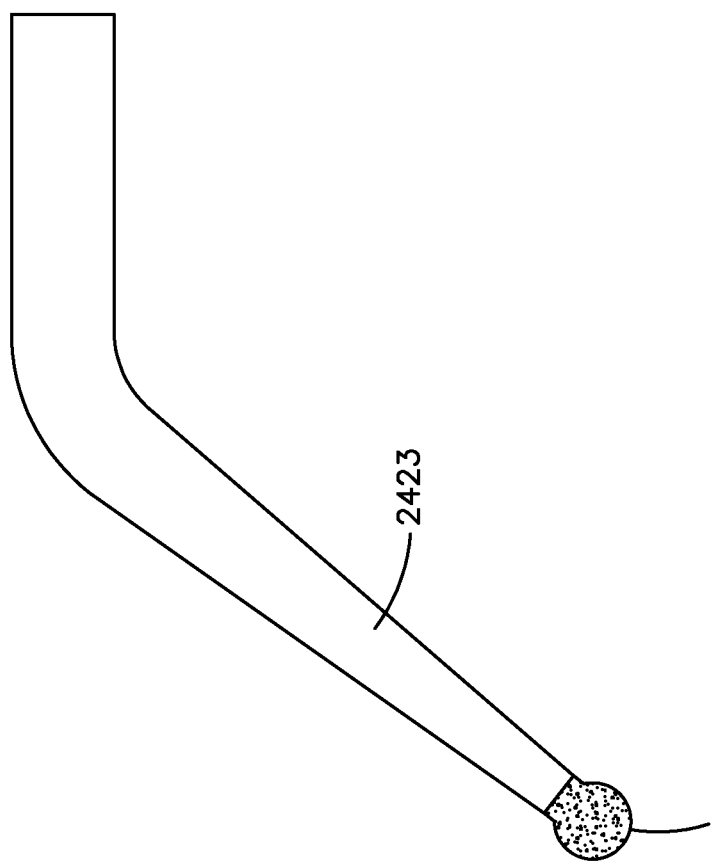
FIG. 35A is a side elevation view of a second section of a tool in accordance with an embodiment of the present disclosure.
Figure 37B:
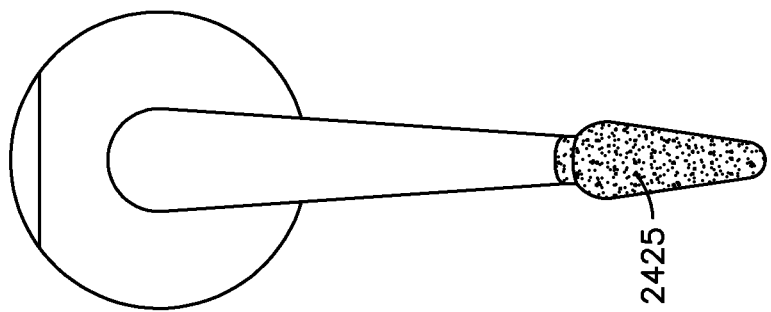
FIG. 37B is front elevation view of the second section shown in FIG. 37A.
Figure 37A:
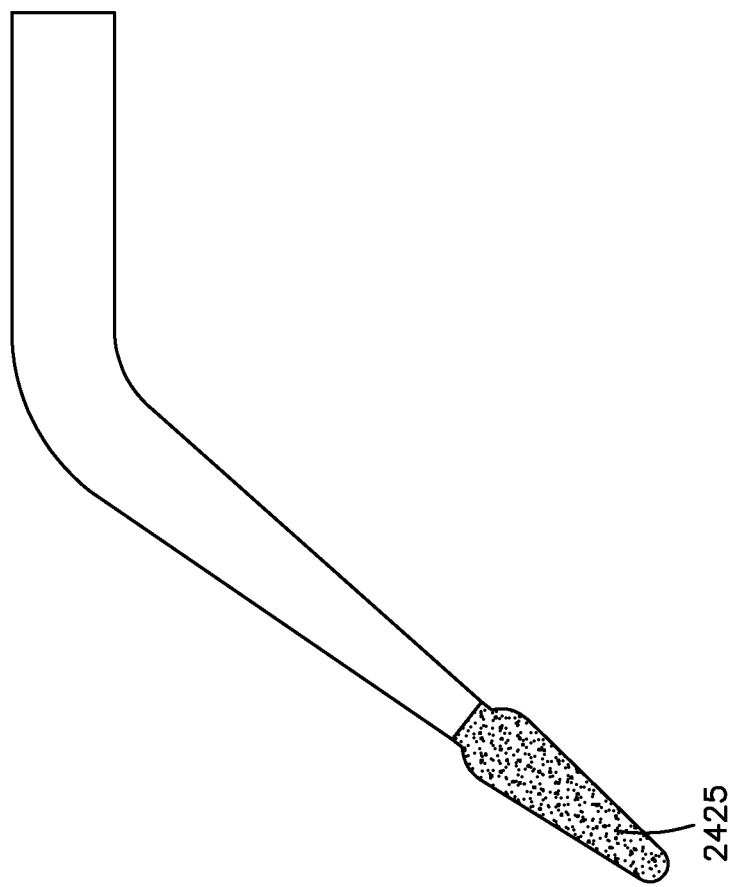
FIG. 37A is a side elevation view of a second section of a tool in accordance with an embodiment of the present disclosure.

As shown in FIGS. 35A and 35B, the support body 2423 and the cutting member 2425 can have different sizes as the sizes of the embodiments described above. As shown in FIGS. 36A and 36B, the cutting member 2425 can be a projection that protrudes from the support body 2423, and that is significantly smaller than the support body 2423. As seen in FIGS. 37A and 37B, the cutting member 2425 can have a substantially oblong shape. As shown in FIGS. 38A and 38B, the cross-sectional dimension (e.g., diameter) of the cutting member 2425 can be greater than the cross-sectional dimension (e.g. diameter) of the support body 2423. As seen in FIGS. 39A and 39B, both the cutting member 2425 and the support body 2423 can be tapered such that the cross-sectional dimensions (e.g., diameters) of the cutting member 2425 and the support member 2423 decreases in a direction from the cutting member 2425 toward the elbow 2424.

Figure 42B:
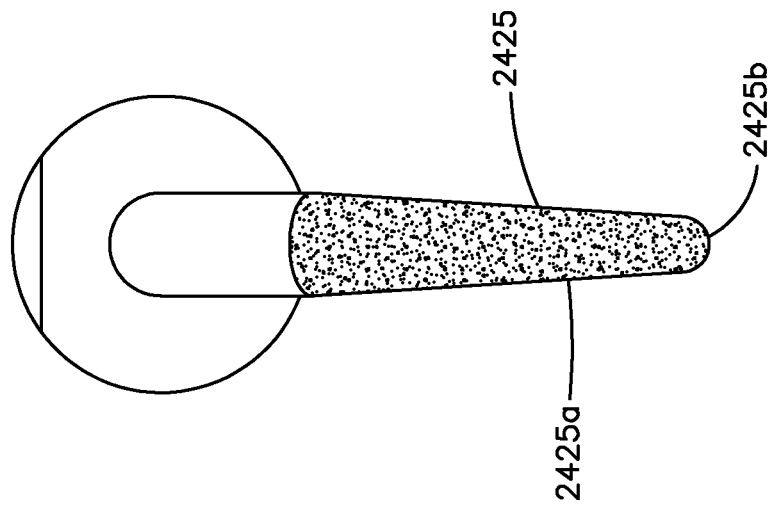
FIG. 42B is front elevation view of the second section shown in FIG. 42A.
Figure 42A:
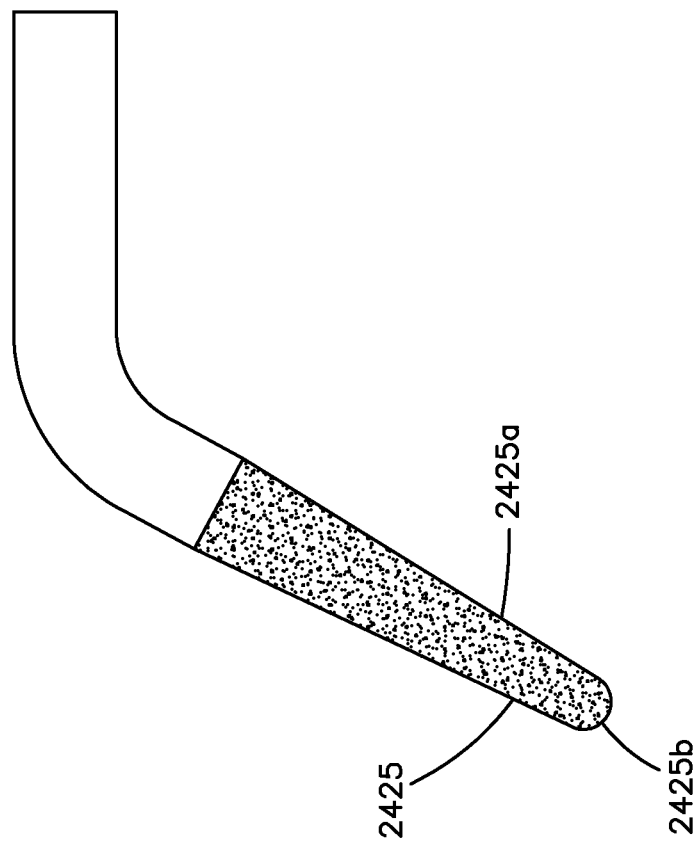
FIG. 42A is a side elevation view of a second section of a tool in accordance with an embodiment of the present disclosure.
Figure 43B:
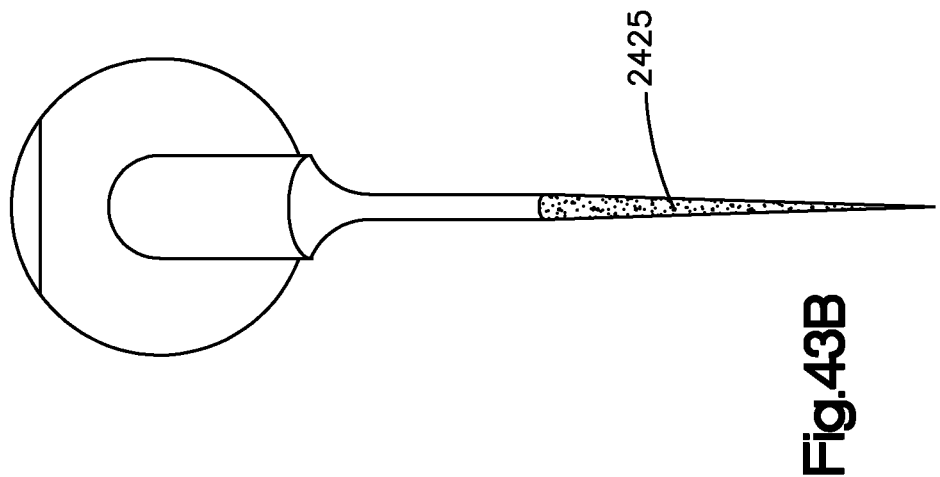
FIG. 43B is front elevation view of the second section shown in FIG. 43A.
Figure 43A:
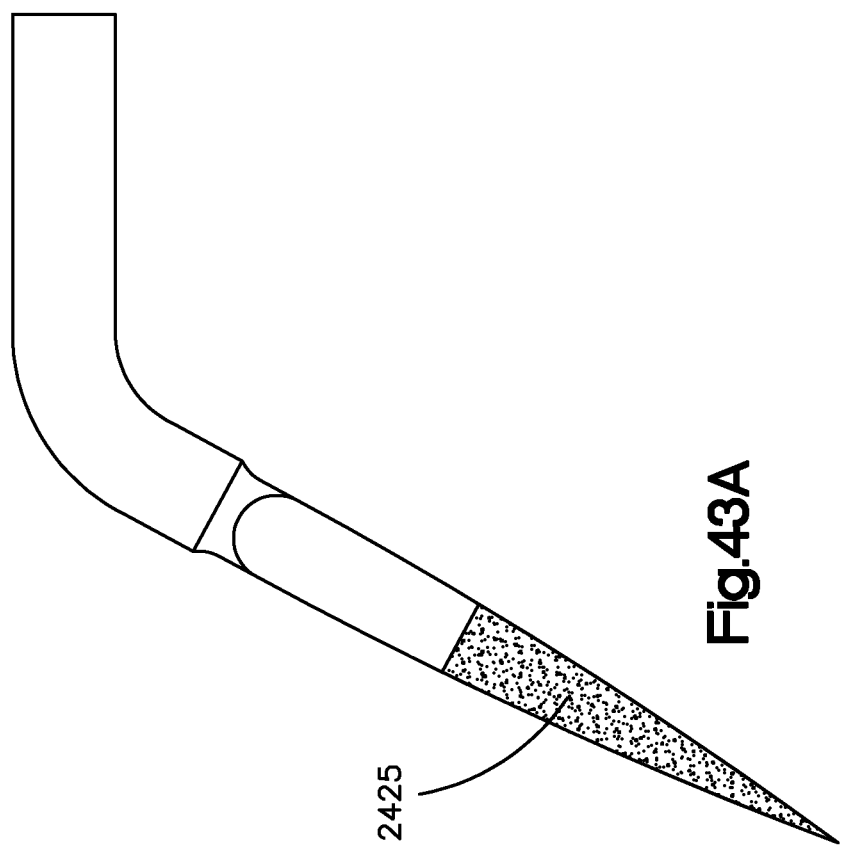
FIG. 43A is a side elevation view of a second section of a tool in accordance with an embodiment of the present disclosure.
Figure 46B:
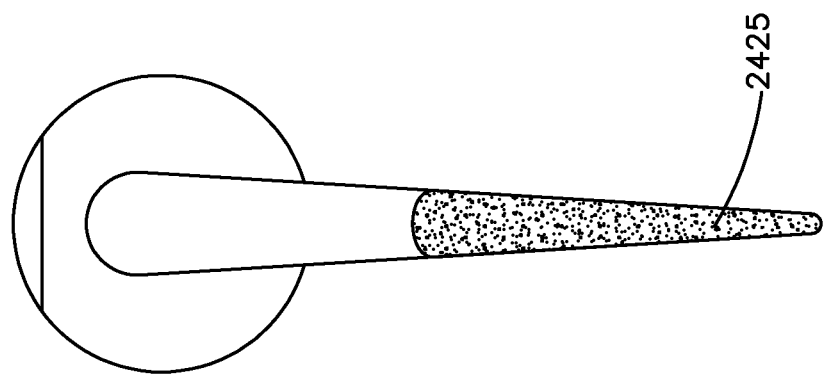
FIG. 46B is a front elevation view of the second section shown in FIG. 46A.
Figure 46A:
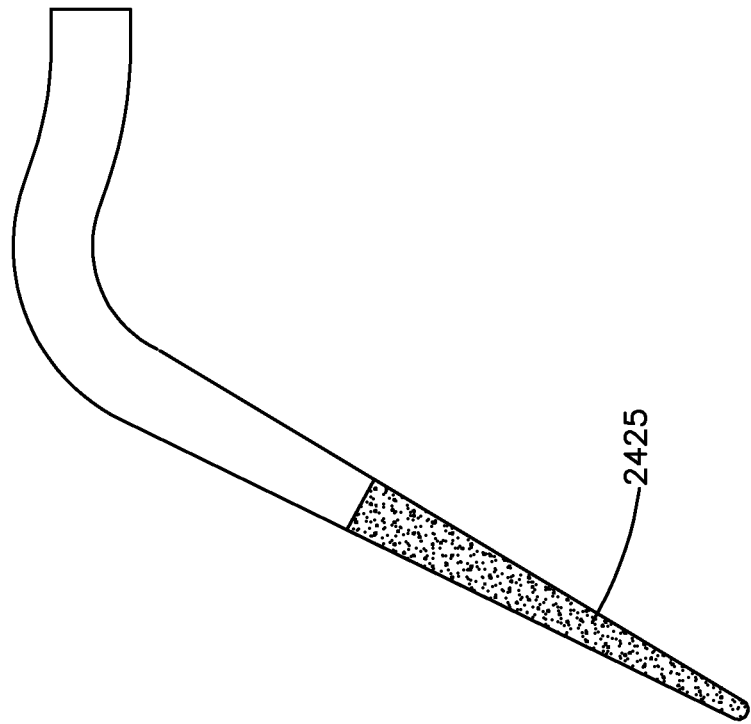
FIG. 46A is a side elevation view of a second section of a tool in accordance with an embodiment of the present disclosure.

As depicted in FIGS. 40A and 40B, the curvature of the elbow 2424 can be different than in other embodiments. In addition, the cross-sectional dimension (e.g., diameter) of at least a portion of the cutting member 2425 can be identical or substantially similar to the cross-sectional dimension (e.g., diameter) of at least a portion of the support body 2423. As seen in FIGS. 41A and 41B, the cutting member 2425 can have substantially cylindrical portion 2425a and a substantially flat end 2425b. As illustrated in FIGS. 42A and 42B, the cutting member 2425 can have substantially frusto-conical portion 2425a and a substantially hemispherical end 2425b. As shown in FIGS. 43A and 43B, the cutting member 2425 can have a substantially flat and triangular shape. As seen in FIGS. 44A and 44B, the cutting member 2425 can be significantly smaller than the support body 2423. As seen in FIGS. 45A and 45B, the support body 2423 can have a different length in comparison with the embodiment described above. In addition, the elbow 2424 can have a different curvature than other embodiments. As depicted in FIGS. 46A and 46B, the cutting member 2425 can have a frusto-conical shape, and can have a cross-sectional dimension that is less than the cross-sectional dimension of other embodiments. As shown in FIGS. 47A, 47B, 48A, and 48B, the support body 2423 can have more than one elbow 2424, and the cutting member 2425 can be arched-shape. Specifically, the support body 2423 can have a first elbow 2424a and a second elbow 2424b. The elbows 2424 can curve along different directions.

FIGS. 10A-16 illustrate various schematics of different embodiments of a tool in accordance with the present disclosure.

It should be noted that the illustrations and discussions of the embodiments shown in the figures are for exemplary purposes only, and should not be construed limiting the disclosure. One skilled in the art will appreciate that the present disclosure contemplates various embodiments. It should be further appreciated that the features and structures described and illustrated in accordance one embodiment can apply to all embodiments as described herein, unless otherwise indicated. Additionally, it should be understood that the concepts described above with the above-described embodiments may be employed alone or in combination with any of the other embodiments described above.

What is claimed:

1. A cutting system configured to cut a tissue body, the cutting system comprising:
    a transducer assembly configured to receive electrical energy and convert the received electrical energy to mechanical vibration at a predetermined frequency in a range of about 28 kHz to about 36 kHz; and
    a tool including a first end and a second end spaced from the first end along a longitudinal direction, the tool configured to be coupled to and located distally from the transducer assembly such that mechanical vibrations produced by the transducer assembly are transmitted to the tool thereby causing the tool to vibrate at the predetermined frequency, wherein the tool consists essentially of:
        a first section coupled to and distally adjacent to the transducer assembly, the first section elongate along a first axis that extends along the longitudinal direction, the first section having a proximal end defining the first end, and the first section constructed from a titanium alloy; and
        a second section coupled to and distally adjacent to the first section, the second section constructed from stainless steel having a density greater than the titanium alloy, the second section comprising an operative portion elongate along a second axis coplanar with the first axis, the second axis oriented at an oblique angle relative to the first axis, the operative portion including a support body and a cutting member located distally of the support body, the cutting member configured to cut the tissue body when the cutting member vibrates at the the predetermined frequency, the cutting member having a distal tip extending from the support body and defining the second end, the cutting member defining a serrated edge at the distal tip, the serrated edge defining teeth that protrude outwardly from the support body, each of the teeth tapering linearly and distally to a pointed tip in a plane coextensive with the first and second axes;

wherein when the tool receives the mechanical vibrations generated by the transducer assembly, the first section and at least a part of the second section vibrates back and forth along the longitudinal direction at the predetermined frequency;

wherein the tool has a length extending from the first end to the second end along the longitudinal direction between about 80 to about 120 millimeters;

wherein the cutting member is configured to vibrate at a cutting member amplitude range that is between about 300 percent to about 500 percent of a transducer assembly amplitude of the mechanical vibration produced by the transducer assembly when the first section is coupled to the transducer assembly and the transducer assembly is activated; and wherein, at the predetermined frequency and the cutting member amplitude range, the cutting member is configured to cut mineralized tissue while not cutting soft tissue.

2. The cutting system according to claim 1, further comprising a power supply electrically coupled to the transducer assembly, wherein the power supply is configured to supply electrical energy to the transducer assembly.

3. The cutting system according to claim 1, further comprising a controller electrically coupled to the transducer assembly, wherein the controller is configured to control electrically energy supplied to the transducer assembly.

4. The cutting system according to claim 1, wherein the length is about 105.7 millimeters.

5. The cutting system according to claim 1, wherein the titanium alloy is a Ti 6-Al 4-V alloy.

6. The cutting system according to claim 1, wherein the second section includes an elbow, such that at least a portion of the second section is elongated along the second axis.

7. The cutting system according to claim 1, wherein the cutting member defines at least one cutting surface, and further comprises an abrasive coating that covers at least a portion of the at least one cutting surface, and the abrasive coating is at least made from an abrasive material.

8. The cutting system according to claim 7, wherein the abrasive material comprises diamond particles.

9. The cutting system according to claim 7, wherein the abrasive material comprise diamond-like carbons.

* * * * *